United States Patent
Esch et al.

(10) Patent No.: US 10,357,305 B2
(45) Date of Patent: Jul. 23, 2019

(54) VENOUS DISEASE TREATMENT

(71) Applicant: Venclose, Inc., San Jose, CA (US)

(72) Inventors: Brady Esch, San Jose, CA (US);
Darius A. Przygoda, Milpitas, CA (US); Rory Thomas Christian, Gilroy, CA (US); Cody James Schindler, San Jose, CA (US)

(73) Assignee: Venclose, Inc., San Jose, CA (US)

( * ) Notice: Subject to any disclaimer, the term of this patent is extended or adjusted under 35 U.S.C. 154(b) by 162 days.

(21) Appl. No.: 14/670,338

(22) Filed: Mar. 26, 2015

(65) Prior Publication Data

US 2015/0272654 A1 Oct. 1, 2015

Related U.S. Application Data

(60) Provisional application No. 61/970,498, filed on Mar. 26, 2014.

(51) Int. Cl.
*A61B 18/08* (2006.01)
*A61B 18/14* (2006.01)
*A61B 18/00* (2006.01)

(52) U.S. Cl.
CPC ........ *A61B 18/082* (2013.01); *A61B 18/1492* (2013.01); *A61B 2018/00178* (2013.01); *A61B 2018/00404* (2013.01); *A61B 2018/00559* (2013.01); *A61B 2018/00577* (2013.01); *A61B 2018/00702* (2013.01); *A61B 2018/00791* (2013.01); *A61B 2018/00988* (2013.01)

(58) Field of Classification Search
CPC .............. A61B 18/082; A61B 18/1492; A61B 2018/00178; A61B 2018/00988;

(Continued)

(56) References Cited

U.S. PATENT DOCUMENTS 4,569,043 A   2/1986  Schieble et al.
4,581,017 A   4/1986  Sahota
(Continued)

FOREIGN PATENT DOCUMENTS

| EP | 0266957 A2 | 5/1988 |
|---|---|---|
| ES | 2242764 T3 | 6/2001 |
| WO | WO94/19051 A1 | 9/1994 |
| WO | WO99/42176 A1 | 8/1999 |
| WO | WO2004/028386 A1 | 4/2004 |

OTHER PUBLICATIONS

International Application No. PCT/US2015/022849, International Search Report and Written Opinion dated Jul. 2, 2015.

(Continued)

*Primary Examiner* — Michael F Peffley
(74) *Attorney, Agent, or Firm* — Shay Glenn LLP

(57) ABSTRACT

A technique allows for an electrical connection between a thermal abrasion heating catheter and the energy delivery console that utilizes serial communication. Accordingly, the serial communication allows data such as measured temperature, start/stop status, intended treatment area, device identification, device calibration parameters and/or use history to be conveyed along the same wires that deliver power to a heating element. For example, data can be conveyed along a two wire connection and provided at a frequency that is filtered out so that it is not delivered to a heating feature. In this example, one wire provides power to the heating element, one wire provided communication from the energy delivery console, and a third wire provides a common ground which the heating catheter uses to communicate with the energy delivery console.

46 Claims, 32 Drawing Sheets

(58) Field of Classification Search
CPC .......... A61B 2018/00577; A61B 2018/00702; A61B 2018/00791; A61B 2018/00559; A61B 2018/00404

See application file for complete search history.

(56) References Cited

U.S. PATENT DOCUMENTS

| | | | |
|---|---|---|---|
| 4,636,195 A | 1/1987 | Wolinsky | |
| 4,693,243 A | 9/1987 | Buras | |
| 4,897,789 A | 1/1990 | King et al. | |
| 4,994,033 A | 2/1991 | Shockey et al. | |
| 5,049,132 A | 9/1991 | Shaffer et al. | |
| 5,203,348 A | 4/1993 | Dahl et al. | |
| 5,213,576 A | 5/1993 | Abiuso et al. | |
| 5,222,938 A | 6/1993 | Behl et al. | |
| 5,254,089 A | 10/1993 | Wang | |
| 5,295,962 A | 3/1994 | Crocker et al. | |
| 5,383,874 A | 1/1995 | Jackson et al. | |
| 5,400,267 A | 3/1995 | Denen et al. | |
| 5,433,708 A | 7/1995 | Nichols et al. | |
| 5,540,681 A | 7/1996 | Strul et al. | |
| 5,573,533 A | 11/1996 | Strul et al. | |
| 5,582,609 A | 12/1996 | Swanson et al. | |
| 5,658,311 A | 8/1997 | Baden | |
| 5,701,905 A | 12/1997 | Esch | |
| 5,860,954 A | 1/1999 | Ropiak | |
| 6,014,589 A | 1/2000 | Farley et al. | |
| 6,109,971 A | 8/2000 | Vadlakonda | |
| 6,115,626 A * | 9/2000 | Whayne | A61B 5/0422 600/427 |
| 6,126,634 A | 10/2000 | Bagaoisan et al. | |
| 6,139,517 A | 10/2000 | Macoviak et al. | |
| 6,165,172 A | 12/2000 | Farley et al. | |
| 6,210,363 B1 | 4/2001 | Esch et al. | |
| 6,254,563 B1 | 7/2001 | Macoviak et al. | |
| 6,258,084 B1 | 7/2001 | Goldman et al. | |
| 6,308,089 B1 | 10/2001 | der Ruhr et al. | |
| 6,322,559 B1 | 11/2001 | Daulton et al. | |
| 6,387,092 B1 | 5/2002 | Burnside et al. | |
| 6,423,085 B1 | 7/2002 | Murayama et al. | |
| 6,459,363 B1 | 10/2002 | Walker et al. | |
| 6,471,699 B1 | 10/2002 | Fleischman et al. | |
| 6,544,221 B1 | 4/2003 | Kokish | |
| 6,592,612 B1 | 7/2003 | Samson et al. | |
| 6,616,659 B1 * | 9/2003 | de la Torre | A61B 18/085 128/898 |
| 6,651,669 B1 | 11/2003 | Burnside | |
| 6,663,627 B2 | 12/2003 | Francischelli et al. | |
| 6,673,042 B1 | 1/2004 | Samson et al. | |
| 6,676,971 B2 | 1/2004 | Goupil et al. | |
| 6,695,864 B2 | 2/2004 | Macoviak et al. | |
| 6,702,773 B1 | 3/2004 | Macoviak et al. | |
| 6,726,651 B1 | 4/2004 | Robinson et al. | |
| 6,936,047 B2 | 8/2005 | Nasab et al. | |
| 6,979,329 B2 | 12/2005 | Burnside et al. | |
| 7,013,178 B2 | 3/2006 | Reinke et al. | |
| 7,056,274 B2 | 6/2006 | Apple et al. | |
| 7,077,836 B2 | 7/2006 | Lary et al. | |
| 7,118,564 B2 | 10/2006 | Ritchie et al. | |
| 7,128,741 B1 | 10/2006 | Isaacson et al. | |
| 7,273,056 B2 | 9/2007 | Wilson et al. | |
| 7,357,800 B2 | 4/2008 | Swanson | |
| 7,517,349 B2 | 4/2009 | Truckai et al. | |
| 7,582,084 B2 | 9/2009 | Swanson et al. | |
| 7,625,372 B2 | 12/2009 | Esch et al. | |
| 7,674,258 B2 | 3/2010 | Swanson | |
| 7,824,408 B2 | 11/2010 | Mirizzi et al. | |
| 7,828,793 B2 | 11/2010 | Thompson et al. | |
| 7,837,677 B2 | 11/2010 | Thompson et al. | |
| 8,029,528 B2 | 10/2011 | Miller et al. | |
| 8,034,022 B2 | 10/2011 | Boatman | |
| 8,048,069 B2 | 11/2011 | Skwarek et al. | |
| 8,078,261 B2 | 12/2011 | Imam | |
| 8,182,446 B2 | 5/2012 | Schaeffer | |
| 8,317,747 B2 | 11/2012 | Kusleika | |
| 8,321,019 B2 | 11/2012 | Esch et al. | |
| 8,382,748 B2 | 2/2013 | Geisel | |
| 8,465,451 B2 | 6/2013 | McRae et al. | |
| 8,562,598 B2 | 10/2013 | Falkenstein et al. | |
| 8,636,729 B2 | 1/2014 | Esch et al. | |
| 8,721,634 B2 | 5/2014 | Esch et al. | |
| 8,795,266 B2 | 8/2014 | Esch et al. | |
| 9,055,956 B2 | 6/2015 | McRae et al. | |
| 9,226,766 B2 | 1/2016 | Aldridge et al. | |
| 9,289,258 B2 | 3/2016 | Cohen | |
| 9,295,515 B2 | 3/2016 | Wang et al. | |
| 9,351,785 B2 | 5/2016 | Hong et al. | |
| 9,351,786 B2 | 5/2016 | Ong et al. | |
| D781,885 S | 3/2017 | Bhat et al. | |
| 9,636,167 B2 | 5/2017 | Gregg | |
| 9,770,297 B2 | 9/2017 | Esch et al. | |
| 9,878,134 B2 | 1/2018 | Mirizzi | |
| D821,428 S | 6/2018 | Bhat et al. | |
| 10,022,180 B2 | 7/2018 | Deville et al. | |
| 2001/0020160 A1 | 9/2001 | Esch et al. | |
| 2002/0161351 A1 | 10/2002 | Samson et al. | |
| 2002/0193790 A1 | 12/2002 | Fleischman et al. | |
| 2003/0065322 A1 | 4/2003 | Panescu et al. | |
| 2003/0158571 A1 | 8/2003 | Esch et al. | |
| 2003/0158574 A1 | 8/2003 | Esch et al. | |
| 2004/0143312 A1 | 7/2004 | Samson et al. | |
| 2004/0158191 A1 | 8/2004 | Samson et al. | |
| 2004/0220561 A1 | 11/2004 | Kirwan et al. | |
| 2005/0004503 A1 | 1/2005 | Samson et al. | |
| 2005/0004559 A1 | 1/2005 | Quick et al. | |
| 2005/0080374 A1 | 4/2005 | Esch et al. | |
| 2006/0030849 A1 | 2/2006 | Mirizzi et al. | |
| 2006/0085054 A1 | 4/2006 | Zikorus et al. | |
| 2006/0106375 A1 | 5/2006 | Werneth et al. | |
| 2006/0142824 A1 | 6/2006 | Zikorus et al. | |
| 2006/0154198 A1 | 7/2006 | Durbin et al. | |
| 2007/0016272 A1 | 1/2007 | Thompson et al. | |
| 2007/0088346 A1 | 4/2007 | Mirizzi et al. | |
| 2007/0100405 A1 | 5/2007 | Thompson et al. | |
| 2007/0179575 A1 | 8/2007 | Esch et al. | |
| 2008/0167643 A1 | 7/2008 | Mizrahi et al. | |
| 2009/0131930 A1 * | 5/2009 | Gelbart | A61B 18/1492 606/41 |
| 2010/0069881 A1 | 3/2010 | Salerno | |
| 2011/0112530 A1 | 5/2011 | Keller et al. | |
| 2011/0257645 A1 | 10/2011 | Thompson et al. | |
| 2012/0065636 A1 | 3/2012 | Thompson et al. | |
| 2012/0098351 A1 | 4/2012 | Ross | |
| 2012/0259315 A1 | 10/2012 | Hattangadi et al. | |
| 2013/0006228 A1 * | 1/2013 | Johnson | A61B 18/1477 606/14 |
| 2013/0030410 A1 | 1/2013 | Drasler et al. | |
| 2013/0165916 A1 * | 6/2013 | Mathur | A61B 18/18 606/33 |
| 2013/0190796 A1 | 7/2013 | Tilson et al. | |
| 2013/0310829 A1 | 11/2013 | Cohen | |
| 2014/0171941 A1 | 6/2014 | Thompson et al. | |
| 2015/0094703 A1 | 4/2015 | Zikorus | |
| 2015/0094704 A1 | 4/2015 | Hong et al. | |
| 2015/0209457 A1 * | 7/2015 | Bonutti | A61L 2/10 250/435 |
| 2015/0342674 A1 | 12/2015 | Mirizzi et al. | |

OTHER PUBLICATIONS

Ji et al.; Endovascular Electrocoagulation: Concept, Technique, and Experimental Results; AJNR Am J Neuroradial; 18(9); pp. 1669-1678; Oct. 1, 1997.

* cited by examiner

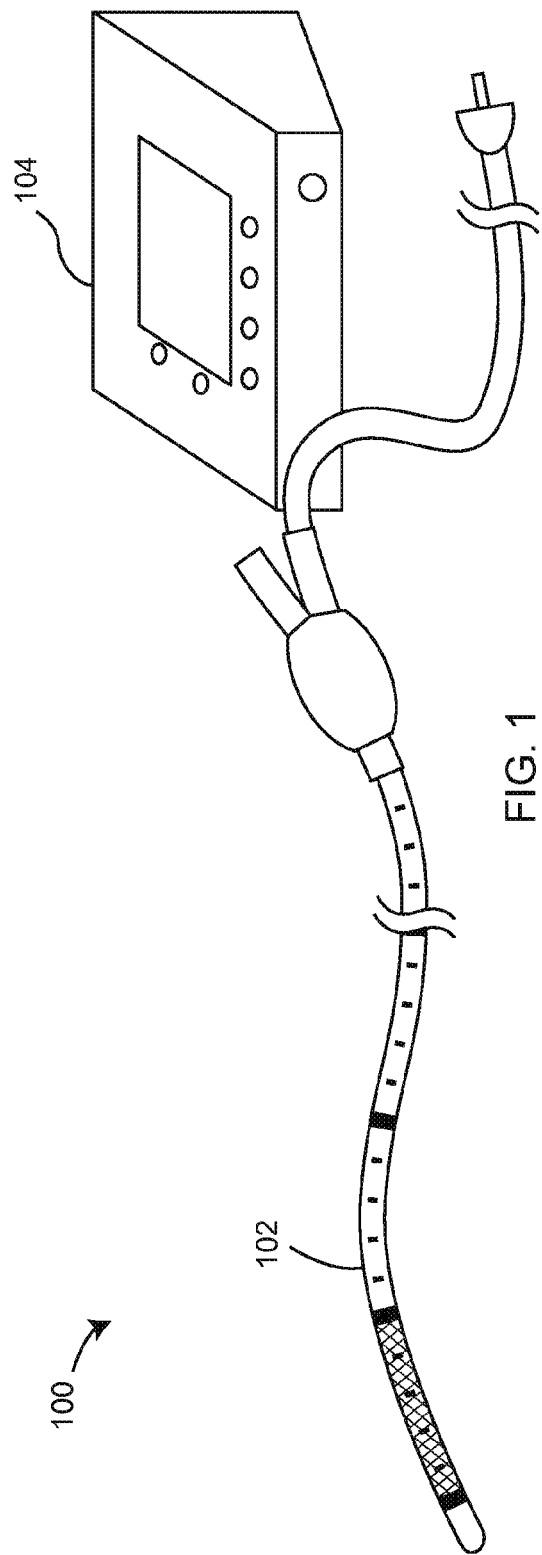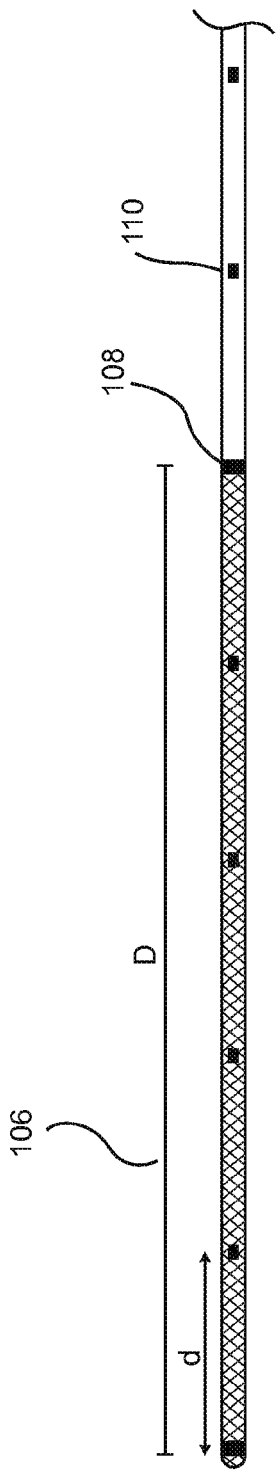

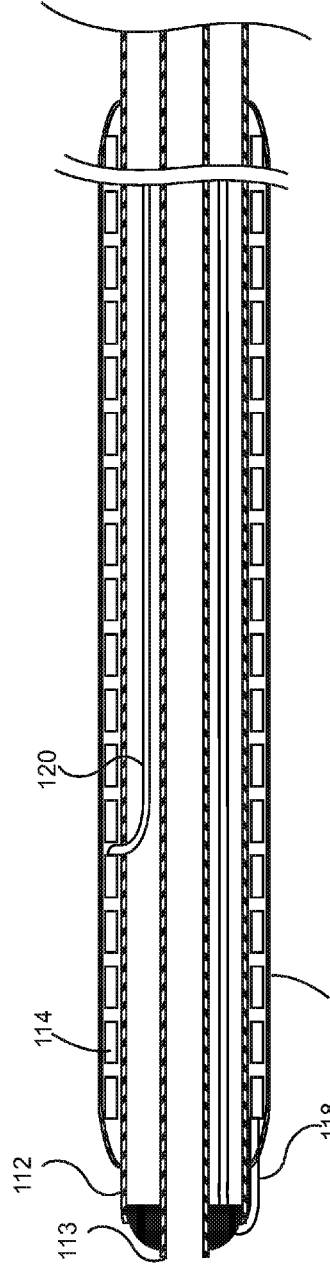
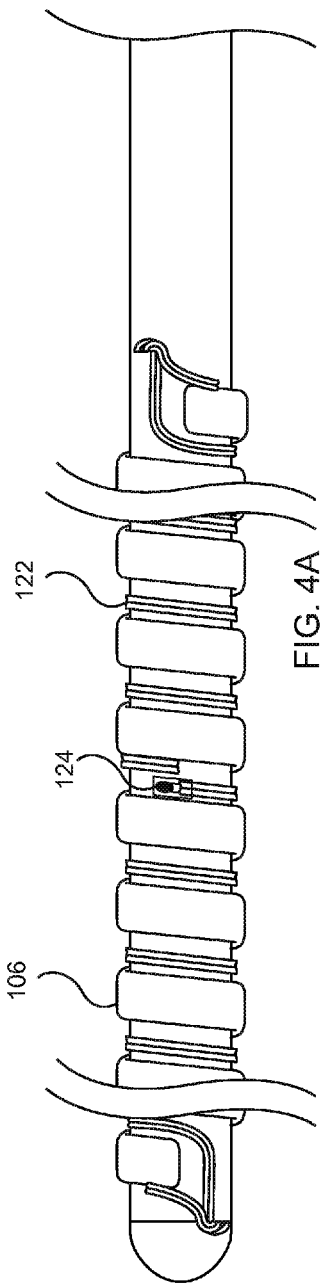
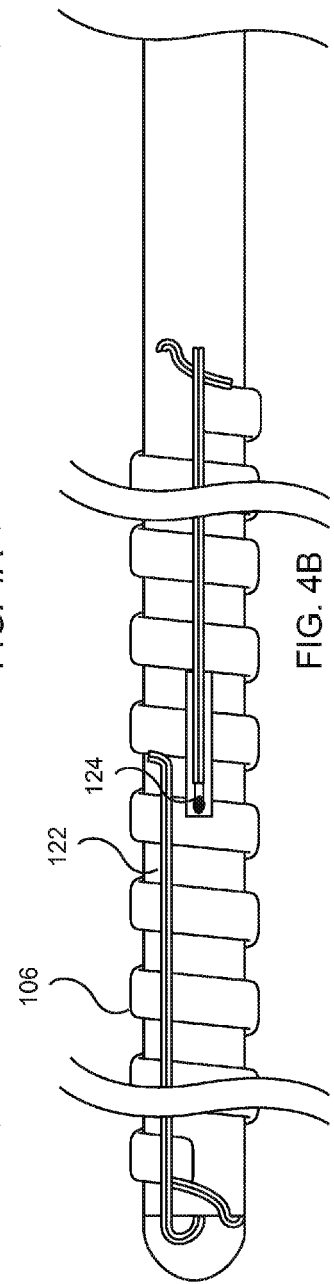
FIG. 3
FIG. 4A
FIG. 4B

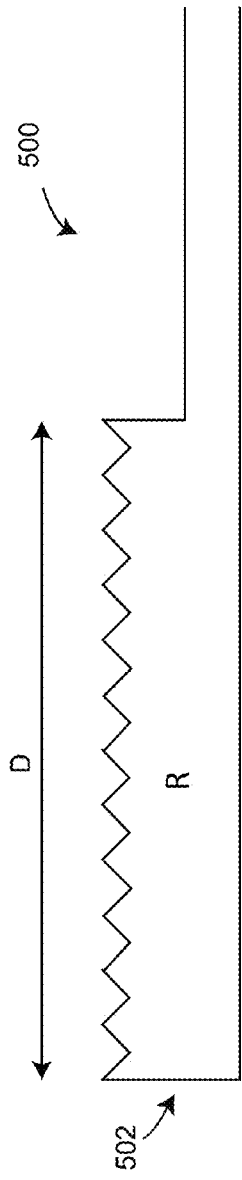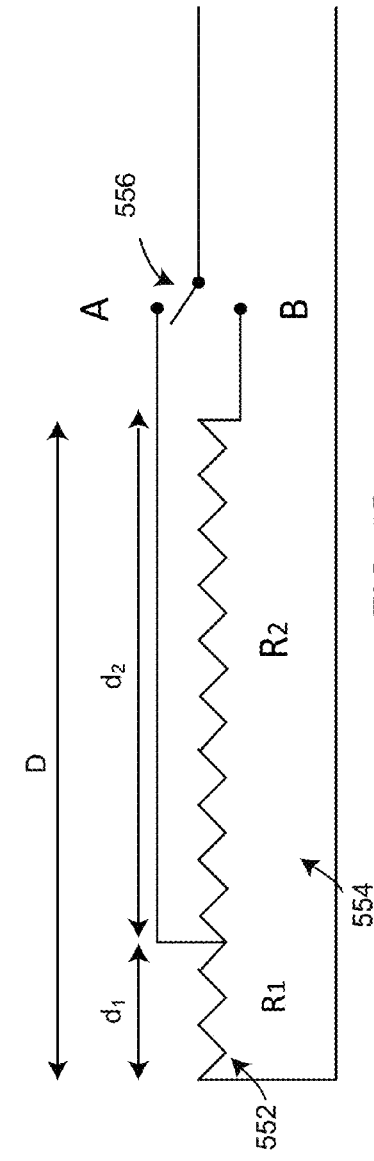

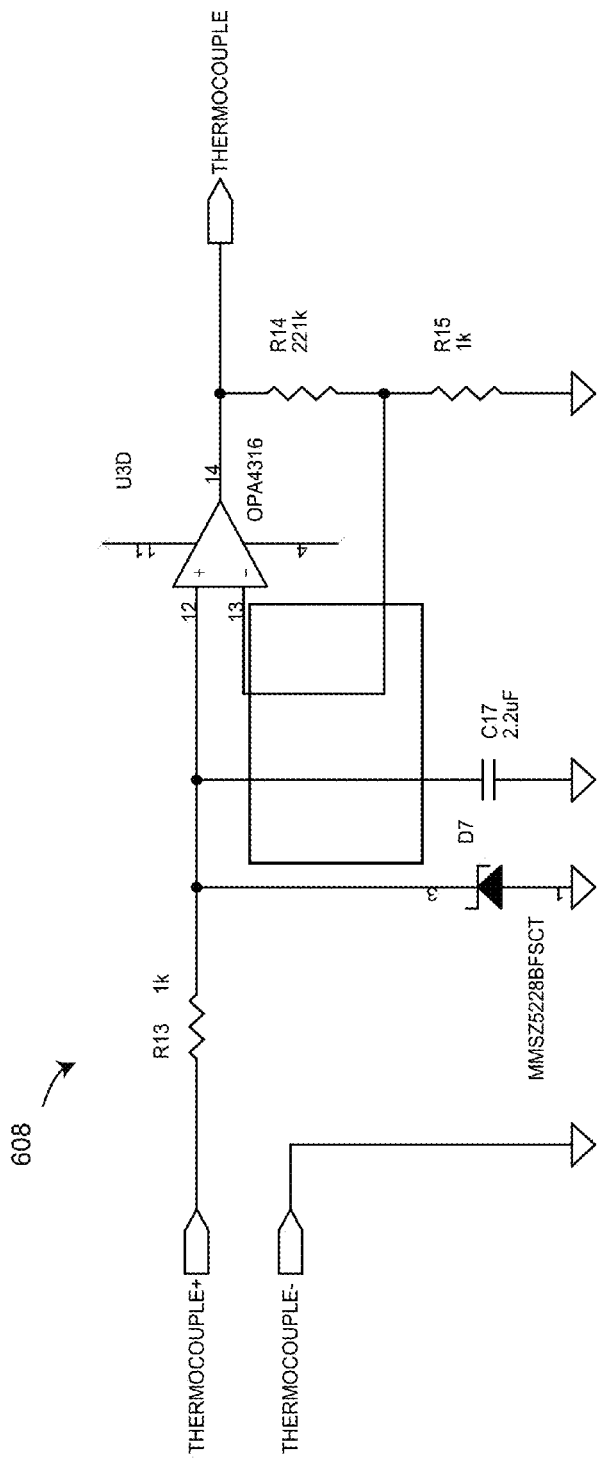
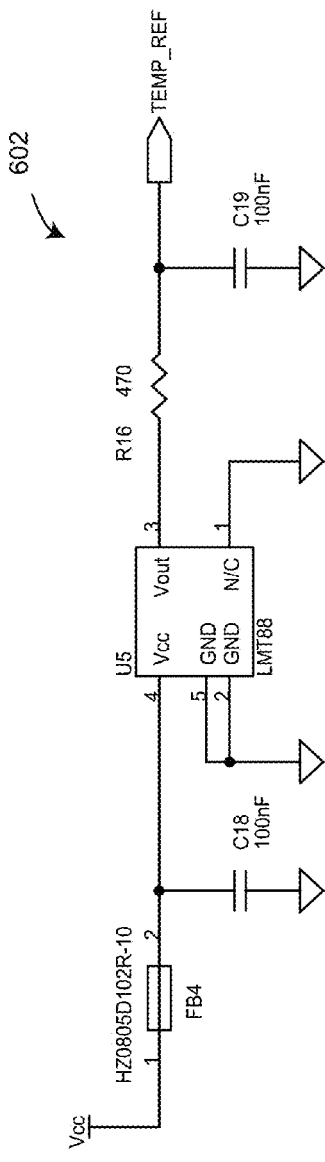
FIG. 9

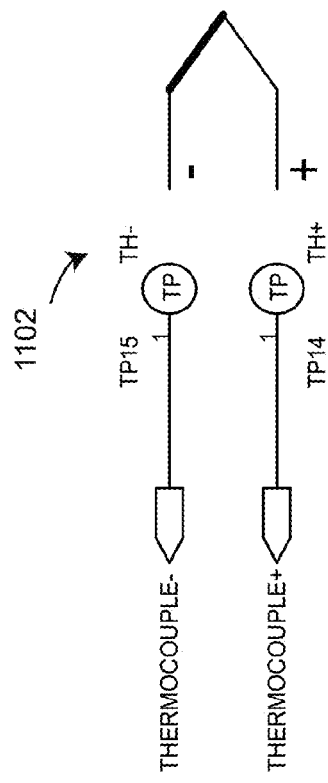
FIG. 11 B
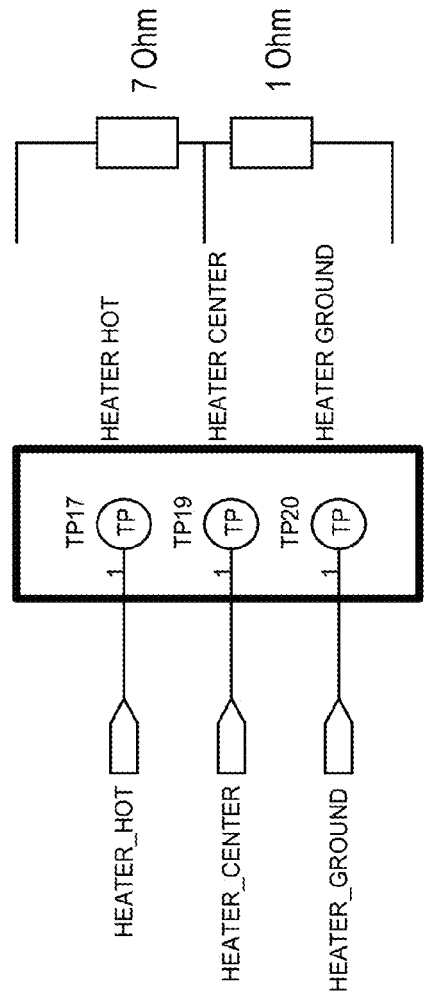
FIG. 11 C
FIG. 11 A

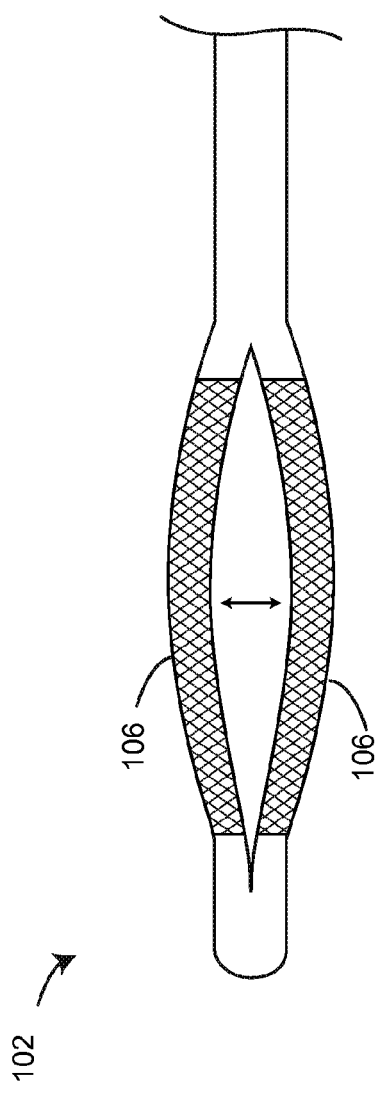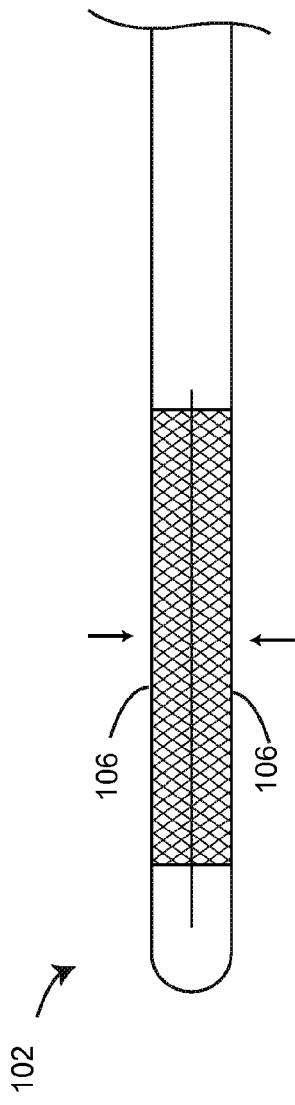
FIG. 34 A
FIG. 34 B

VENOUS DISEASE TREATMENT

CROSS-REFERENCE TO RELATED APPLICATIONS

The present application claims benefit of U.S. Provisional Patent Application No. 61/970,498, filed Mar. 26, 2014, entitled "VENOUS DISEASE TREATMENT," which is incorporated by reference herein.

BACKGROUND

Blood vessels and other physiological structures can fail to perform their proper function. An example, in the case where opposing valve leaflets within a vein do not touch each other, blood flow within the vein is not predominately restricted to one direction towards the heart. This condition is called venous reflux, and it causes elevated localized blood pressure within the vein. Elevated localized blood pressure is subsequently transferred to the surrounding tissue and skin. Furthermore, failure of a valve in a vein causes a cascading reaction of successive failure of valves along the vein. In order to standardize the reporting and treatment of the diverse manifestations of chronic venous disorders, a comprehensive clinical-etiology-anatomy-pathophysiology (CEAP) classification system has been developed to allow uniform diagnosis. The CEAP classification is commonly used to describe the level of patient symptoms, which increase in severity from spider veins, to varicose veins, to swelling (edema), to skin changes (bluish staining, lipodermatosclerosis), to previously healed ulcer, finally to active ulceration which is regarded most severely. Chronic venous insufficiency is a term often used to describe the more severe symptoms of chronic peripheral venous disease.

The human lower extremity veins consist of three systems: the superficial venous system, the deep venous system, and the perforating venous system, which connects the superficial and the deep systems. The superficial system includes the great saphenous vein (GSV) and the small saphenous vein (SSV), among others. The deep venous system includes the anterior and posterior tibial veins, which unite to form the popliteal vein that in turn becomes the femoral vein when joined by the small saphenous vein.

An early technique for treatment of venous reflux is surgical stripping of the vein. This is done by passing a flexible rod or cable through the vein, and then either pulling back with an acorn-shaped head to help sever the vessel side-branches or pulling the vein out through the lumen of the vein (invaginate stripping). The stripping method typically requires general anesthesia and usually requires a prolonged healing period of up to two weeks due to heavy bruising, pain and tenderness.

Sclerotherapy is a treatment where a caustic solution (e.g., polidocanol, sodium tetradecyl sulfate, sodium morruate, isotonic saline) is injected into the vein causing irritation of the vein wall to such a degree that the vein wall is damaged and the vein lumen is filled with thrombosis (clot). Sclerotherapy can be effective, but it often requires repeat treatments and it has been reported to cause a higher rate of nearby deep vein thrombosis, as well as staining/matting of nearby skin. Larger veins are often treated with a foamed mixture of sclerosant with air or Carbon Dioxide. Sclerotherapy does not generally require any anesthesia, although there can be some tolerable pain upon injection of the solution.

Endovenous thermal ablation is a recent technique where heat is applied within the vein to cause the vein wall to permanently shrink to the point the vein lumen is occluded (usually by a residual core of blood thrombus). Radiofrequency ablation was first reported, followed by laser ablation and then steam ablation. Endovenous ablation is typically done with local anesthesia in an outpatient or physician office setting.

BRIEF DESCRIPTION OF THE DRAWINGS

FIG. 1 depicts a diagram of an example of an energy delivery system for providing endovenous thermal ablation.

FIG. 2 depicts a diagram of an example of a heating element of a heating catheter for providing endovenous thermal ablation.

FIG. 3 depicts a diagram of an example cross section view of a heating catheter.

FIGS. 4A and 4B depict diagrams of example heating elements of a heating catheter.

FIGS. 5A and 5B depict example diagrams for two example heating elements of a heating catheter.

FIG. 9 depicts a diagram of an example thermocouple amplifier and an example temperature reference engine of a heating catheter.

FIGS. 11A-11C depict diagrams of example communication connections for a heating catheter.

FIGS. 34A and 34B depict an example heating catheter designed to promote dual-zone heating within a vein lumen.

DETAILED DESCRIPTION

Figure 6:
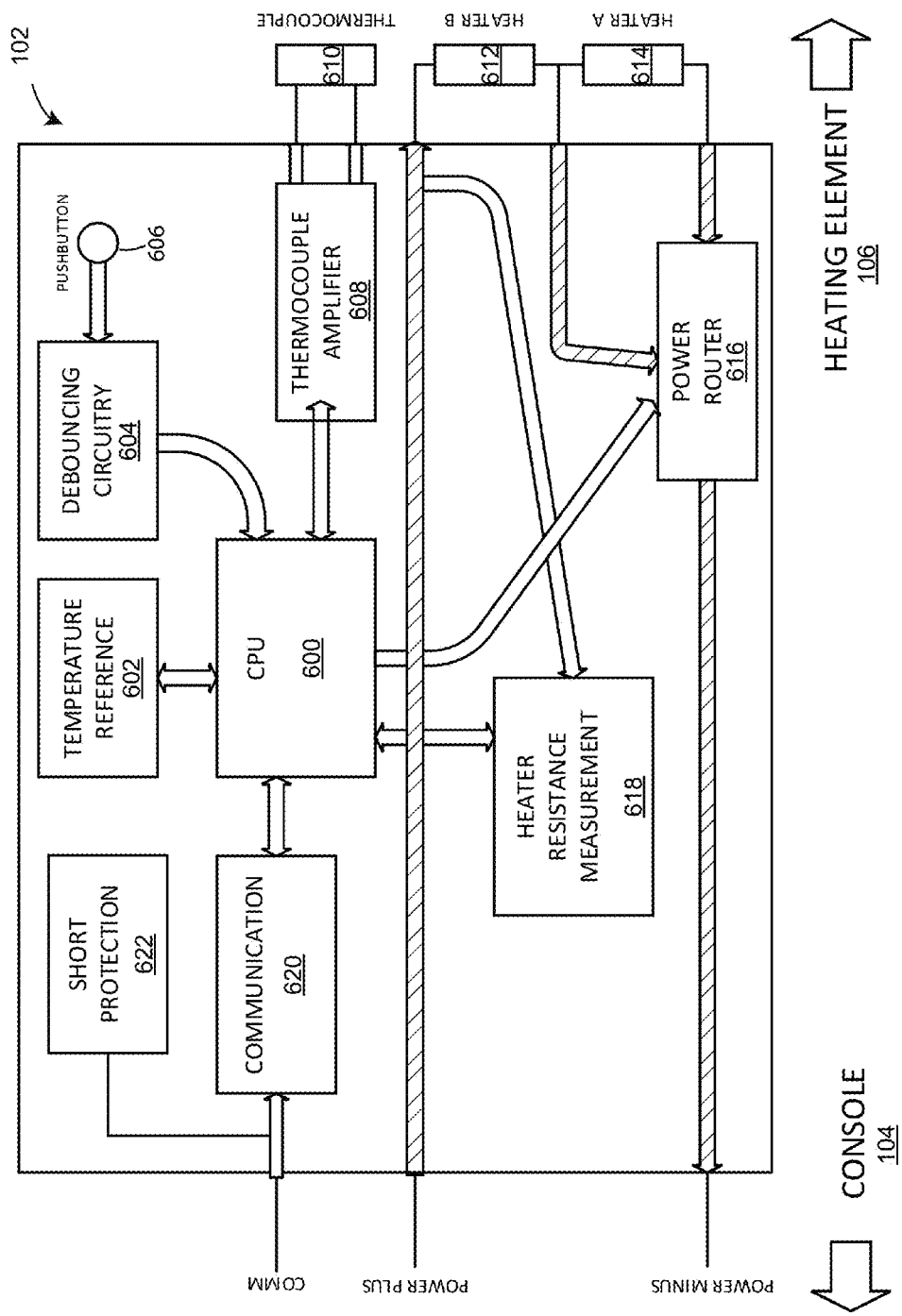
FIG. 6 depicts an example block diagram of a heating catheter.

FIG. 1 depicts example energy deliver system 100 for performing thermal ablation. In this example, energy delivery system 100 includes heating catheter 102, which is a long, thin, flexible, or rigid device that can be inserted into a narrow anatomical lumen such as a vein, and energy delivery console 104. Heating catheter 102 is connected to energy delivery console 104 to provide energy causing heating at the distal end of heating catheter 102, which can be placed within the lumen of a vein to be treated.

FIG. 2 depicts heating catheter 102 having heating element 106 that is heated by electrical current. The electrical current generated in heating element 106 transfers heat energy to the vein wall by conduction (conductive heating). In a specific implementation, the active heating length of heating element 106 can be selectable by the user. For example, the active heating length could be selectable from 1 cm to 10 cm). In this example, a user (e.g., doctor, surgeon, etc.) could select a heating length as small as d (e.g., 1 cm) up to a length of D (e.g., 10 cm), for example, by selecting a switch on heating catheter 102 or energy delivery console 104. Here, markings 108, 110 can be provided at different lengths along heating catheter 102 to guide a user by visual cues, such as a series of dots 110, spaced approximately equal to the length of the shortest heating length d and another visual cue, such as a series of lines 108, spaced approximately equal to the length of the longer heating length D. This can be done to indicate where the shorter length of heating is, or to facilitate segmental positioning and heating of the shorter length of heating within the blood vessel.

In a specific implementation, markings 108, 110 could be geometric lines or shapes, alphanumeric characters, color-coded features, or a combination thereof. In a further variation, markings 108, 110 can be placed at intervals approximately equal to the length of heating element 106 (such as 10 cm apart when the heating element is 10 cm long), or slightly longer than heating element 106 (such as 10.1 cm apart when the heating element is 10 cm long) to prevent accidental overlapping of treatments. Prevention of overlap of the heating segments has two main advantages: first, avoiding overlaps helps with the speed of the procedure, as the treatments will ablate the longest possible length of vessel with each treatment, and second, overlap of treatments creates additional heating at the overlap region and this may lead to unnecessary tissue injury. Markings 108, 110 can include alignment markings to facilitate location of the heating element and/or tubing bonds.

In a specific implementation, a marking or discernable feature can indicate a minimal distance of treatment away from the active length of heating element 106, giving the user a cue to avoid tissue heating too near the patient's skin. In one example, a marking or edge of a tubing layer or bond can be 2.5 or 3.0 cm proximal to the proximal end of the heating element 106.

FIG. 3 depicts a cross-sectional view of heating element 106. In this example, treatment catheter 102 may is comprised of tube 112 around which coils 114 are wound or placed. Coils 114 have an associated resistance causing them to heat up when electrical current passed through them enabling heat energy to be produced that is eventually applied to the vein wall by conduction (conductive heating). Tube 112 provides a channel through which wires 118, 120 can be run to provide an electrical connection between coils 112 and the catheter handle, ultimately communicating with the energy delivery console 104. A smaller tube 113 is inside tube 112 to facilitate injection of fluids or passage of a guide wire. Other items may also use the channel provided by tube 112, such as temperature sensors and the like. In a specific implementation, a wire loading channel can be cut into tube 112 through which wires 118, 120 connecting coils 114 can be provided through to hide and protect these wires and lessen the profile of heating catheter 102. Additionally, non-stick outer layer 116 is provided over coils 114 of heating element 106 to, for example, prevent direct contact with vein tissue and facilitate smooth and easy movement of heating catheter within the vein lumen.

In a specific implementation, non-stick outer layer 116 can be a shrink tubing made from polytetrafluoroethylene (PTFE), fluorinated ethylene propylene (FEP), or another applicable outer jacket preferably, though not necessarily, of low surface energy material. Additionally, a higher-friction outer jacket can be treated to have reduced friction, such as a fluorinated or parylene-coated polyethylene terephthalate (PET) layer. Furthermore, an additional section of heat shrink tubing (e.g., PET, 0.0005"-0.001" thick) can be placed over one or both ends of the non-stick outer layer to strengthen the assembly of heating catheter 102. Alternatively, coils 114 can be coated to prevent sticking to tissues, such as a blood vessel wall.

In a specific implementation, the outer diameter of heating element 106 and heating catheter 102 can be 7 F (2.33 mm) or smaller (e.g., 6 F (2.0 mm), 5 F (1.67 mm), 4 F (1.33 mm), etc.). The length of heating element 106 may be equivalent to the length of the shortest vessel(s) typically treated. For example, heating element 106 can be approximately 10 cm long for treatment of long vessels where, in another example, heating element 106 can be approximately 1 cm long for treatment of short vessels. In various other examples heating element lengths can be 15 cm, 7 cm, 5 cm or 3 cm. Heating element 106 can be covered with a non-stick outer jacket having, for example, a thickness of approximately 0.0005" to 0.001", or approximately 0.001" to 0.003". Short catheter heating lengths are often combined with a technique of slowly retracting the heating catheter along the vessel lumen (continuous pullback ablation) causing the vein lumen to close in a manner similar to a clothing zipper closing an opening as the slider is pulled along. Longer catheter heating lengths are often combined with a technique of heating the vein lumen while the catheter is stationary, causing a section of the vein wall to simultaneously shrink to closure (segmental ablation).

In a specific implementation of an example energy delivery system, heating element 106 can be created from a coiled configuration of wire (single or double-lead). Accordingly, FIGS. 3-4 depict a coiled configuration of wire that creates heating element 106. In the example of FIG. 3, wire cross-section 112 has a rectangular profile, however, the profile can be also round or oval to increase the cross-sectional area while decreasing the outer diameter of heating element 106, with a goal of effective generation of heat within the coil with fast transfer of heat to the surrounding bodily tissue that is intended to be treated. Exemplary materials for heating element 106 can be stainless steel (a commonly-used heating element material for heating to low temperatures such as below approximately 300° C.); nichrome wire; ferrous alloys; nickel titanium; elgiloy; MANGANIN® or alloys of approximately 86% copper, 12% manganese, and 2% nickel; MONEL® or alloys primarily composed of nickel (up to 67%) and copper, with small amounts of iron, manganese, carbon, and silicon; or nickel alloys, among others.

FIGS. 4A and 4B depict diagrams of heating element 106 of heating catheter 102. The spiral shape of coils 114 around tube 112 may be more apparent be in diagrams relative to FIG. 3. In a specific implementation, temperature sensor 124 (e.g., thermocouple or thermistor) can be located along the length of heating coil 114, such as at a position 1-3 cm from the distal end of heating catheter 102. As discussed above, temperature sensor 124 can be placed between coil winds (with spacing or insulation to prevent electrical shorting across coils), over the coil assembly (insulated, for example, by a layer over the metal coil such as FEP, PTFE or parylene to prevent electrical shorting across coils), under the coil assembly, or within the body of heating catheter 102 under the heating element area. Wiring 122 that connects to temperature sensor 124 can be directed into the body or tube 112 of heating catheter 102 near the point temperature sensor 124 is active in measuring, or the wires can be directed per one of the conductive wire methods described herein.

In a specific implementation, a wire-in-wall configuration of tubing is used under heating element 106, where a bifilar thermocouple wire is embedded within the wall thickness of the tubing; this bifilar wire is exposed at the intended measurement location, such as by laser drilling, and an electrical junction is formed before or after loading heating element 106 onto tube 112. In one example, a thermistor is placed within a depression made by permanently deflecting one or more heating coil winds inwardly. In one embodiment, a thermistor is placed within a depression in the tubing surface over which the heating coil is loaded; such a depression can be created by cutting a pattern into the surface of the tubing or by thermally modifying the surface.

In a specific implementation, treatment catheter 102 is produced to be for one-time use, after which, treatment catheter 102 is disposed of. Accordingly, the individual pieces or components of treatment catheter 102 are chosen with cost reduction in mind. For example, a lower-cost heating element 106 may be constructed using a rectangular-profile stainless steel wire of thickness approximately 0.002"-0.005" and width approximately 0.020"-0.025" wound into a coil with a pitch length of 0.030"-0.040" creating a gap between coils of approximately 0.005"-0.020". If the coils are in contact, or may occasionally contact, the coil wire can be coated (e.g., with a 0.0005"-0.005" layer of polyimide, PTFE, FEP, PET, perfluoroalkoxy alkane (PFA), or other coating) to electrically insulate each coil. Alternatively, an amount of nonconductive material can be located in the spaces between successive coils, such as a filament wound in between coils similar to a double-helix configuration, to provide a physical barrier against coil-to-coil direct contact.

In various implementations, it may not be necessary to add electrical insulation to or between coils 114 if the gap between coils 114 is sufficient to prevent coil-to-coil direct contact when heating element 106 of treatment catheter 102 is flexed to the tightest radius expected during use. For this purpose, a more preferable gap between coils 114 may be approximately 15% to 33% of the width of the coil element, since larger gaps decrease the available heating area of heating element 106 in the coiled configuration.

In a specific implementation, for a heating length of 10 cm, an example heating coil resistance is approximately 8Ω if it will be heated to a maximum power level of 57.1 W by a 24 V power source at 2.38 A, with approximately 2Ω of resistance in the wire and cable of the catheter. For a heating length of 7 cm, an example heating coil plus wire resistance is approximately 14.4Ω if it will be heated to a maximum power level of 40 W by a 24 V power source at 1.67 A. For a heating length of 1.0 cm, an example heating coil plus wire resistance is approximately 101Ω if it will be heated to a maximum power level of 5.7 W by a 24 V power source at 0.238 A. Alternate power sources, such as 12 V, 9 V and 3 V, will have different resistance range needs as determined by the relationships $I=P/V[A=W/V]$ and $R=P/I^2[\Omega=W/A^2]$.

In a specific implementation, two ends of a heating element (for a single-lead coil configuration) can be attached by solder to copper or similar conductor wires of sufficiently low resistance that extend through or along the length of the energy delivery catheter shaft to a handle or cable connector which ultimately connects to the energy delivery system. One or more temperature measuring features (e.g., thermocouple, thermistor, resistance temperature detector) can be located along the length of the heating element or configured within the heating element. It may be beneficial for the thermocouple location to fall within a region that can be viewed by ultrasound while imaging the tip of the catheter. Since linear ultrasound probes are often approximately 2.0 to 4.0 cm wide, an exemplary location of temperature measurement is 1.0 to 3.0 cm proximal to the distal end of the heating coil. It is important to locate at least one of such temperature measuring features (when one or more are included in the device) within the region of the heating element that is most likely to be tightly compressed against the vein wall; when the heating element is visualized in part during treatment with an ultrasound probe, that region of compression is generally within the distal-most 3.0 to 4.0 cm of the heating element.

FIG. 5A depicts an example diagram 500 of heating element 502. In this example, heating element 502 is shown as a long resistor with length D and resistance R, where electric current running through the resistor R creates heat. In a specific implementation, an active heating length of a heating element can be selectable and adjustable by a user. As a result, thermal ablation heating catheter 102 can be used to quickly treat long vein segments while also being able to treat much shorter lengths. Accordingly, FIG. 5B depicts diagram 550 of heating catheter with first heating element portion 552 with length d1 and resistance R1 and second heating element portion 554 with length d2 and resistance R2. In this example, d2 is longer than d1 where d1 and d2 together equal length D. Thus, depending on the desired treatment, a user can select to have the desired heating length using switch 556. In this example, if switch 556 is flipped to A, only first heating element 552 corresponding to length d1 will be turned on and, if switch 556 is flipped to B in this example, first heating element 552 and second heating element 554 will be turned on.

In a specific implementation, length D is 10 cm and d1 is 1.0 or 2.5 cm long. Another example configuration is a 7 cm heating element that can heat along its entire length or along only the most distal 3 cm. A further example configuration is a 6 cm heating element that can heat along its entire length or along only the most distal 2 cm. Three selectable lengths would also be advantageous, such as 10 cm, 3 cm or 1 cm, however, it should be appreciated that any number of selectable lengths are possible.

In a specific implementation, in order for the same energy delivery system to effectively power and control both longer-length and shorter-length heating elements (either switchable on the same energy delivery catheters or with use of two or more different types of energy delivery catheters), it is desirable to be able to adjust the power source voltage to a lower value for shorter-length devices. As stated above, a 10 cm heating length heated to 57.1 W by a 24 V power source at 2.38 A can have a resistance of 8Ω, however a 1.0 cm heating element operated at the same Watts per unit length (5.7 W) with the same 24 V power supply could have a resistance of 80Ω. Since ⅒th of the length of the 10 cm physical heating element (designed to have a resistance of 8Ω over the 10 cm length) would have an inherent resistance of 0.8Ω, it is only ¹⁄₁₀₀th of a target resistance for operation at 24 V. Instead, this shorter 1.0 cm heating element length (with 0.8Ω resistance) could instead be driven by 2.38 A at 2.4 V. This reduced voltage can be achieved using a transformer (e.g., ferrite transformer) or resistor, preferably built into energy delivery console 104 or alternatively it can be built into heating catheter 102 (e.g., within the handle or cable assembly). More practical voltages are 9 V and 3 V, with appropriately-balanced heating element resistances to achieve approximately 5.7 W/cm of maximum heating, which is then reduced to lower levels of heating as necessary to maintain a target temperature. Note that this level of heating is an appropriate match for a studied protocol for thermal ablation of veins at 120° C. with a reasonably fast heating time, but alternative perturbations of higher or lower maximum heating may also be employed; examples are greater than 6 W/cm for even faster heating or to a higher temperature or over a larger diameter heating element, or less than 5 W/cm for slower heating or to a lower temperature.

In a specific implementation, heating element 106 has at least three wire connections for switchable heating lengths (first heating element 552 or first heating element 552+ second heating element 554) and each of the two heating segments of the heating element includes a temperature sensor. One example configuration is heating element 106 with a 2.5 cm distal heating length (temperature sensor mid-length at 1.25 cm) and a 7.5 cm proximal heating length (temperature sensor mid-length at 3.75 cm). A further specific implementation is to configure the energy control to heating element 106 so that either or both of the heating segments can be actively heated, so that each segment can be independently controlled such as to reach and maintain a treatment temperature. A preferable configuration would be for the electrical connection within the length of the heating element (not the connections at the two ends) to be a shared ground. A similar specific implementation could be a 20 cm heating element configured as 10 cm heating segments. Three or more segments can similarly be configured.

In a specific implementation, electrical attachment of conduction wires to the heating element by solder is facilitated by plating at least a portion of the heating element with another material that is easier to solder (e.g., not requiring caustic acid flux). Exemplary plating materials are gold, tin and nickel. Plating may be done from a component wire (such as plating the wire spool-to-spool) before the wire is formed into a heating element shape, or the completed heating element shape may be plated. The entire heating element may be plated or selected regions at the locations of solder contact can be plated.

In a specific implementation a distal tip of heating catheter 102 can have a rounded end (full round) or it can be shaped like a dilator with a generally tapered shape so that heating catheter 102 can be introduced directly into a vein over a long access guide wire with no need for an introducer sheath. There can be a lumen (e.g., for guide wire or fluid passage therethrough) extending from that tip through the length of the heating catheter shaft to the handle or connector at the proximal end of heating catheter 102. The lumen can be of a size to slide-ably accept guide wires of approximately 0.014", 0.018", 0.025" or 0.035" diameter. Alternatively, the lumen can end part-way along the heating catheter shaft, such as exiting through a side-port approximately 20 cm proximal of the distal tip. The lumen interior can feature elongate ribs, which would act as standoffs to reduce the surface area of the lumen contacted by a guide wire, reducing the friction. In a specific implementation there exists no guide wire or fluid lumen within the body of heating catheter 102.

In a specific implementation, a handle or connector hub for thermal ablation heating catheter 102 connects to the catheter shaft, containing the electrical connections of the heating element conductive wire leads and temperature sensor 124 leads as well as providing a fluid connection with the guide wire lumen (if present). The handle can also include a button or actuation feature that communicates with energy delivery console 104 to indicate that the user is ready for a heating treatment to begin (or stop early). The handle button can be located on the top surface or side of the handle, or the handle design can be configured to allow the handle to be pressed or squeezed on either side to activate. The start/stop actuation feature can prevent accidental actuation of treatment start; this can be accomplished by requiring more force than would normally be exerted with incidental contact, and/or by including geometric features that act to prevent accidental contact with the actuation feature. In one embodiment the handle has a very highly textured surface to provide maximum grip; such a surface can be incorporated as a feature of the injection mold for the part, with generally tapered pockets of depth between 0.001" and 0.01", and may be aligned to the angle that the part pulls from the mold.

Figure 7:
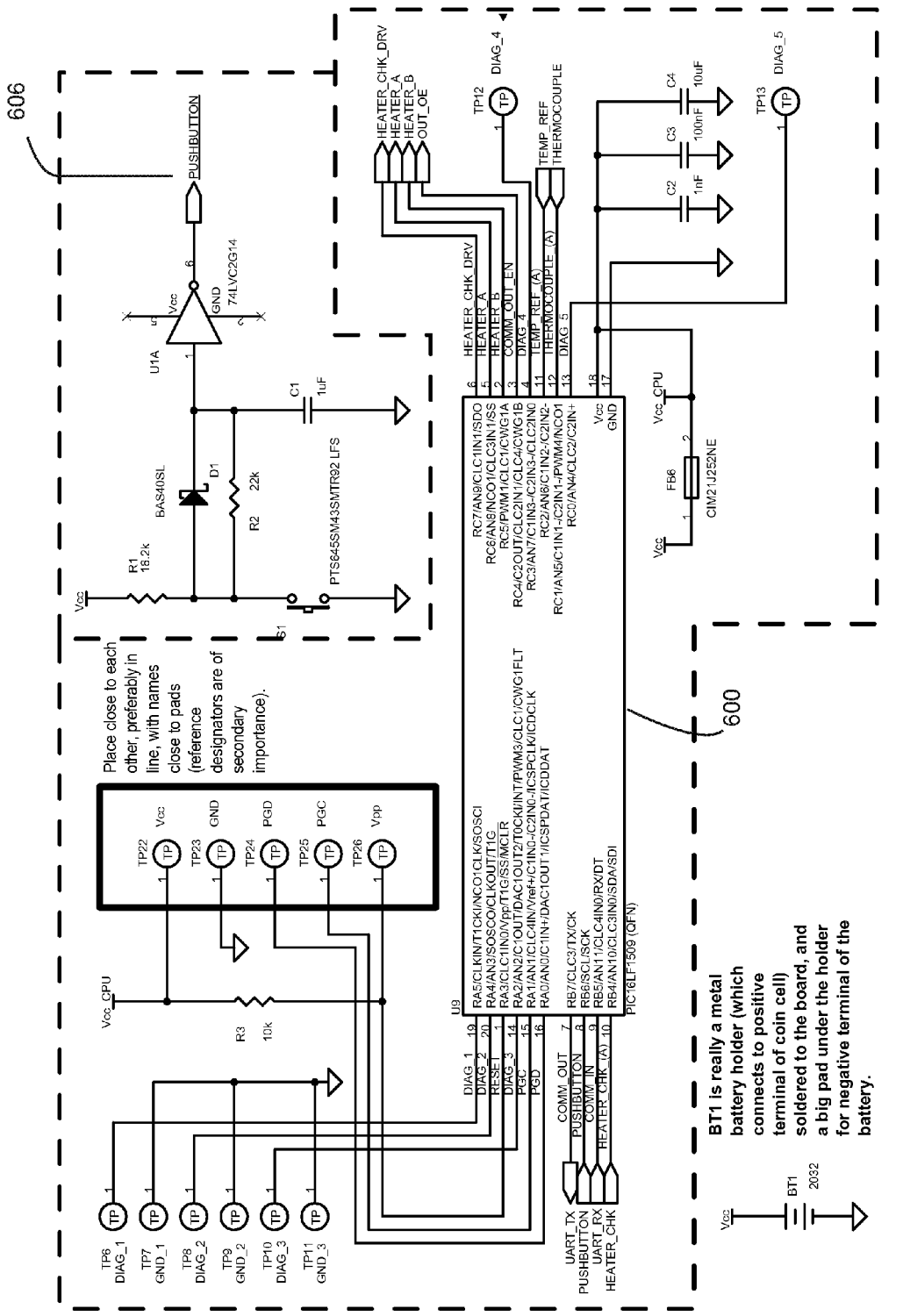
FIG. 7 depicts a diagram of an example central processing unit for a heating catheter.

FIG. 6 depicts an example block diagram of heating catheter 102. In a specific implementation, heating catheter 102 includes central processing unit (CPU) 600, which is in communication with temperature reference engine 602, debouncing circuitry 604 for pushbutton 606, thermocouple amplifier 608 for thermocouple 610, power router 616, heater resistance measurement engine 618, and communication engine 620. FIG. 7 depicts an example circuit diagram of CPU 600 and pushbutton 606 in accordance with one specific implementation. Power plus is provided to heating catheter 102 from energy delivery console 104 to heater B 612, or to the combination of B 612 and A 614, as selected by power router 616, and out power minus. Note the connection between heater A 614 and heater B 612 to power router 616 enabling a user to selectably switch between using only heater B 612 or both, as discussed above with respect to FIG. 5B. Note in these figures that heater A 614 and heater B 612 are analogous to 552 and 554 (612≈552, 614≈554 and 616≈556).

Figure 8:
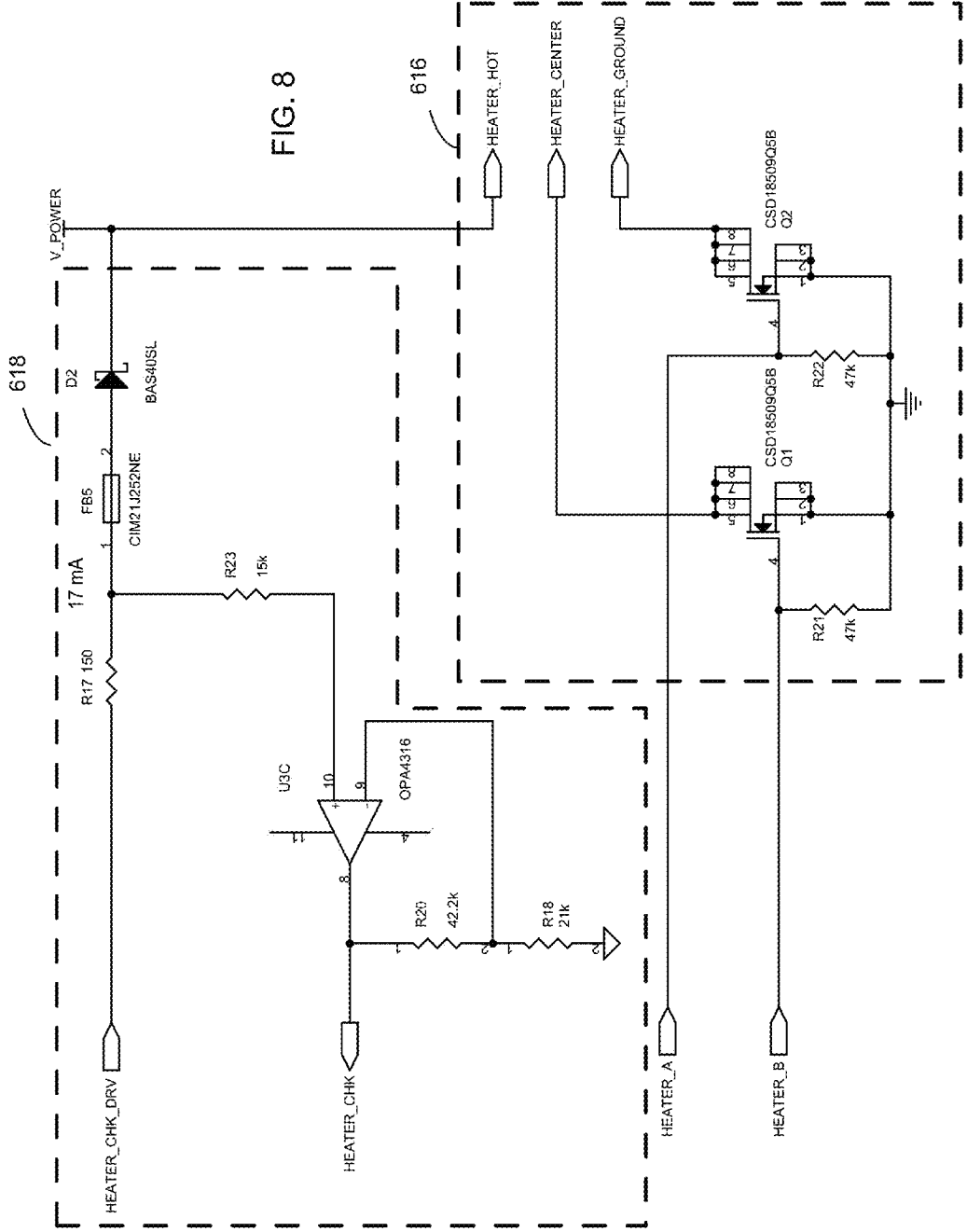
FIG. 8 depicts a diagram of an example heater resistance measurement engine and an example power router engine of a heating catheter.
Figure 10:
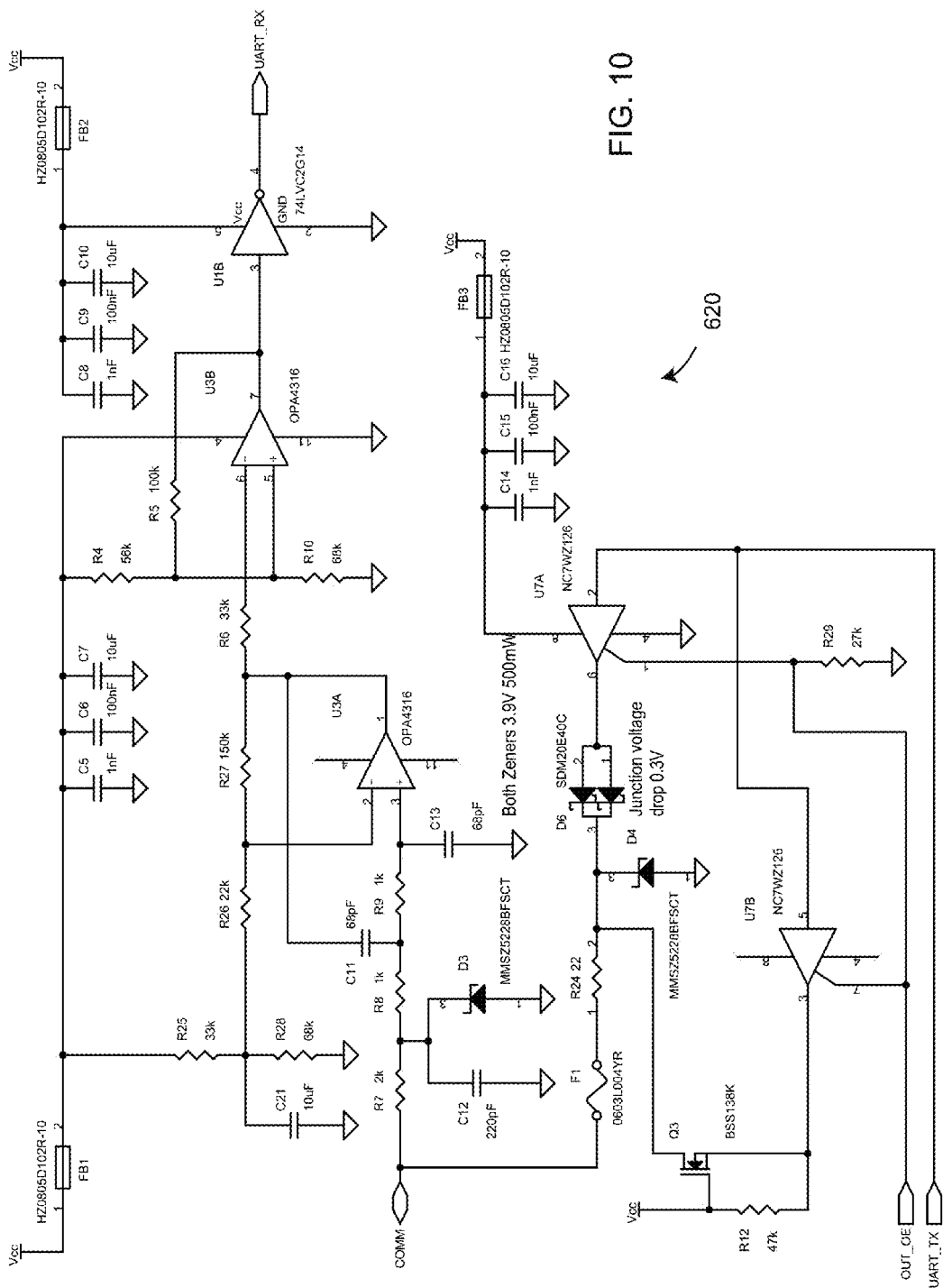
FIG. 10 depicts a diagram of an example communication engine of a heating catheter.

In this example, heater resistance measurement engine 618 can monitor and measure the resistance of the selected heater(s). FIG. 8 depicts an example circuit diagram of heater resistance measurement engine 618 and power router 616 in accordance with one specific implementation. Thermocouple amplifier may convert thermocouple resistance received from heater resistance measurement engine 618 to temperature, with cold-junction compensation, and/or accept input from a thermistor, for example. More than one temperature input may be included. FIG. 9 depicts an example circuit diagram of thermocouple amplifier 608 and temperature reference engine 602 in accordance with one specific implementation. Additionally, communication engine 620 is connected to short protection engine 622 and data from communication engine 620 can be sent back to energy delivery console 104 via comm and power minus through communication engine 620. Accordingly, FIG. 10 depicts an example circuit diagram of communication engine 620 in accordance with one specific implementation. Heating catheter 102 may also have a memory module to store information such as device identification and operating parameters for energy delivery console 104, device-specific calibration information and past record of testing and/or product use. This memory module may also be integrated into a microprocessor, control engine, or CPU 600.

In a specific implementation, at least a portion of heating catheter 102 can be provided to the user sterile within a sterile barrier (e.g., Tyvek-Mylar pouch, permeable or impermeable pouch, or thermoformed tray with permeable membrane lid) package. In a further variation, a method such as Ethylene Oxide sterilization, Gamma-ray sterilization, E-beam sterilization, or Hydrogen Peroxide gas sterilization can comprise sterilizing heating catheter 102.

In a specific implementation, a sterile barrier package consists of a tube (e.g., high-density polyethylene (HDPE)) that is held in a coiled configuration with at least one end permitting heating catheter 102 to be introduced to the interior of the coil for protection. A component (e.g., a die-cut flat card, a thermoformed tray or clamshell, or a molded shape) can be configured to hold both the coil and the catheter handle and/or cable. The catheter handle may be configured to hold a portion of the coil.

In a specific implementation, an electrical connection between the heating catheter 102 and energy delivery console 104 can be made by plugging a long catheter cable (built as part of the disposable energy delivery catheter) directly into energy delivery console 104. Additionally, a user sterilizable multiple-use cable can connect between the handle of the energy delivery catheter and the energy delivery system. FIGS. 11A, 11B, and 11C illustrate console connector 1100, thermocouple connector 1102, and first and second heater connector 1104. In a specific implementation, the electrical connection can be made partway between heating catheter 102 and energy delivery console 104, for example 18" from edge of sterile operating table (with energy delivery catheter cable length of 24-36").

In a specific implementation, a push-to-engage type connector (such as a ¼" mono or tip, ring, and sleeve (TRS) stereo plug, card-edge connector or a LEMO®-style connector) can be used to connect the heating catheter and the energy delivery system. The electrical connection may be facilitated by being magnetically coupled. The electrical wiring of the energy delivery catheter can be bundled cable, twisted wire pairs or generally parallel monofilar or bifilar cables.

Figure 12:
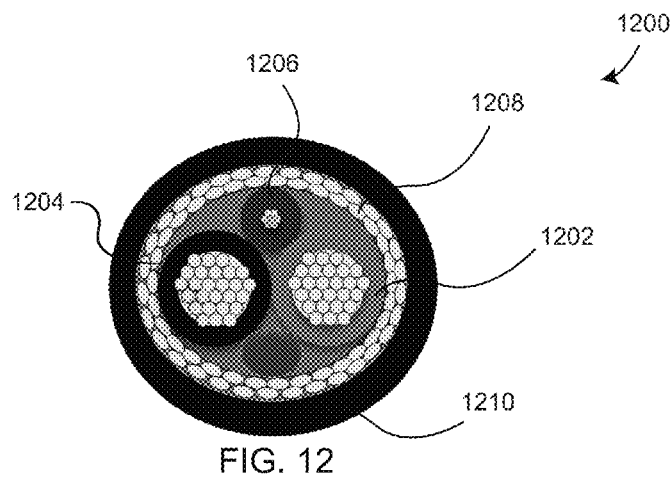
FIG. 12 depicts a diagram of an example communication wire connecting a heating catheter to an energy delivery console.

FIG. 12 depicts example cable configuration 1200 for power delivery and communication that may include a wire bundle with two 20 AWG (e.g., 26/0.16 BC) wires for power delivery 1202 (red) and common ground 1204 (e.g., PVC coated with red and black insulation, respectively) and a 30 AWG (e.g., 7/0.1 BC) communication wire 1206 for communication (e.g., PVC coated with blue insulation). Cable configuration 1200 can be provided heavily shielded with shield 1208, such as with a helically wrapped copper wire bundle (e.g., 72/0.102 BC), a braided wire shield, a conductive tape-wrapped shield, or the like. Size and gauge of the wires may be reduced or increased for other similar implementations. The overall cable is covered with jacket 1210 of PVC, thermoplastic elastomers (TPE), or similar non-conductive material.

Figure 13:
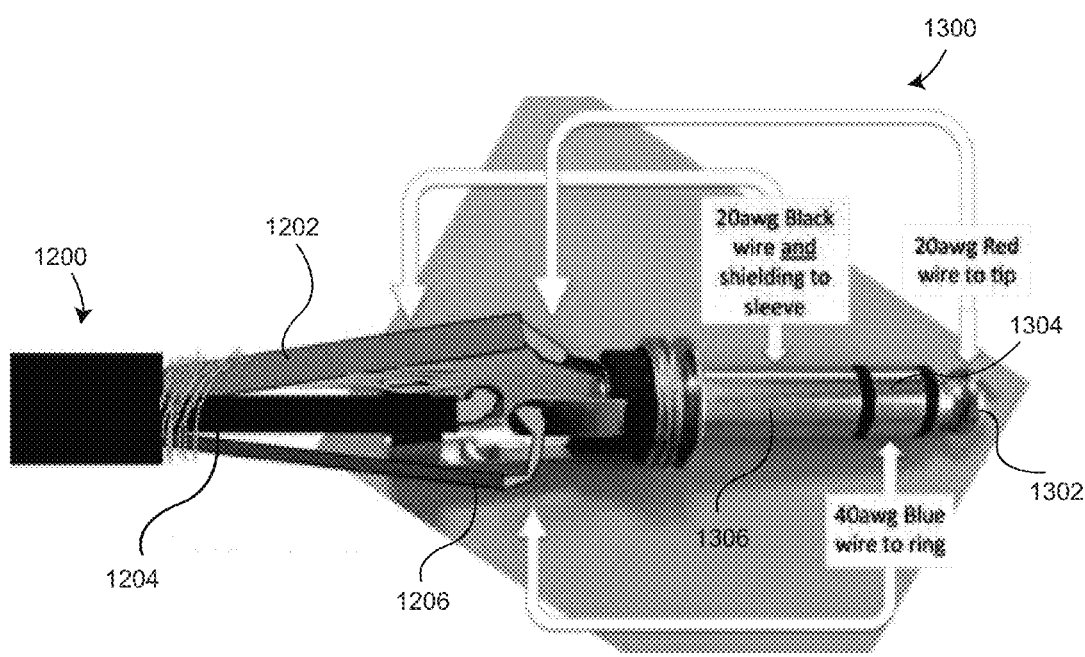
FIG. 13 depicts a diagram of an example tip, ring, and sleeve cable connection and wire that can be used to connect a heating catheter to an energy delivery console.

FIG. 13 depicts an example TRS plug 1300 that can be used, in a specific implementation, as the electrical connection between cable configuration 1200 (attached to heating catheter 102) and energy delivery console 104. In this example, TRS plug 1300 is a ¼" TRS stereo barrel plug with three conductors, tip 1302, ring 1304, and sleeve 1306. The four conductors (including shield 1208) of the cable are made to work with a 3-conductor TRS plug, such as TRS plug 1300, by connecting (red) power delivery 1202 wire to tip 1302, (blue) communication wire 1206 to ring 1304, and both (black) ground wire 1204 and shield 1208 to sleeve 1306.

Figure 14:
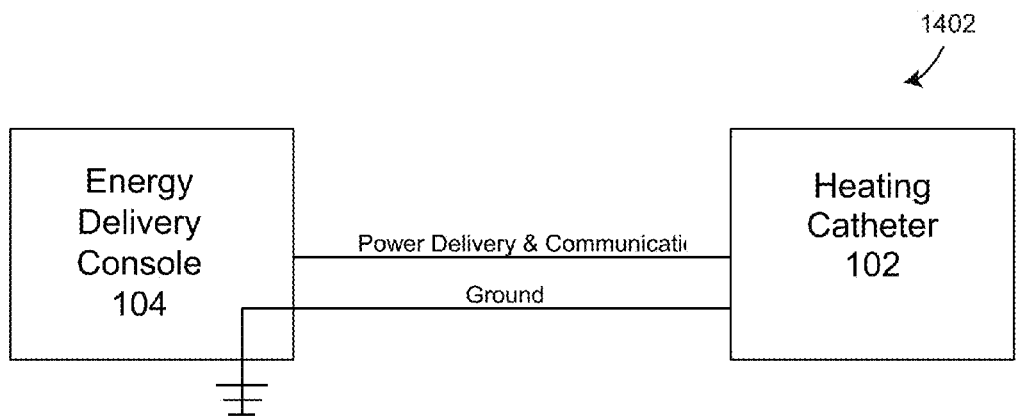
FIGS. 14A-14C depict example communication wire diagrams between a heating catheter and an energy delivery console.
Figure 14:
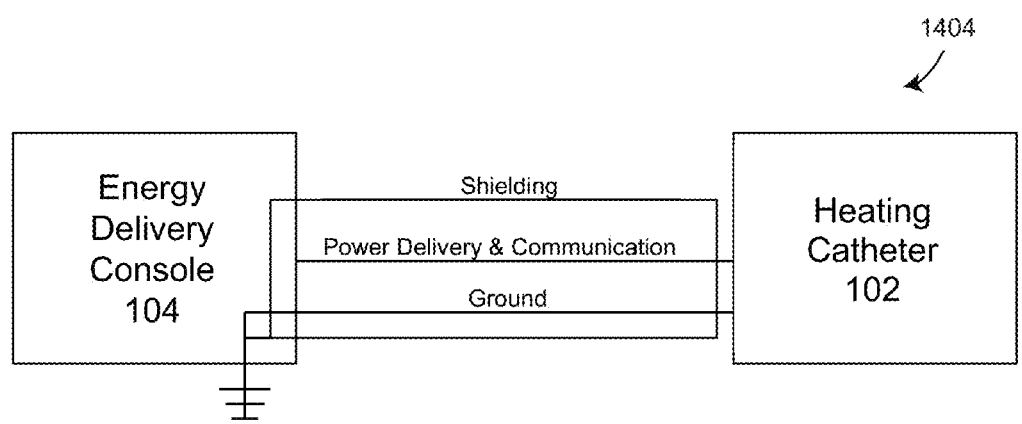
Figure 14:
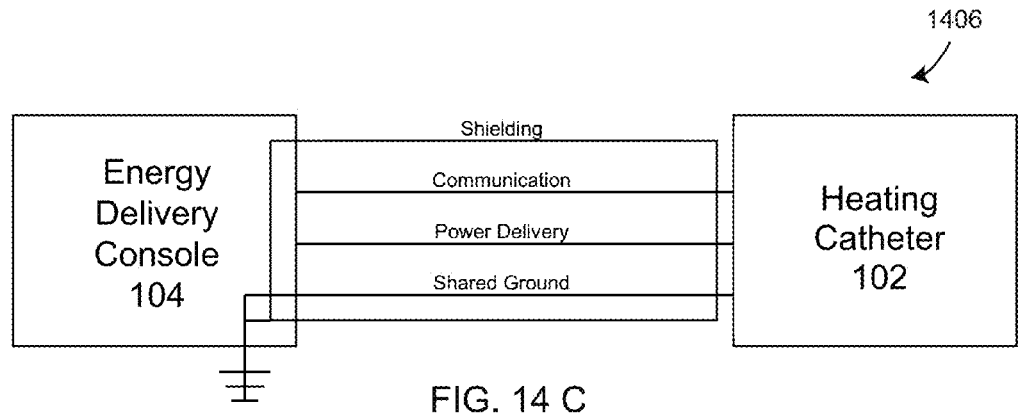

In a specific implementation, shield 1208 terminates near the handle of heating catheter 102 and is not connected in common with ground wire 1204 at the handle. This is shown as three possible configurations in FIGS. 14A-14C. Accordingly, FIG. 14A depicts first example wire configuration 1402 wherein a single wire provides both power delivery and communication to heating catheter 102 and a single ground wire serves as a ground and provides a return path for communication without any shielding. FIG. 14B depicts second example wire configuration 1404 wherein a single wire provides both power delivery and communication to heating catheter 102 and a single ground wire serves as a ground and provides a return path for communication with shielding. FIG. 14C depicts third example wire configuration 1406 wherein separate wires provide power delivery and communication to heating catheter 102 and both wires share the same ground wire return path with shielding.

Thus, in a specific implementation, as few as two wires extend between the heating catheter 102 and energy delivery console 104. The two wires are used to deliver energy, and also to convey a data signal (e.g., within a high frequency range) such as serial communication that is filtered out using, for example, a low-pass filter, before the energy conducts to the heating element. Heating catheter 102 may include a momentary switch such as to provide a start/stop signal for heating. There may be a provision for one or more light emitting diode (LED) lights on the energy delivery catheter, such as approximately adjacent to one or both ends of heating element 106, or configured to illuminate through heating element 106, or located within the catheter handle. In one example, the LED lights blink in a pattern that makes it easier for the user to distinguish the LED light from background light.

There may also be one or more Piezo ultrasonic crystals on heating catheter 102, such as approximately adjacent to one or both ends of heating element 106, configured to broadcast a signal that will be distinct within the ultrasound field of visualization in B-mode or color Doppler. There may be a use-control engine that determines if energy delivery console 104 has been used in a recognized procedure and prevents further use after a specified condition such as number of treatments and/or elapsed time after first clinical use.

In a specific implementation, an instruction set (e.g., software) can exist to recognize heating catheter 102 and apply a corresponding instruction set to manage heating control and information display. The instruction set can observe if a button has been pressed on the energy delivery catheter and then initiate or terminate energy delivery. Energy can automatically be terminated after a predetermined treatment time, delivery of a desired total or minimum amount of power, or a combination of the two requirements.

In a specific implementation, an energy delivery console 104 comprises a power source and measuring devices. One measuring device can be a Wheatstone bridge, suitable for measuring temperature via a thermocouple. Another measuring device can be a thermistor. Another measuring device can be an Ohmmeter or similar means for measuring resistance or impedance of the heating element circuit of heating catheter 102. Another measuring device can be an Ammeter or similar means for measuring or determining electrical current delivered to the heating element circuit of heating catheter 102. Another measuring device can be configured to interact with a serial communications element of the energy delivery catheter (e.g., 1-WIRE® chip or radio-frequency identification (RFID) device).

In a specific implementation, an energy delivery console 104 communicates with the energy delivery catheter with minimal conductive wires between them. For example, a serial communication protocol over a pair of wires such that the pair of wires can be used to deliver energy to heating catheter 102 (perhaps stored or regulated in a capacitor built into heating catheter 102 handle or cable, or with a signal from heating catheter 102 alerting energy delivery console 104 when to send power and what the voltage and current should be) as well as to provide catheter identification data and temperature and/or resistance/impedance feedback.

In a specific implementation, the energy delivered to accomplish heating of the heating element may be delivered in a series of pulses similar to pulse width modulation, but with the pulses configured into a serial communication protocol to accomplish two-way communication. In one example, a third wire is configured for communication from the energy delivery catheter to the energy delivery console 104. In one example, a thermistor or thermistors are used at the heating element of heating catheter 102 to simplify the measurement of temperature and allow such data to be sent to the energy delivery console 104. In an alternative example, a thermocouple or thermocouples are used at the heating element and a cold junction thermocouple and Wheatstone bridge or similar compensation are used within the catheter handle to determine temperature measurement and allow such data to be sent to the energy delivery console 104.

In an exemplary use case, upon plug-in of heating catheter 102 into energy delivery console 104 a low-current test voltage within a limited frequency range is applied to heating catheter 102 and filtered with a low-pass or high-pass filter so that no therapeutic level of energy is delivered to heating element 106. A communication handshake can be established between heating catheter 102 and energy delivery console 104, and heating catheter 102 may transmit an identifier to energy delivery console 104 that allows energy delivery console 104 to recognize heating catheter 102 and associate the correct instruction set to manage energy delivery console 104. Heating catheter 102 may also transmit a quality check status that ensures that heating catheter 102 is an authentic product, functioning properly, and ready for treatment.

Heating catheter 102 may transmit measured temperature of heating element 106, at intervals such as ten to 100 times per second (10-100 Hz). Heating catheter 102 transmits status of start/stop instruction, as when a user presses a button on the catheter handle to initiate treatment. When the start/stop instruction is that a button has been pressed to initiate treatment, heating catheter 102 may send an instruction to energy delivery console 104 indicating that treatment should begin and energy delivery console 104 begins to send power at an appropriate Voltage and/or duty cycle for the active heating length of heating catheter 102 and at a current sufficient to achieve and maintain a target treatment temperature, using the relayed temperature or thermocouple resistance from heating catheter 102 to guide the treatment. Energy delivery console 104 may display the measured temperature, the level of energy being delivered and the remaining treatment time.

If heating catheter 102 has user-selectable active heating element zones (e.g., the full length of heating element 106 or the distal 25% or 10% of heating element 106) then energy delivery console 104 may communicate to heating catheter 102 that the delivered power should be routed to the appropriate wires to accomplish that heating length. A screen of energy delivery console 104 may also indicate an image identifying what portion of heating catheter 102 will heat or is heating. Voltage may be stored (e.g. in a capacitor) and/or stepped up or down to provide sufficient voltage for the logic portion of heating catheter 102 (e.g., 3 V) separate from the delivered voltage for the active heating element length (e.g., 24 V for 10 cm heating length, 6 V or 9 V for 2.5 cm, 2.4 V, 6 V or 9 V for 1 cm). Alternatively, the logic portion of heating catheter 102 may be powered by a battery (e.g., CR2032 button cell, AAA, or other battery) within the handle. In one example the two wires in heating catheter 102 cable may be a twisted or substantially parallel pair (e.g., 16-24 AWG, more preferably 18-22 AWG, preferably stranded for flexibility) that is shielded within the cable. The connector for a two- or three-wire catheter cable may be a coaxial design such as a coaxial power plug (as commonly used to plug in the power cable to a laptop computer), a coaxial plug (e.g., TRS or TR) such as used for headphones and/or microphones, or other connector such as 2-3 banana plug connectors or card-edge connectors.

In a specific implementation, one or more charge pumps are used within the catheter handle in order to increase the voltage to transistors (e.g., MOSFETs) that connect the heating elements to the power delivery circuitry. The charge pumps are used to overcome the natural decrease in resistance over time that results from battery use.

As discussed above, an exemplary three-conductor connector used to plug heating catheter 102 into energy delivery console 104 is a 6.35 mm stereo TRS audio plug with three conductors. The tip may provide the power, the ring may provide communication link and the sleeve may be a common return to ground. This system is shielded from the user so that only the ground may be contacted by the user's hand when the tip first contacts the power source. In a further implementation, a switch is configured to allow power connection to the 6.35 mm connector jack only when the plug is physically pushed into the jack such that the tip does not short across the tip and ring terminals inside the connector jack. This switch may be configured inside the jack so that the tip of the plug pushes the switch to engage, or it may be configured externally so that the body of the 6.35 mm plug handle pushes the switch to engage. In a further implementation, the circuitry connected to the TRS connector plug and/or jack includes one or more diodes in an arrangement to prevent shorting between the tip and ring contacts from damaging the catheter or energy delivery device. In a further implementation, the circuitry connected to the TRS connector plug and/or jack includes one or more fuses in an arrangement to prevent shorting between the tip and ring contacts from damaging the energy delivery device or from causing apparent physical damage to the catheter.

In a specific implementation, a separate component sterile sleeve, similar to a sterile ultrasound probe cover, can be designed to interact with the handle/cable connection providing easy means of unfurling the sterile sleeve to cover the multi-use cable. One example way to ease unfurling of the sterile sleeve is to build in a rigid or semi rigid frame that is attached to the end of the sleeve that will be extended forward to cover the desired length of cable and render the surface sterile. This same frame can be used to stretch the sleeve material taut (like a drum head) at the end that will interface with the heating catheter handle to allow for a fluid-tight seal. One way to achieve such a seal is for the handle to pierce the sleeve material and then force it open via a tapered interface shape that seals against the sleeve material.

Alternatively, the sleeve material can have a shaped opening that is smaller than a tapered entry point on the catheter handle but that also forces it to stretch open and provide a seal against the handle. In one embodiment, a frame is provided that can be used with a commercially-available ultrasound probe cover to provide a means for easy connection and unfurling as described above. In all cases where a sterile sleeve is used, the length of the sterile sleeve should be at least sufficient to cover the cable to the edge of the sterile field, e.g., approximately 30-60 cm.

In a specific implementation, a multi-use cable is configured to include a radio-frequency (RF) antenna that is capable of sensing an RFID tag embedded in the catheter near the point of connection between the catheter and the cable. In a further example the cable includes a handle with associated electronics such as a switch, and the RF antenna is located within the handle so that when a connector to a catheter is plugged into the handle the RF antenna can read and interact with the RFID tag that is part of the catheter. This RFID tag can be used to identify the device, apply associated parameters from the energy console, and even store data including ongoing history of device use.

In a specific implementation, an alternative way to connect heating catheter 102 to energy delivery console 104 is to use inductive coupling to power heating catheter 102 across a sterile barrier, so that no puncture of the barrier is necessary. This can be done to provide power to an energy delivery system if that system is placed within the sterile field (such as within a sterile envelope) or if can be done between energy delivery console 104 and heating catheter 102. Communication between energy delivery console 104 and heating catheter 102, such as for catheter identification, temperature feedback, and device start/stop commands, can be done via wireless protocol, such as Wi-Fi, BLUETOOTH®, or ZIGBEE®.

In a specific implementation, an energy delivery system can be a table-top console designed to be located out of the sterile field in a location that is visible to all participants in the procedure that have a need to see the displayed data or will physically interact with the system (such as plugging in the energy delivery catheter). It can also be beneficial for the system to be located near a fluid delivery pump for the local anesthetic solution and/or an ultrasound console or display screen.

Figure 15:
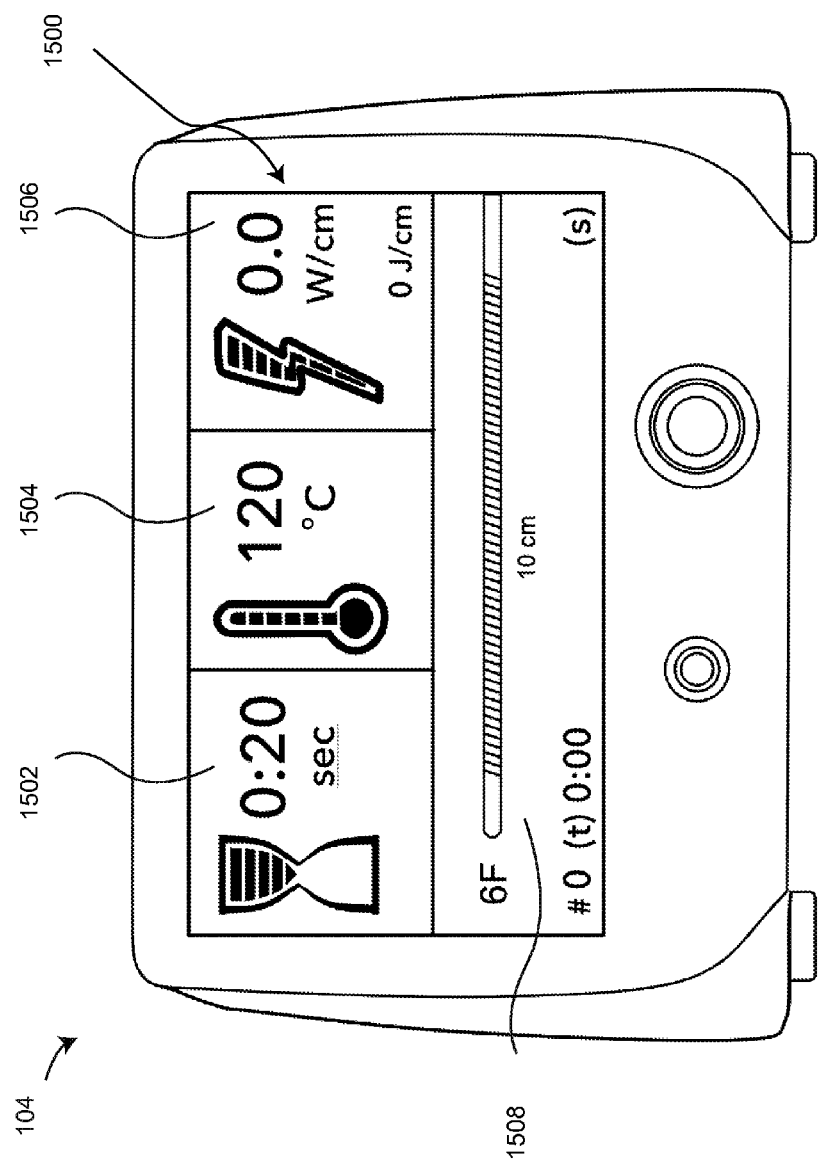
FIG. 15 depicts an example diagram of an example energy delivery console.

FIG. 15 depicts an example diagram of an example energy delivery console 104. In a specific implementation, energy delivery console 104 can be located directly adjacent to the sterile field (such as placed on a pole stand with a boom arm to hold the unit nearly above the sterile field) or directly within the sterile field (such as if placed within a sterile envelope such as a see-through bag, or if the system and a power supply is configured to withstand sterilization such as by steam). Information can be provided to a user of energy delivery console 104 on display screen 1500 (e.g., LCD, LED, flat-panel, touchscreen), by indicators (e.g., lights and/or sounds), or by interacting with a remote device such as a cell phone, tablet or computer. Exemplary information provided to a user may include power level 1506 being delivered (e.g., instantaneous power in W or W/cm and/or cumulative power in Joules or J/cm), measured temperature 1504 (e.g., ° C.), timer 1502 (e.g., countdown or countup, seconds), alerts or status messages, identification information 1508 of a connected heating catheter 102, history of earlier treatments, system and/or catheter settings, software revision of energy delivery system and copyright information. Multiple languages and date/time formats can be supported, as selectable by the user as well.

In a specific implementation, energy delivery console 104 can be powered by facility power (e.g., wall outlet in the range of 110-240 V AC), with a voltage regulator either built within the system or configured into the power cord (e.g., corded power supply system accepting 110-240 V AC as input and providing 24 V DC as output). Additionally, energy delivery console 104 can be battery-powered. Two or more power modules can be incorporated into the energy delivery console 104 in order to supply appropriate voltage for the microcontroller (e.g., 6-20 V, or 7 12 V) and the energy delivery voltages (e.g., 12-24 V and 1-5 V, or 18-24 V and 1.8-3 V). In a specific implementation, the energy delivery console 104 is powered by facility power (e.g., 110-112 V or 220-240 V) and a microprocessor within heating catheter 102 is powered by a battery (e.g., 5 V). In a further implementation the battery inside heating catheter 102 has a pull-tab that interrupts power until it is pulled away by the user. In a further implementation the pull-tab is attached to heating catheter 102 packaging so that when the user removes heating catheter 102 from the packaging the pull-tab pulls away automatically.

Figure 16:
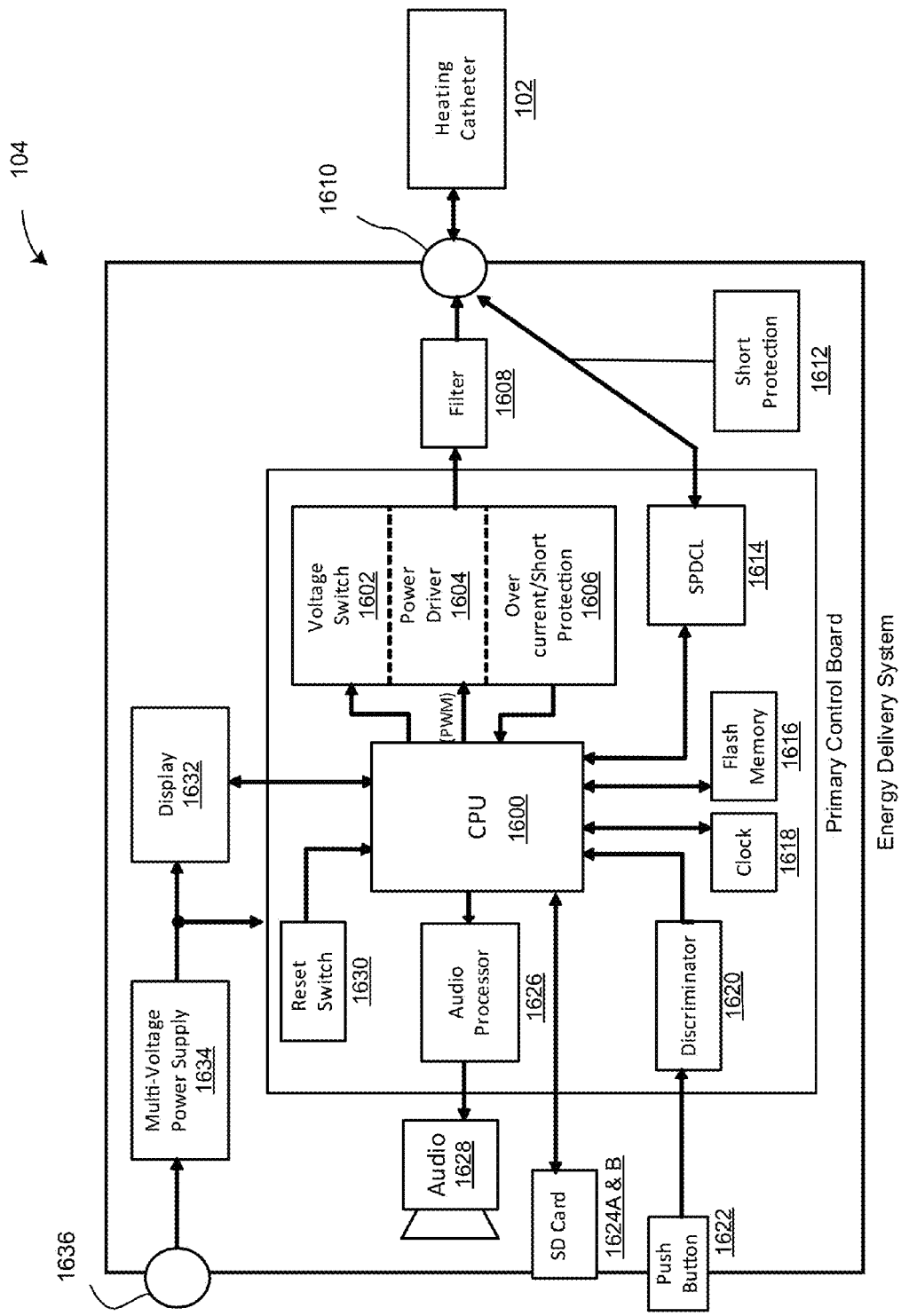
FIG. 16 depicts an example block diagram of an energy delivery console.
Figure 17:
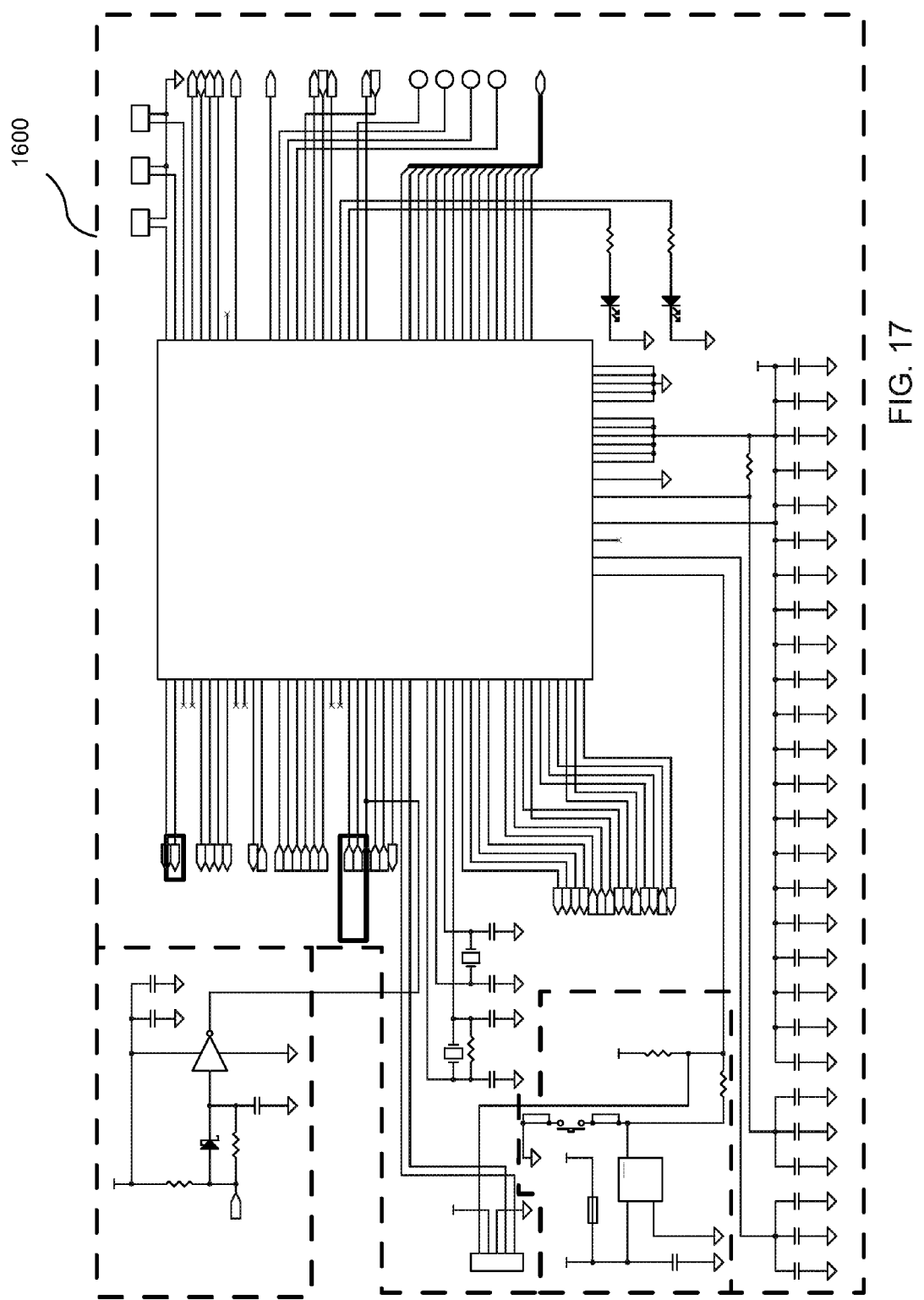
FIG. 17 depicts a diagram of an example central processing unit for an energy delivery console.
Figure 18:
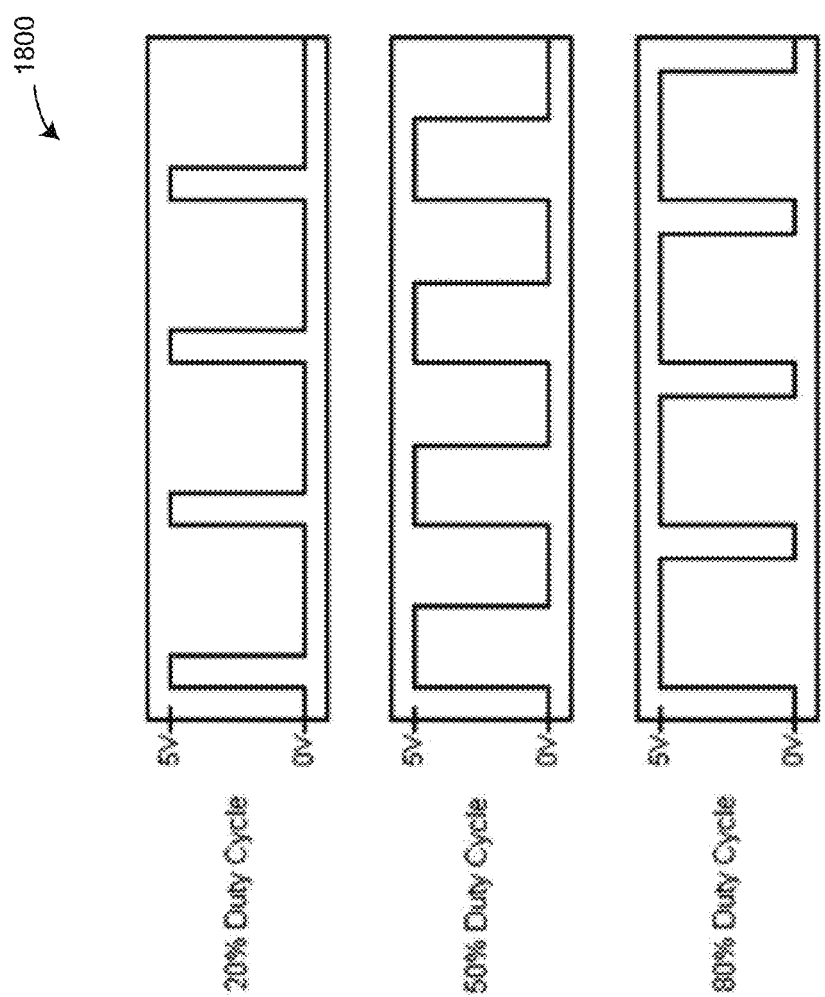
FIG. 18 depicts example pulse period lengths provided to a power driver from the CPU.
Figure 22:
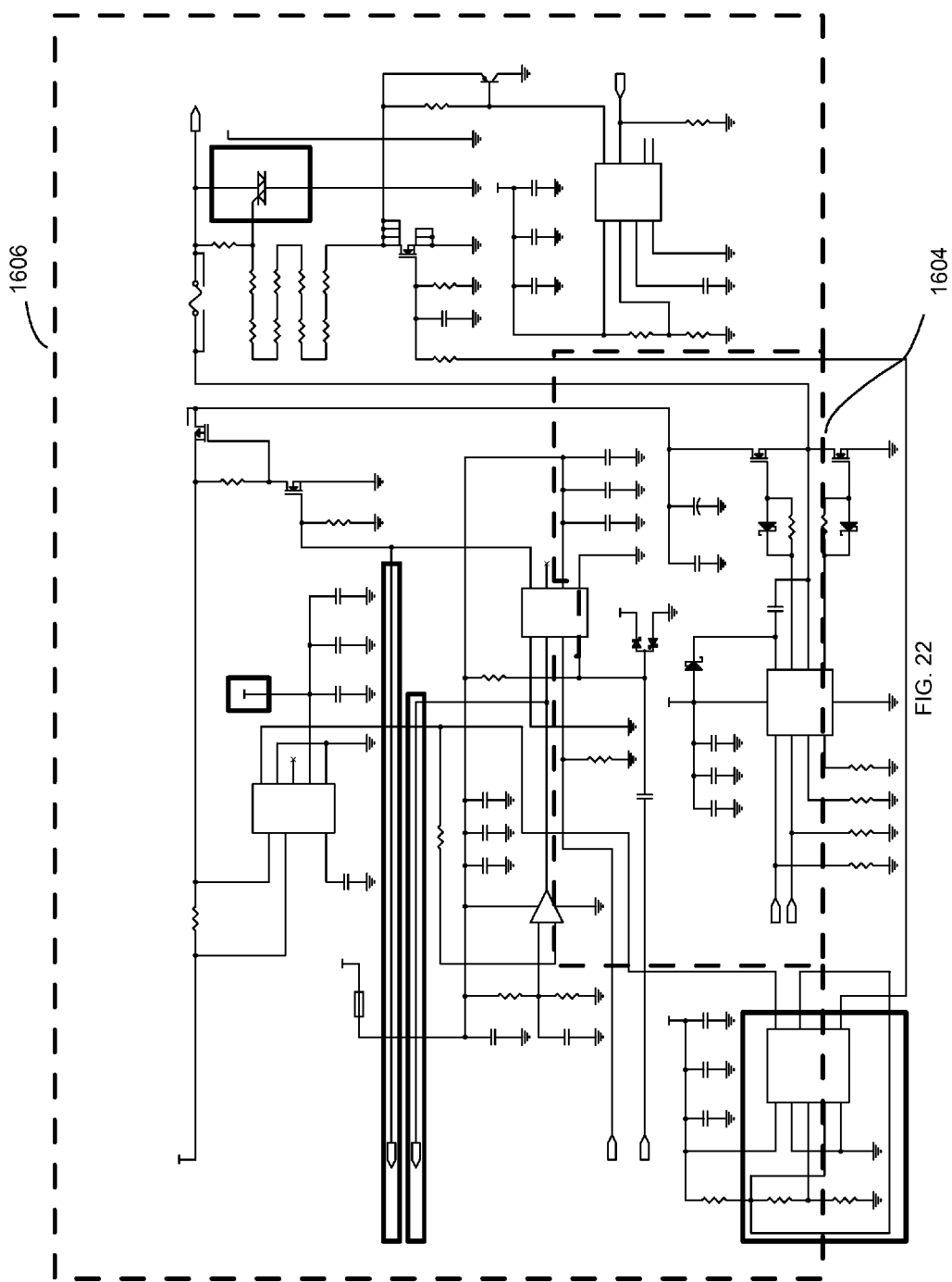
FIG. 22 depicts an example power driver and short protection engine for an energy delivery console.
Figure 23:
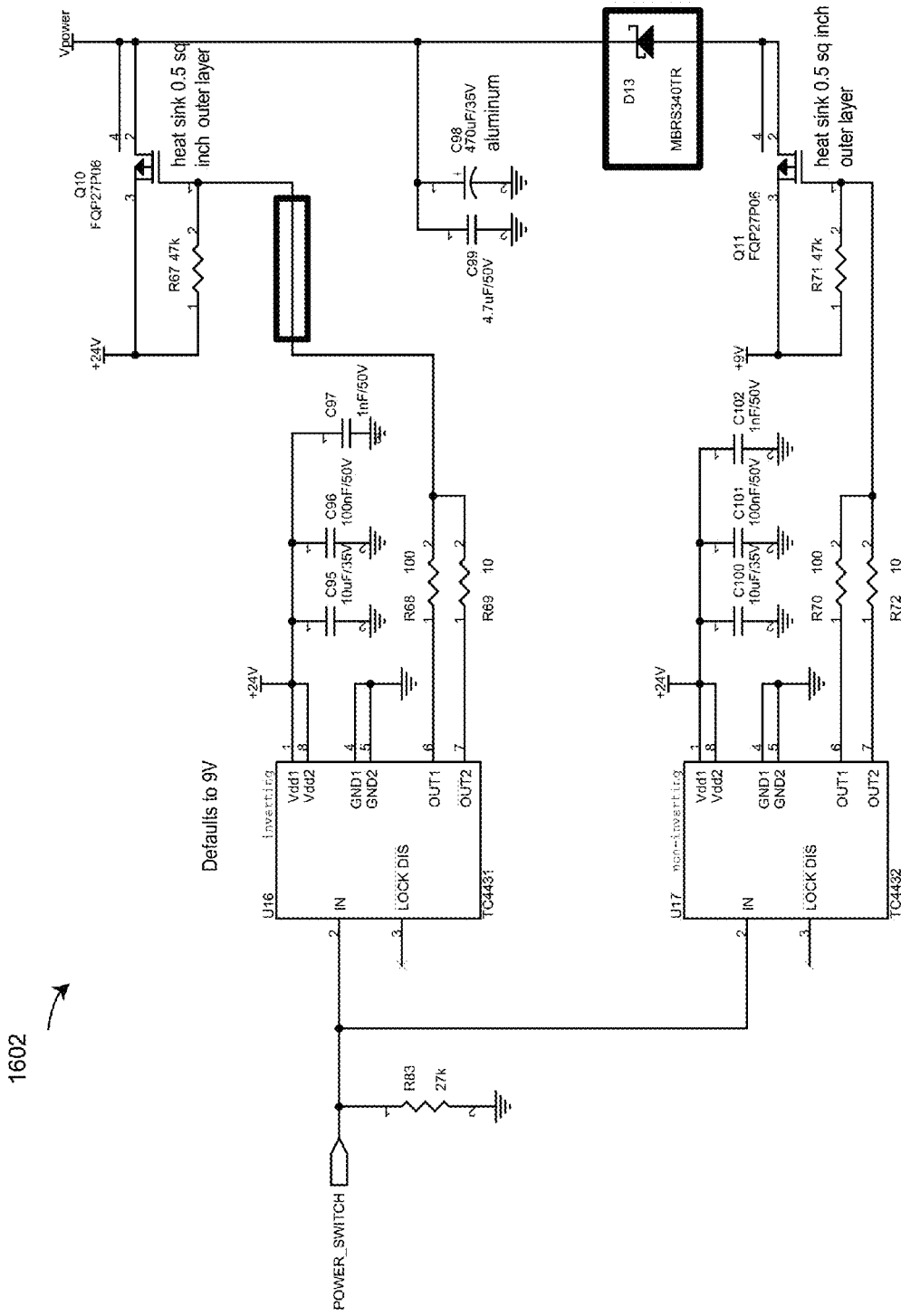
FIG. 23 depicts an example power switch engine for an energy delivery console.

FIG. 16 depicts an example block diagram of energy delivery console 104. In this example, console CPU 1600 is coupled to voltage switch 1602, power driver 1604, and over current and short protection 1606. FIG. 17 depicts a diagram of console CPU 1600 that can be used in energy delivery console 104. FIG. 22 depicts an example circuit diagram for power driver 1604 and over current and short protection engine 1606 and FIG. 23 depicts an example circuit diagram for power switch engine 1602 that can be used in energy delivery console 104. In a specific implementation, control of the strength of energy provided to the energy delivery catheter can be achieved through amplitude modulation or pulse width modulation (PWM) of the power signal from CPU 1600 to power driver 1604. FIG. 18 depicts example pulse period lengths provided to power driver 1604 from CPU 1600. In this example, pulse period may be constant or variable. Severity of applied energy may be modulated by duty cycle. Pulse amplitude may be constant (e.g., 24 V) or dependent on heating length of element (e.g., 24 V for 10 cm, 9 V for 2.5 cm or 3 V for 1 cm).

In the case of a serial communications protocol within the power cycling, switching between heating element wires to activate a desired heating length may be accomplished within the heat delivery catheter (such as in the handle) based on the power level delivered (pulse amplitude), or based on a keyed pulse or pulses of energy delivery that encodes device identification. Amplitude modulation can, for example, be for an electromagnetic wavelength in the radiofrequency range. PWM can also use a variety of pulse widths in the radiofrequency range.

Figure 30:
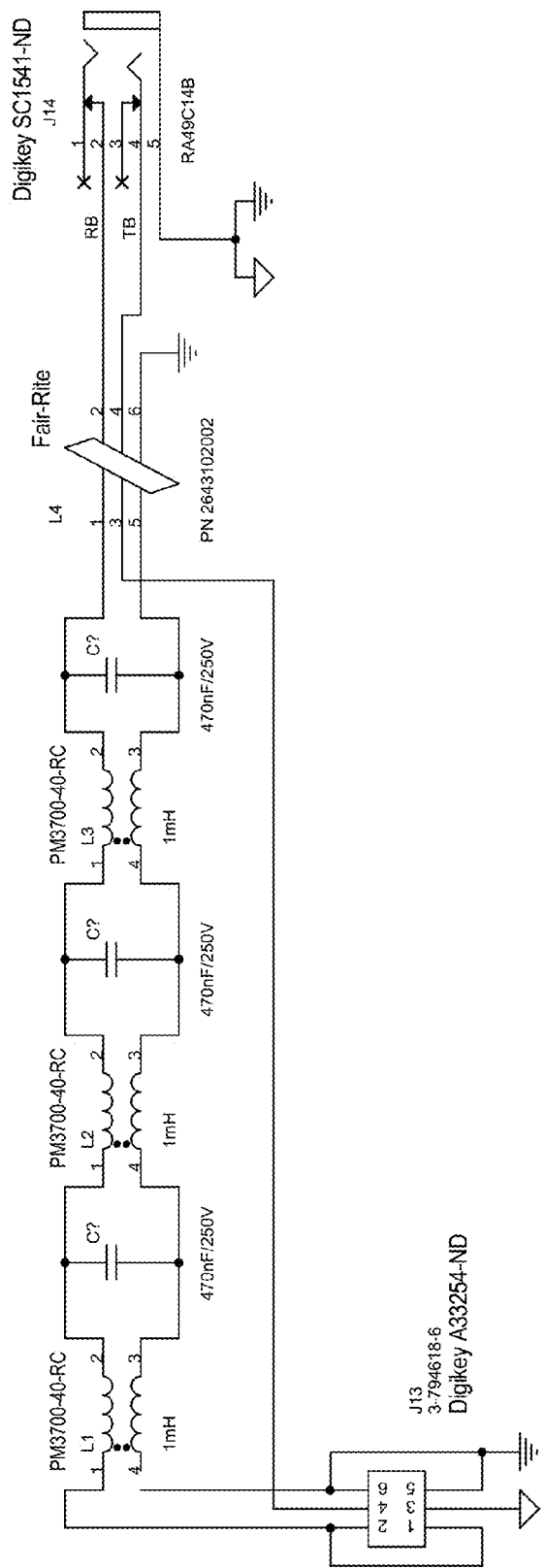
FIG. 30 depicts an example electromagnetic interference (EMI) filter that can be used with an energy delivery console.

Accordingly, a signal being sent from CPU 1600 to heating catheter 102 may pass through power driver 1604 to EMI filter 1608 before reaching connection 1610, which corresponds to a cable connecting heating catheter 102. FIG. 30 depicts an example diagram of EMI filter 1608 that can be used with energy delivery console 104 to filter out electromagnetic interference from other components and the like. Thus, signals are sent out of and received by energy delivery console 104 via Shared Power Delivery and Communication Legitimizer (SPDCL) 1614.

Figure 19:
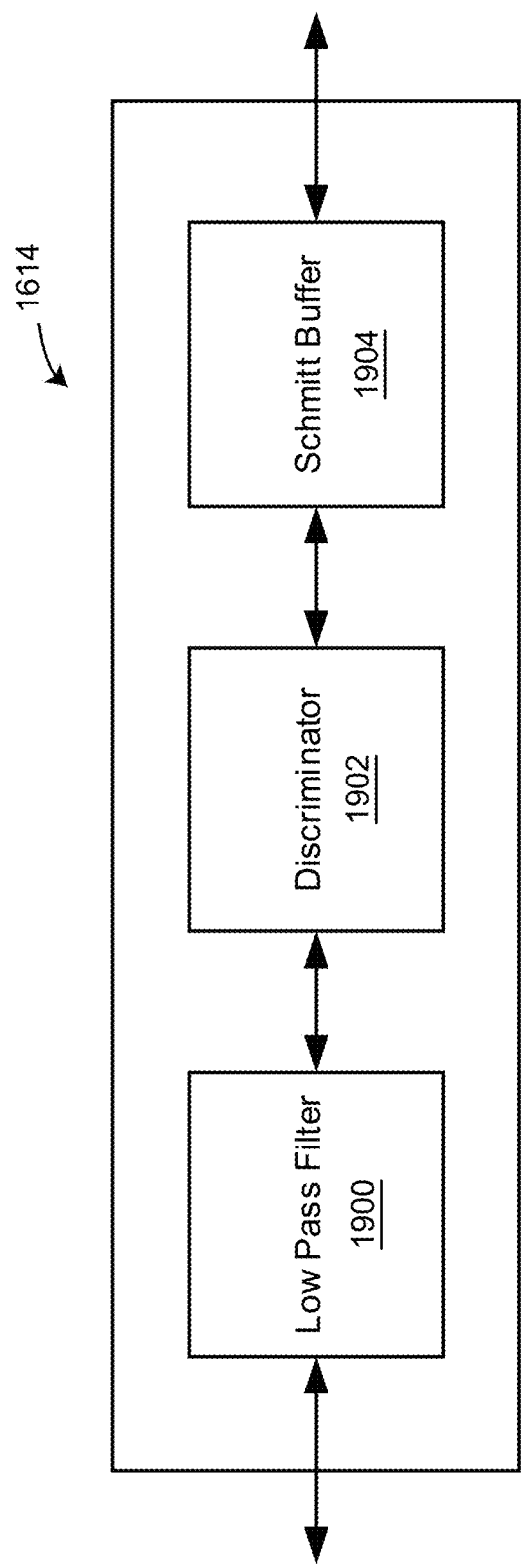
FIG. 19 depicts a diagram of an example low pass filter, discriminator, and Schmitt buffer of the shared power delivery and communication legitimizer.
Figure 20:
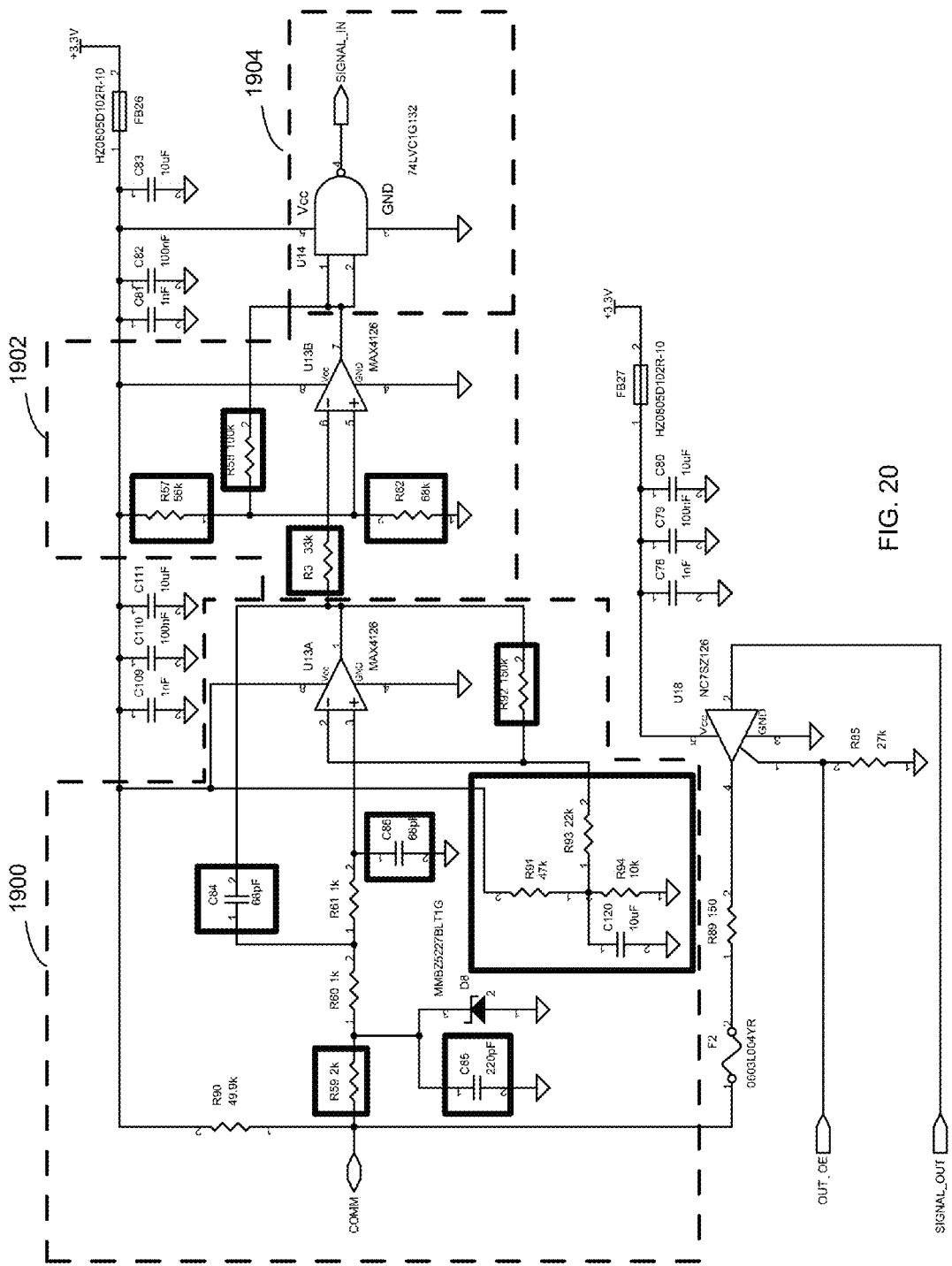
FIG. 20 depicts a diagram of an example of a shared power delivery and communication legitimizer.
Figure 21:
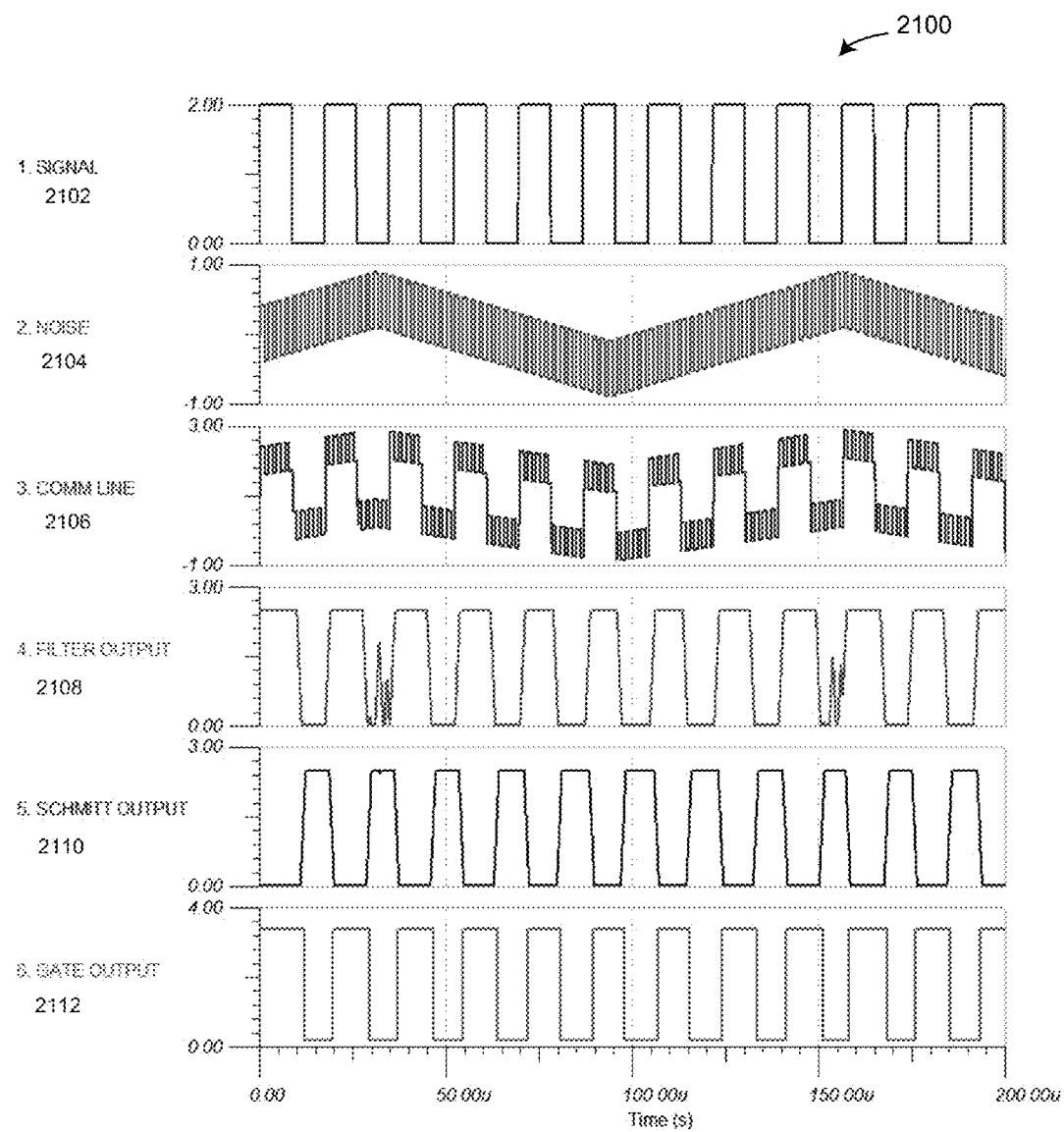
FIG. 21 depicts example steps for filtering a data signal being sent over a shared power delivery and communication ground.

In this example, console CPU 1600 is coupled to SPDCL 1614 that receives communication data from heating catheter 102. In this example, since wire configuration 1200 utilizes a shared ground and communication data return wire, SPDCL 1614 must filter out noise caused by sharing the return wire with the power delivery wire. Accordingly, FIG. 19 depicts an example block diagram of SPDCL 1614. In this example, SPDCL 1614 includes low pass filter 1900, discriminator 1902, and Schmitt buffer 1904. Additionally, FIG. 20 depicts a circuit diagram including low pass filter 1900, discriminator 1902, and Schmitt buffer 1904 of SPDCL 1614. Accordingly, FIG. 21 depicts example steps that SPDCL 1614 may take to filter a data signal being sent over a shared power delivery and communication ground wire. In this example, FIG. 21 shows signal 2102 and noise 2104 created by sharing the power delivery and communication return with the same ground. Accordingly, FIG. 21 shows comm line 2106 and filter output 2108, and Schmitt output 2110 for comm line 2106 to produce gate output 2112. Thus, SPDCL 1614 filters out noise that degrades the communication signal being sent from heating catheter 102 as this signal travels down the multi-use cable, described above, on its way to energy delivery console 104.

In a specific implementation, an arrangement of circuits and components is provided within energy delivery console 104 very near to the catheter plug-in jack connection 1610 in order to filter out noise within the system to provide clean power and clear and confident communication between heating catheter 102 and energy delivery console 104.

Figure 24:
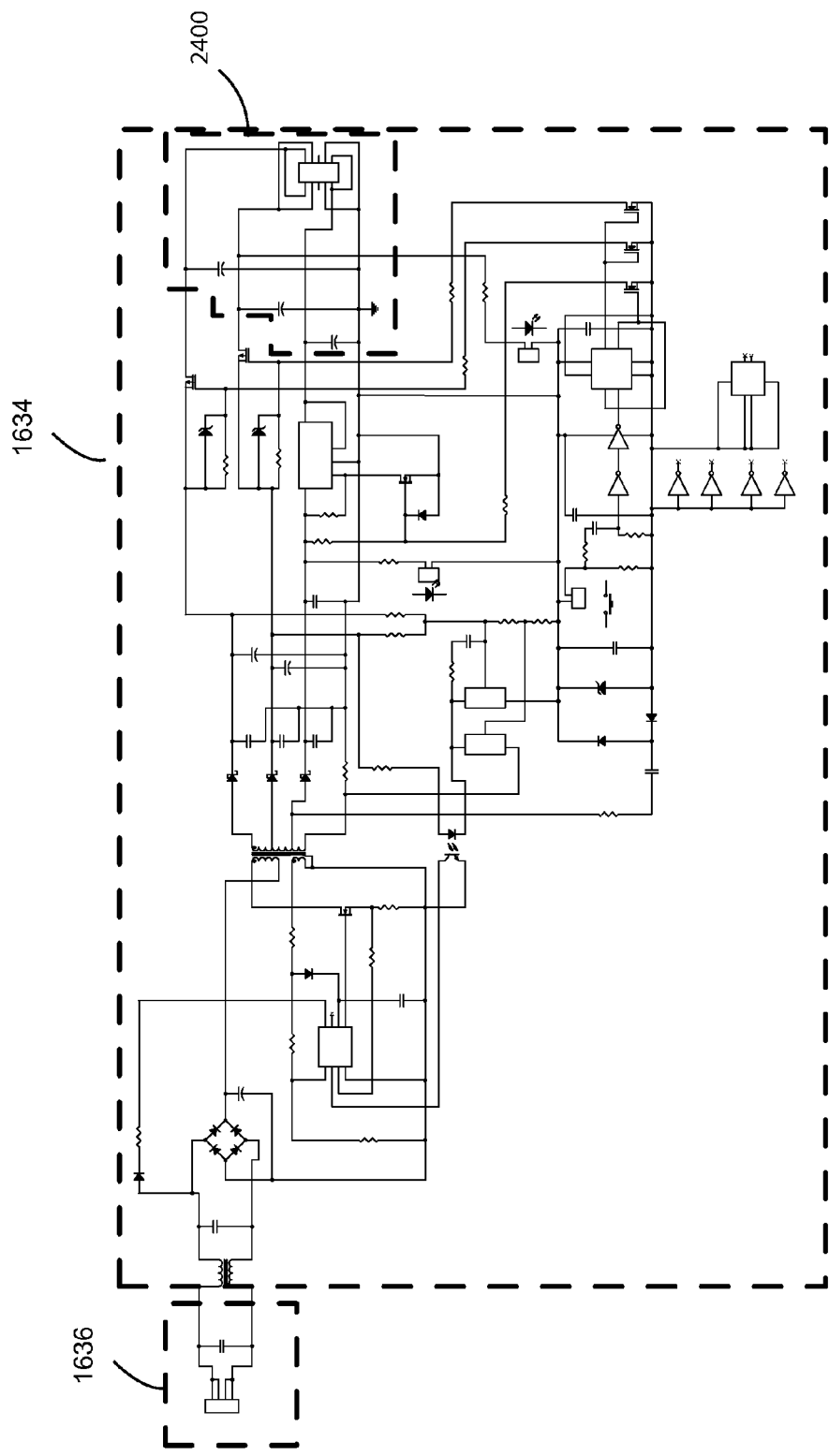
FIG. 24 depicts an example multi-voltage power supply that can be used by an energy delivery console.
Figure 25:
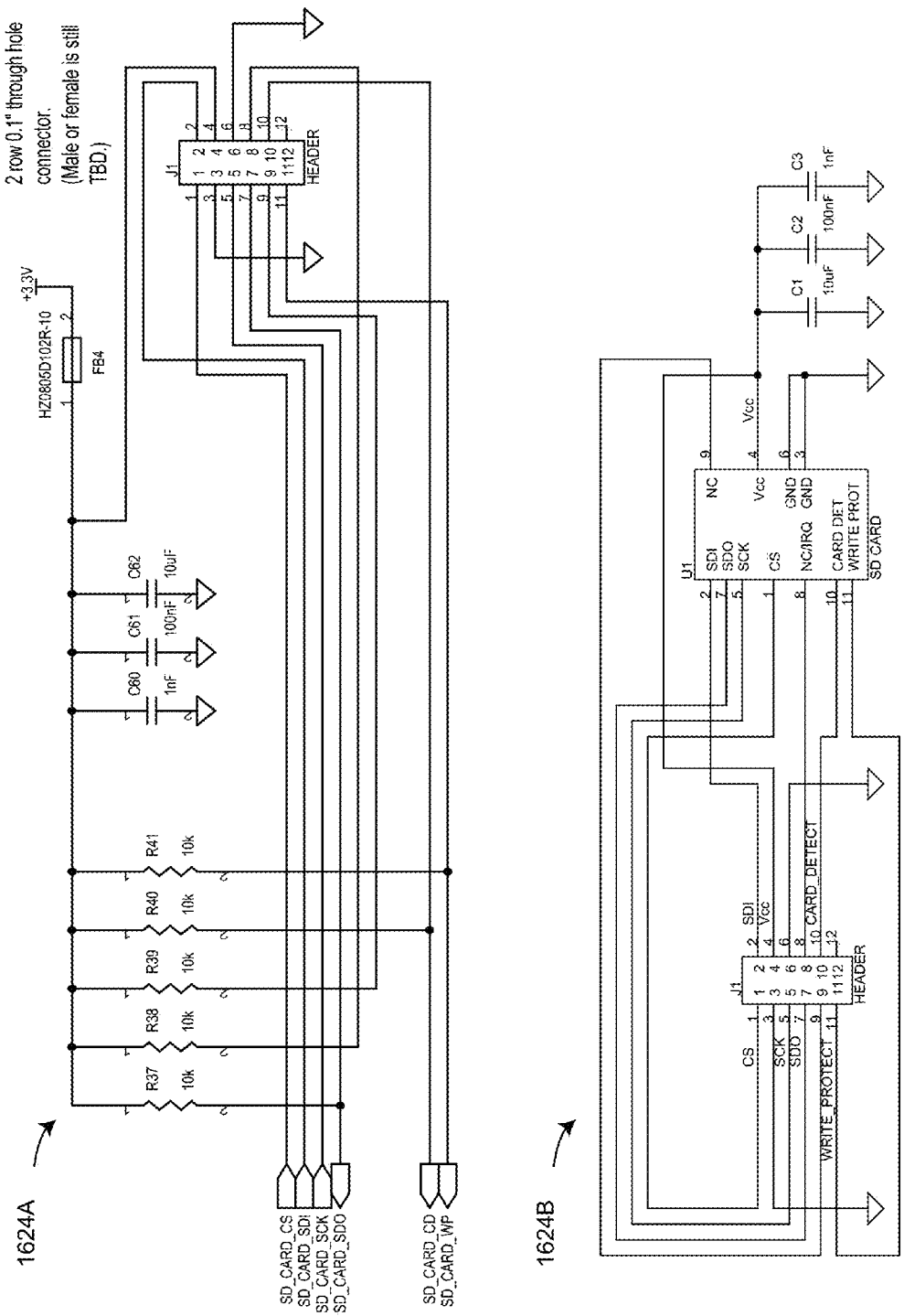
FIG. 25 depicts example secure digital (SD) cards that can be used with an energy delivery console.
Figure 26:
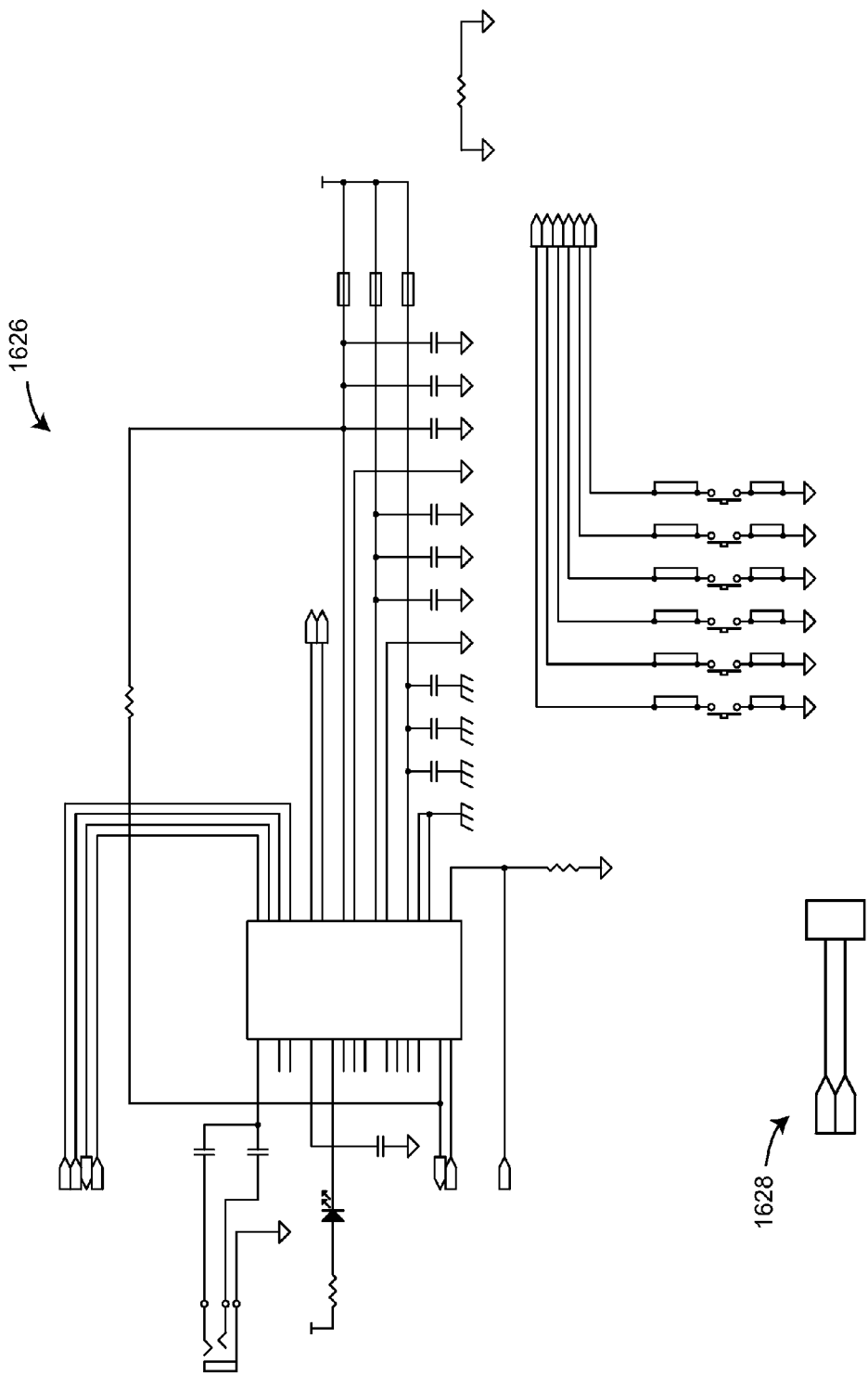
FIG. 26 depicts an example sound processor and audio output that can be used with an energy delivery console.
Figure 27:
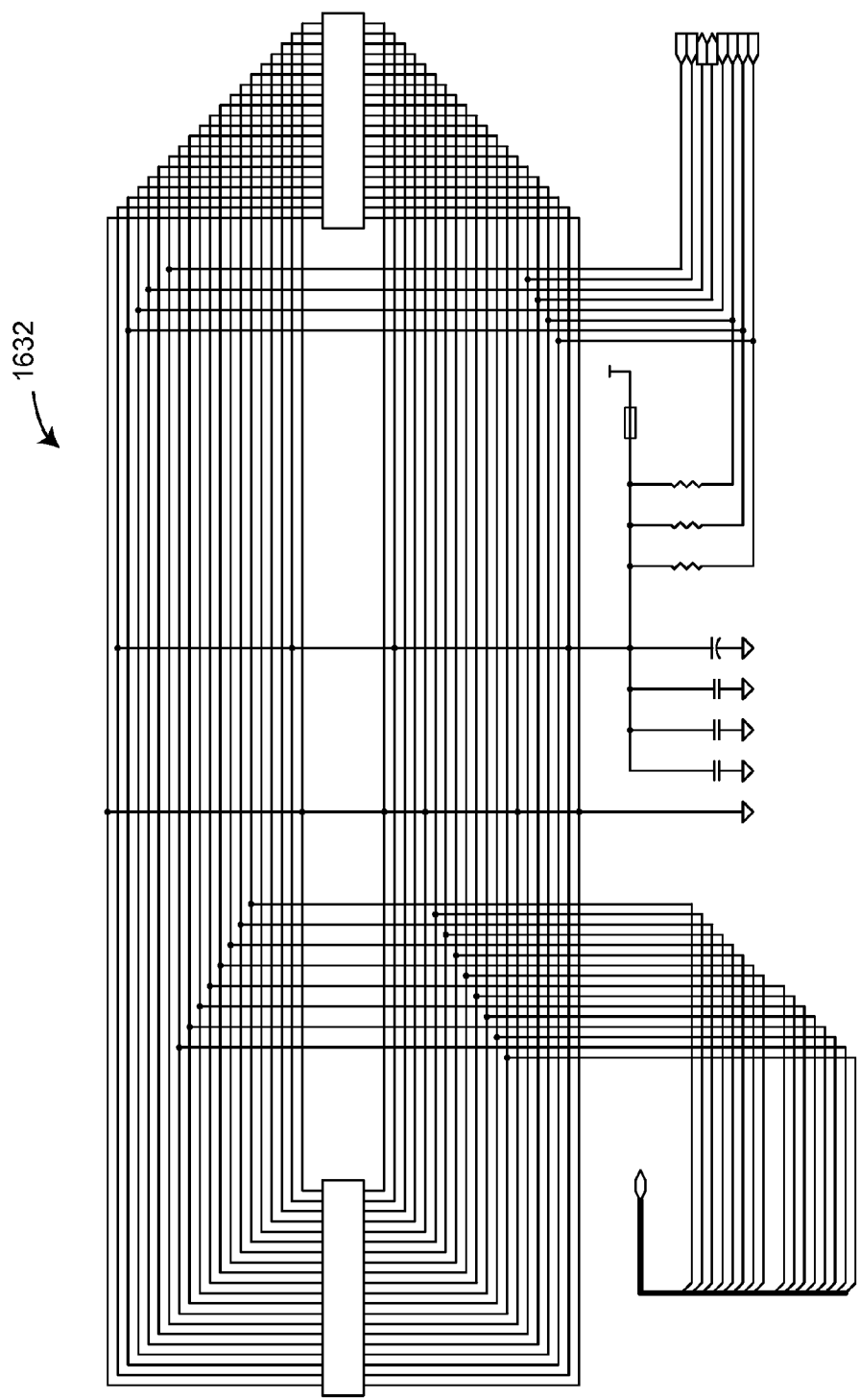
FIG. 27 depicts an example touch screen display that can be used with an energy delivery console.
Figure 28:
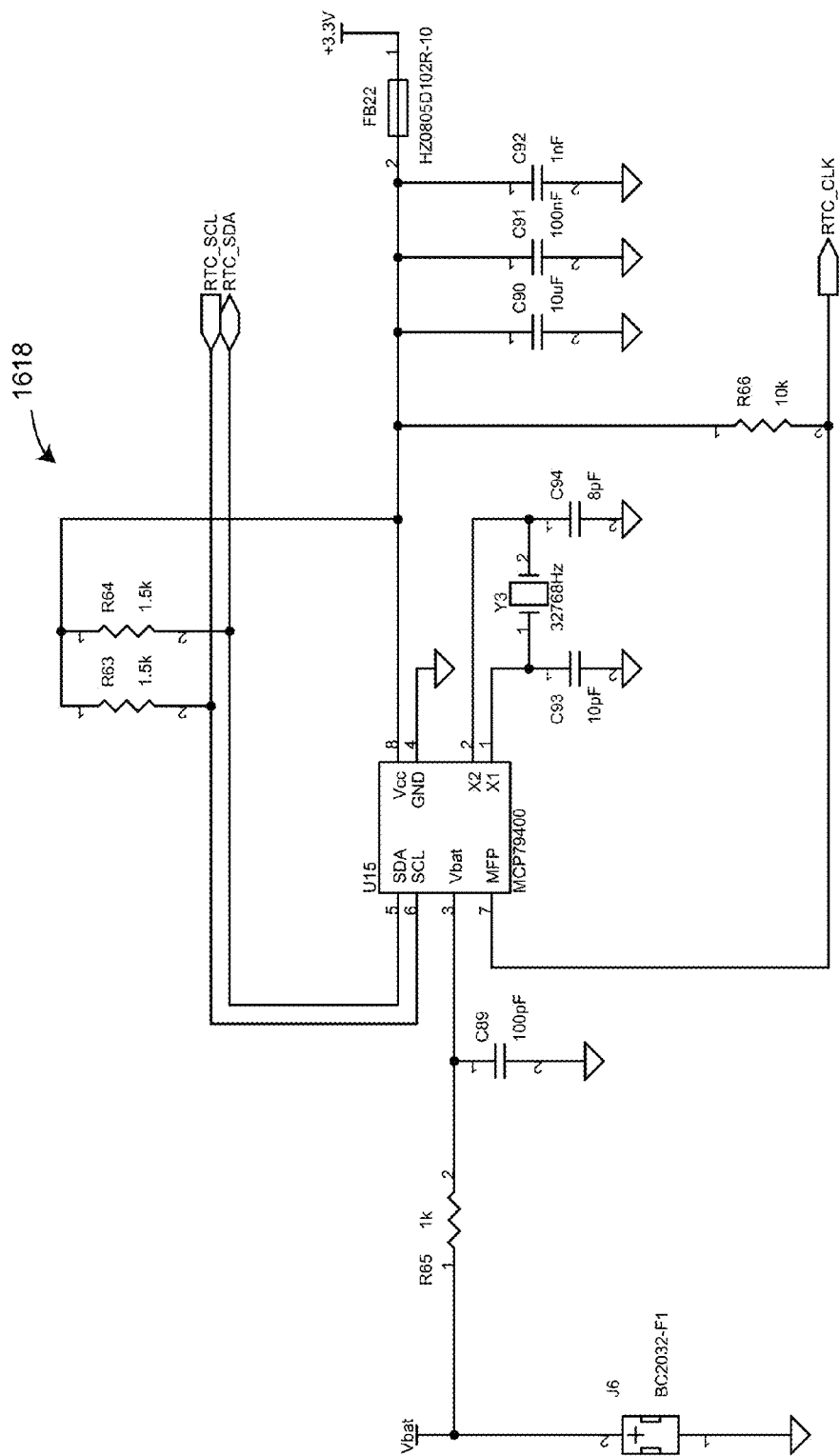
FIG. 28 depicts an example real-time clock that can be used with an energy delivery console.
Figure 29:
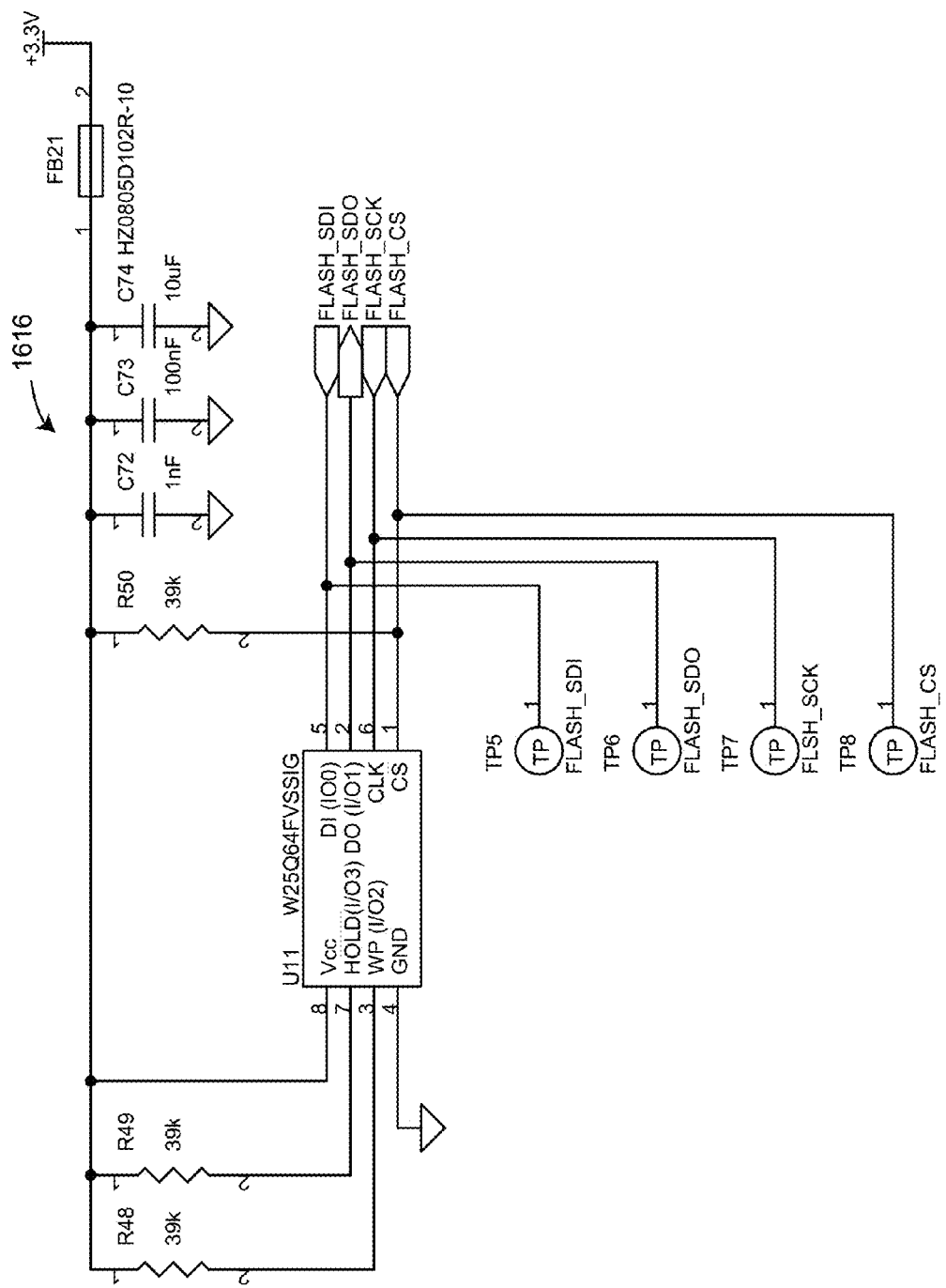
FIG. 29 depicts an example flash memory that can be used with an energy delivery console.

Referring back to FIG. 16, energy delivery console 104 receives power via mains connector 1636 to multi-voltage power supply 1634, which is connected to display 1632, described above, and the primary control board that includes console CPU 1600. FIG. 24 depicts an example circuit for multi-voltage power supply 1634, mains connector 1636, and multi-voltage output 2400 and FIG. 27 depicts an example circuit diagram for touch screen display 1632. Further, energy delivery console 104 may include one or more SD Cards. In this example, energy delivery console 104 includes SD Card circuits 1624 A and 1624 B. Accordingly, FIG. 25 depicts example circuit diagrams for SD Card A 1624 A and SD Card B 1624 B. In this example, CPU 1600 is connected to audio processor 1626 that can process audio signals and provide them to audio output 1628 or speaker to provide alerts and the like to a user. FIG. 26 depicts example circuit diagrams for sound processor 1626 and audio output 1628 that can be used with energy delivery console 104. Further, CPU 1600 is connected to reset switch 1630, real-time clock 1618, and flash memory 1616. Accordingly, FIG. 28 depicts an example circuit diagram for real-time clock 1618 and FIG. 29 depicts an example circuit diagram for flash memory 1616 that can be used in energy delivery console 104.

Figure 31:
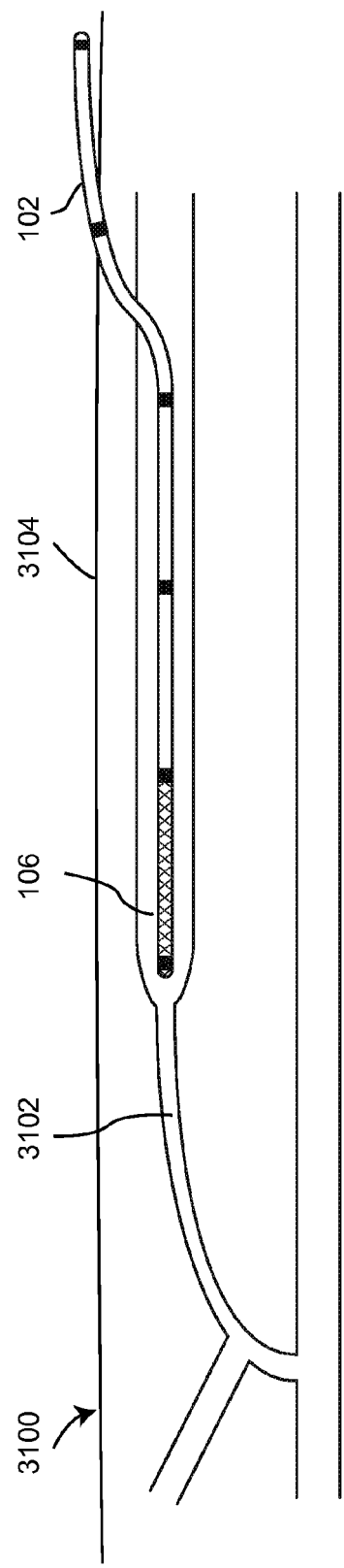
FIG. 31 depicts an example diagram of a heating catheter placed within a vein lumen.

FIG. 31 depicts example diagram 3100 of heating catheter 102 placed within vein lumen 3102. In a specific implementation of an example treatment method, vein lumen 3102 can be accessed by the user (e.g., surgeon, doctor, assistant) using a Seldinger technique. For example, a needle can be placed through skin 3104 into vein lumen 3102, then placing a flexible access wire through the needle into vein lumen 3102, retracting the needle while the access wire remains within vein lumen 3102, placing a sheath with vessel dilator over the access wire into vein lumen 3102 and finally retracting the access wire and dilator leaving the sheath in vein lumen 3102 extending out through skin 3104 to provide ready access for heating catheter 102 directly to vein lumen 3102.

Alternatively, the vein lumen can be accessed by a cutdown technique (incising the skin and subcutaneous tissue with a sharp blade, visualizing the vein, cutting through the vein wall and directly placing a sheath into the vein lumen). For treatment of a Great Saphenous Vein (GSV), blood vessel access is commonly done near or just below the knee, or near the medial ankle A heating catheter is placed into the vein lumen (typically through a sheath) and advanced through the vein to the intended starting treatment site; for GSV treatment this advanced location is typically at or near the sapheno-femoral junction (SFJ) near the patient's groin. Ultrasound visualization is commonly employed to guide heating catheter 102 to the SFJ and to precisely apply heating with respect to the deep vein and/or vein branches.

In a specific implementation, in some cases with tortuosity (very curvy shape) of the vein, or awkward branching angles of side-branches that prevent easy insertion of the heating catheter to the advanced location, a guide wire can be used to assist in correct positioning of the heating catheter. In this case, the guide wire is first advanced to the intended starting treatment site and then the heating catheter is advanced over the guide wire to the intended starting treatment site. Use of a guide wire to facilitate advancement of a heating catheter is also helpful in cases where multiple veins will be treated within the same session, as treatment of one vein can cause other nearby vessels to spasm (constrict to a tighter lumen), thereby making vessel access and/or advancement of the catheter more difficult.

In a specific implementation, a common method of local anesthesia used with endovenous thermal ablation is via infiltration of the nearby tissue surrounding the vein along the full length of the treated vein segment. In this method, the anesthetic solution (e.g., a mixture of lidocaine, epinepherine and sometimes Sodium Bicarbonate) is injected via a long needle or cannula into the perivenous space surrounding the vessel to be treated. For GSV treatment, the anesthetic solution is injected into the 'Saphenous eye' which is the elongated region of tissue between the deep muscular fascia and the superficial fascia where a cross-sectional view appears like an eye-shape (oval pinched at the ends) with the vein near the center. Some other vein segments are not contained within a fascial compartment, and in those cases the anesthetic fluid is injected into nearby tissue so that it mostly surrounds the vein to be treated. The injection of anesthetic fluid can serve several purposes, including but not limited to: localized anesthesia for patient comfort during heating, hydrostatic compression of the vein to empty the vein lumen of blood and push the vein wall into direct contact with the heating catheter, and thermal heat-sink to protect surrounding tissues and nerves from damage by heating.

In a specific implementation, after the heating catheter is positioned in a proper location and the local anesthesia has been applied, additional measures to fully empty the vein segment of blood can be employed. Examples include tilting the body of the patient into the Trendelenburg position (feet up, head down) and direct compression of the vein by external means such as manual compression by hand or wrapping the limb with a compression wrap or sleeve.

In a specific implementation, in the case of segmental ablation, heating catheter 102 is heated by energy delivery console 104. In one treatment example, heating element 106 is heated to approximately 120° C. for twenty (20) seconds for each segmental ablation treatment. Nearest the SFJ, two treatments can be applied, then heating catheter 102 can be moved distally approximately the same length as the length of heating element 106. The movement of heating catheter 102 distally can be guided by a series of printed marks, as discussed in FIG. 2, along the heating catheter shaft, and the user can refer to a datum location (e.g., line drawn on skin, or visualized distance between the sheath and the nearest mark) aligned with a shaft mark. For unusually large veins, or aneurysmal sections of veins, the user can choose to perform multiple treatments (e.g., two to five) within each vein segment. Successive treatment of vein segments can be repeated until the entire desired length of vein has been treated, and then the catheter (and sheath, if used) is removed from the vein.

In a specific implementation of a treatment example, a desired heating cycle is repeated conditionally upon the size of the vessel, where a vein segment smaller than 10 mm in diameter is treated with one energy delivery cycle, a vein segment 10 mm or larger but smaller than 18 mm is treated with two energy delivery cycles is treated with two energy delivery cycles, and a vein segment 18 mm or larger is treated with three energy delivery cycles. At vein segments nearest the source of reflux (such as nearest the SFJ) an additional energy delivery cycle may be added.

TABLE 1

Recommended vein section treatment protocol

| Vein Section Diameter | Section nearest SFJ or deep vein | Remaining sections |
| --- | --- | --- |
| Less than 10 mm | 2 treatments | 1 treatment |
| 10 mm-17.9 mm | 3 treatments | 2 treatments |
| 18 mm and larger | 3 treatments | 3 treatments |

In a specific implementation of a treatment example, shorter lengths of veins (such as perforator veins, which provide a connection between superficial veins such as the GSV and the deep veins such as the common femoral vein) can be treated at a higher temperature and/or for a longer treatment time. Examples would be a treatment at 120° C. for forty (40) or sixty (60) seconds, which can be accomplished by two or three twenty-second treatments, or a treatment at 140° C. for twenty (20) or thirty (30) seconds.

In a specific implementation of a treatment example, control of heating is managed to achieve an initial temperature for a period of time and then to increase to a higher temperature. In one example the initial temperature is at or near boiling temperature for the fluid (e.g., blood) in the lumen and then after an initial period that can cause spasm of the vessel and/or drive the soluble gas from within the surrounding fluid the temperature is increased above the boiling temperature for the fluid.

In a specific implementation of a treatment example, the control of heating can be configured to provide a ramp-down of temperature near the end of the treatment, to allow the heated tissue more time to adjust as it re-approaches body temperature.

In a specific implementation of a treatment example, vessel access for short vein segments can be accomplished using a simpler method than previously described. For example, a needle (or short sheath) can be punctured through the skin directly into a perforator vein. A needle can be guided into a vein using ultrasound visualization. In guiding a needle into a vein using ultrasound visualization, the needle can be pushed into the patient towards a view until an ultrasound image shows the needle tip within the lumen of the vein and blood flashback drips from the end of the needle indicating that the needle lumen is in fluid communication with the blood lumen. An energy delivery catheter, either flexible or rigid in design, can then be placed through the needle into the vein lumen. Once the energy delivery catheter is located within the vein lumen, the needle can be refracted if desired. The energy delivery catheter can be advanced further along the vein lumen if desired, guided by angulation of the catheter shaft, by rotation of a curved tip of the energy delivery catheter, and/or by advancing the energy delivery catheter over a guide wire inserted through the catheter lumen.

In a specific implementation of an example of treatment of a generally T-shaped (or angled-T) blood vessel junction, such as the anastomosis between a perforator vein and the overlying superficial vein, a method of performing a T-shaped ablation can include introducing the energy delivery catheter into the superficial vein at a site that is distal or proximal to the perforator vein, and then advancing it past the perforator vein junction to a site more proximal or distal. Energy can be delivered to the proximal superficial vein segment via segmental ablations, continuous pullback while heating, or by a combination thereof, to the junction of the vessels. Next, the catheter can be advanced down into the perforator vein (ideally past the deep fascia layer and near to the deep vein) and energy can be delivered to the perforator vein, via segmental ablations, continuous pullback while heating, or by a combination thereof. Finally, the catheter can be positioned in the distal-superficial vein segment and energy can be delivered to the proximal-superficial vein segment via segmental ablations, continuous pullback while heating, or by a combination thereof.

In a specific implementation of another example of treatment of a T-shaped junction, an energy delivery catheter can be configured to provide a T-shaped heating pattern. Using a T-shaped heating pattern, the junction can be heated by placing the catheter at the junction to align the T-shaped heating pattern applicator with the T-shaped blood vessel junction and then heating at that location to permanently close or re-shape that junction. A T-shaped heating pattern can be created with a device configured to heat along a length of the catheter (similar to the heating elements described herein) but that also has a side hole along the length of the heating element where a secondary heating member can be advanced through. Another method of creating a T-shaped heating pattern is to provide a heating element with a side hole along its length, where heated fluid is ejected through the side hole such that the heated fluid (near, at, or above boiling temperature) creates the intersecting portion of the T-shaped heating pattern.

In a specific implementation of another example of treatment of a T-shaped junction, an energy delivery catheter can be configured to provide an L-shaped heating pattern. With an L-shaped heating pattern, a catheter can similarly be placed to align with the vessel junction and then heating can be applied. A similar effect can be obtained by locating a flexible heating element across a generally L-shaped blood vessel junction to cause a generally L-shaped heating pattern.

In a specific implementation, after ablation, compression is applied along the treated vein segment or entire limb can be employed by compression stockings and/or external compression wrap, typically for a few days after treatment. Success of thermal ablation methods is usually very high, with 95% or better rate of complete vessel occlusion (no blood flow through the treatment segment) at one year after the procedure. A secondary measure is the reflux-free rate, where there is blood flow but it is unidirectional (toward the heart) as in a properly functioning vein system. Both of these blood-flow measures (occlusion and reflux-free rates) are surrogates to the actual measures of patient clinical symptoms (e.g., pain, tenderness, mobility, venous clinical severity score, chronic venous insufficiency questionnaire (CIVIQ), Aberdeen varicose vein questionnaire (AVVQ™), reflux disease questionnaire).

In a specific implementation, energy can be delivered to the intended vessel by segmental ablation, where the energy delivery catheter is positioned at a location and then remains stationary while a defined period of energy delivery commences and then the catheter is relocated to the next location. In this manner, a length of vessel longer than the heating element can be treated in a series of successive steps. In locations near anatomical sources of greater vessel pressure, such as near the SFJ in the case of GSV treatment, a greater amount of delivered energy can be applied. This can be accomplished by repeating treatments at that location before moving the heating element to a next location, by extending the treatment time, or by increasing the treatment temperature. Movement of the energy delivery catheter can be according to marks along the catheter shaft, such as moving the catheter shaft lengthwise approximately equal to the length of the active heating element.

In a specific implementation, the length of the treatment time (e.g., 20 seconds, 30 seconds, 40 seconds) or the total amount of energy delivered (e.g., 60 J/cm, 80 J/cm, 100 J/cm, 120 J/cm) may be user-selectable, such as by pressing a touchscreen to select a desired time or by pressing one of two or more treatment buttons on a catheter handle whereas each of the treatment buttons signifies a desired treatment time or energy delivery.

In a specific implementation, the length of active heating of the catheter is user-selectable between a shorter active length and a longer active length. Vessels shorter than the longer active length can be treated with the shorter active length, and vessels longer than the longer active length can be treated by the longer active length or a combination of one or more treatments with the shorter active length as well as one or more treatments of the longer active length.

In a specific implementation, energy can be delivered to the intended vessel by pullback ablation, where the heating element active length is heated while the energy delivery catheter is pulled along the lumen of the vessel; in this manner heating is applied in a fashion similar to painting with a brush.

In a specific implementation, control of the actual delivery of energy to the heating element can be via temperature feedback (e.g., proportional-integral-derivative (PID) control) to achieve and maintain a desired treatment temperature, by delivery of a set power level, or by delivery of a variable power level according to a power-time relationship. A power-time relationship can be configured to approximate the level of power per time that would normally be delivered to an intended vessel if that system were temperature-controlled to attain and maintain a desired set temperature. One method of determining such a power-time relationship is by measuring (or recording and later analyzing) the delivered power over a succession of time intervals for a number of vessel treatments by a number of different users on a number of different patients. Another method of determining such a power-time relationship is by measuring such data from a particular doctor or a group of doctors. Another method of determining such a power-time relationship is by establishing a bench-top heating configuration that matches the thermal characteristics of human tissue during heating treatments and then measuring such data as above in the bench-top model.

In one example of power delivery for thermal ablation of refluxing veins, a 7 cm length of 7 F OD heating element is heated to a set temperature of 120° C. for 20 seconds. In a specific implementation, an exemplary power level delivered to achieve and maintain that temperature is approximately 35-40 W in the first second of heating, 30-37 W in the second, and 27-32 W, 23-29 W, 20-27 W, 18-24 W, 17-23 W, 16-22 W, 16-21 W, 15-20 W, 15-20 W, 15-20 W, 14-19 W, 13-18 W, 13-18 W, 13-17 W, 12-17 W, 12-17 W, 12-17 W, 12-17 W in the third through twentieth seconds of treatment, respectively. These same values, each divided by 7, give an example power level per centimeter of active heating length. In one exemplary use of the above energy delivery power-time relationship, a 10 cm length of 7 F OD heating element may have energy delivery of approximately 50-60 W in the first second of heating, 45-55 W in the second, and 40-50 W, 35-45 W, 30-40 W, 25-35 W, 24-34 W, 23-33 W, 22-32 W, 21-31 W, 20-30 W, 19-29 W, 18-28 W, 17-27 W, 17-26 W, 16-26 W, 16-26 W, 15-26 W, 15-26 W, 15-26 W in the third through twentieth seconds of treatment, respectively; smaller diameter heating elements can heat blood vessels to a slightly higher temperature, or for a relatively elongated time period, due to reduced surface area to transfer the heat out to the tissue.

In a specific implementation, a method of setting these energy delivery parameters (as in the above examples) for any particular size configuration (e.g., a 6 F, 5 F or 4 F heating element of a particular length) is to conduct a series of treatments in blood vessels or surrogate tissues where temperature-controlled (e.g., PID control) heating is accomplished to achieve and maintain a desired continuous temperature or variable temperature profile. The measured or recorded energy delivery data are then stored and analyzed in aggregate, applying a suitable confidence interval to the upper and lower bounds of the data or simply calculating a mean or median value at each time point and then appropriately smoothing the curve.

Figure 32:
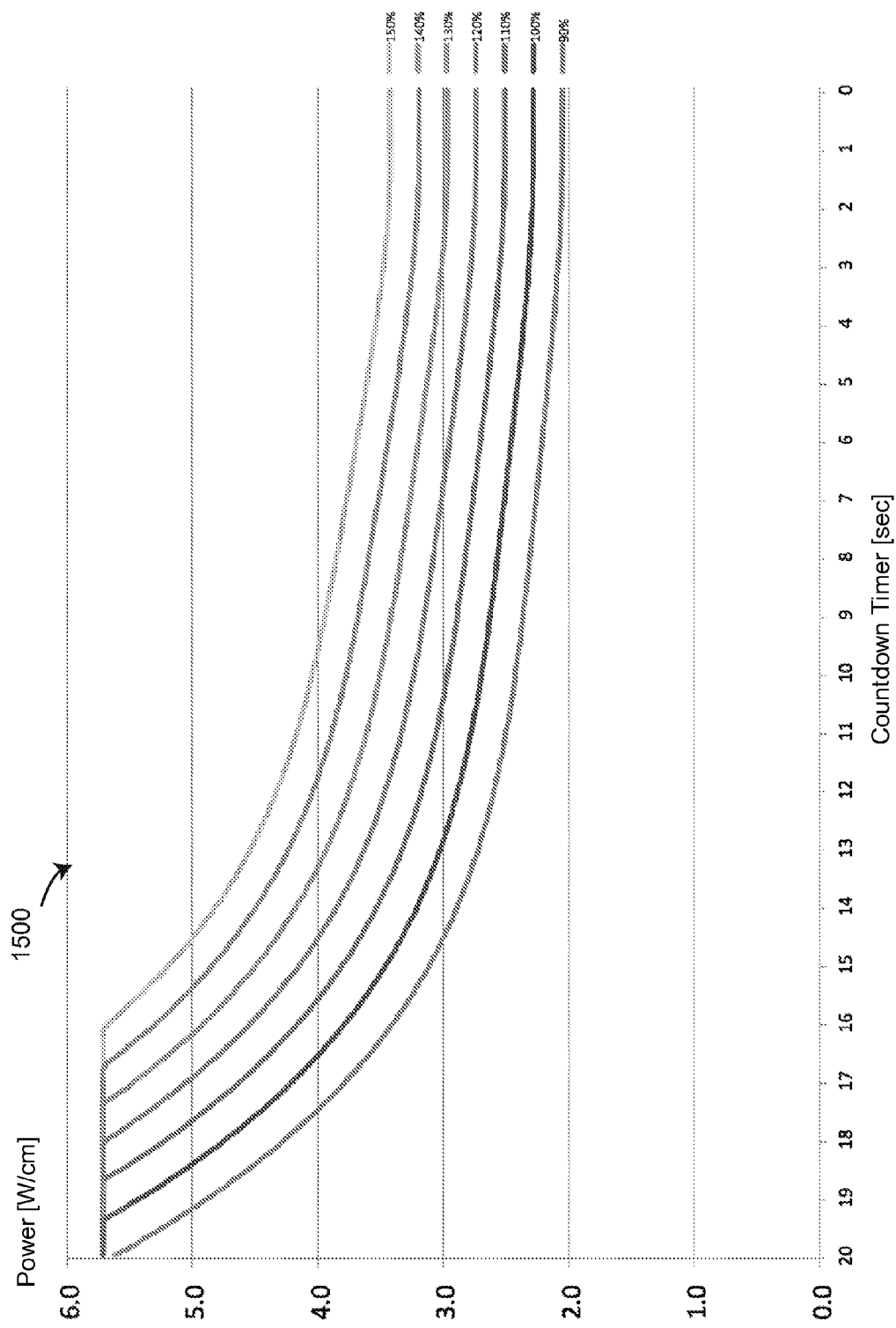
FIG. 32 depicts example power-time curves for powering a heating catheter.

FIG. 32 depicts example power-time curves 3200 for powering a heating catheter. In a specific implementation, energy is delivered without temperature measurement and the energy is delivered in a power-time configuration that matches a typical power-time configuration that is obtained with a temperature-controlled device that may be of similar heating element dimensions, or a selected increment above or below such typical power-time configuration. Exemplary power-time relationships are shown above, such as the 100% power-time curve or the 120% power-time curve. Such a configuration without temperature measurement can represent significant cost savings in device construction. In a further specific implementation, the catheter consists of a heating element with non-stick covering on a catheter shaft. The catheter shaft is connected to a minimal handle (which may or may not include a button to start/stop treatments) to a cable assembly. The cable may plug into energy delivery console 104 by a ¼" TRS stereo plug if the cable is grounded, or by a ¼" TS mono plug if the cable is not grounded. The cable plug housing may include an RFID tag that can be recognized by energy delivery console 104 to identify the catheter type, to confirm that the catheter is an authentic approved product, and to limit the use of the catheter to an approved number of uses (e.g., only a single use or multiple uses such as 3× or 10×).

In a specific implementation, in a method of energy control, energy delivery is set to a predetermined or user-selectable total energy delivery (such as approximately 60, 80, 100 or 120 Joules per centimeter of heating element active length) and energy is delivered until that total value has been reached. A lesser amount of energy (e.g., 60-80 J/cm) is activated by a single press of the catheter button while a greater amount of energy (e.g., 100-120 J/cm) is activated by a double press of the catheter button in quick succession. A variable amount of energy can be metered by a difference in length of time the vessel is heated to approximately maintain a desired temperature. A variable amount of energy can also be metered by a difference in approximate temperature the vessel is heated to during a similar time interval. During energy delivery, the instantaneous amount of energy can be moderated by an engine (e.g., processor or process) to set and maintain a desired temperature (e.g., via PID control), energy can be set to a constant value, or energy can be delivered according to a pre-set power versus time relationship via lookup table or mathematical algorithm managed by an engine. There may also be a condition where the greater value of time to deliver total desired energy or minimum cumulative time at or near a set temperature is chosen, as cooling of the energy delivery catheter by an excessive amount of surrounding fluid (e.g., blood) can cause the total energy to be delivered more quickly than would be ideal for successful treatment, as the energy is not delivered efficiently into the intended treatment tissue such as the vein wall.

In a specific implementation, delivered power is integrated over time to determine the history of energy delivered (e.g., in Joules (J) or J/cm). If an intended specific energy delivery is desired (e.g., 80 J/cm) then energy can be delivered according to a reference table of delivered energy per elapsed time until such time as the integrated delivered power is equal to or slightly greater than the intended energy delivery. Similarly, energy can be delivered as required to reach and maintain a desired temperature until such time as the integrated delivered power is equal to or slightly greater than the intended energy delivery.

In a specific implementation, a variety of features and methods can be employed to facilitate tracking of the energy delivery catheter from the access site to the desired treatment starting location of treatment (e.g., the SFJ when treating the GSV). The energy delivery catheter can simply be pushed through the vasculature to the start location, if the vessels are sufficiently straight with no angled vessel branches that favor the catheter following the branch in the wrong direction. A guide wire can be inserted through the energy delivery catheter to the start location and then the energy delivery catheter can be advanced over that guide wire. The energy delivery catheter can be advanced within the body of a long guide catheter that has previously been advanced to the start location.

In a specific implementation, an energy delivery catheter can have a generally curved shape to cause it to advance like a guide wire, where rotation of the catheter shaft while advancing can be employed to select which vessel branch to follow; a tip curve bend radius of approximately 3" to 8" would be sufficient. For example an energy delivery catheter with a curved tip may not have a lumen through it. Alternatively, the energy delivery catheter can have a steerable tip, where the radius of curvature is user-adjustable such as by pulling tension on a wire built into one-side of the catheter shaft to cause that side of the catheter shaft to become shorter in length and effectively bend that catheter shaft.

In a specific implementation, a magnetic material, a material affected by magnetic force, or an electromagnet can be incorporated near the tip of the energy delivery catheter so that the user can apply magnetic force to attract the tip in a desired direction. Examples of controllable sources of magnetic force include rare earth magnets, neodymium magnets and MRI.

In a specific implementation, confirmation of final catheter position at the point of treatment start can be via ultrasound visualization, visualization of light energy transmitted through the skin (as from a light-emitting diode or multiple diodes built into the catheter near the tip, near both ends of the heating element, or near both ends of each user-selectable heating length along the heating element) or surgical cut-down and direct visualization or palpation of the catheter tip. An exemplary distance from the nearest deep vein is two (2) centimeters. A catheter can have a fixed guide wire attached to the tip of the catheter. This would have the advantage of assisting catheter navigation through the vasculature (as with a standard guide wire) and it could also extend precisely a desired length beyond the region of catheter heating (such as 2 cm distal to the heating element) and be used as a visible measure to be aligned with an anatomical structure such as aligning the tip of the fixed guide wire with the SFJ.

In a specific implementation, a method of alerting the user if the vessel heating is not proceeding in a fashion typical with the intended treatment (such as heating of a superficial vein after anesthetic fluid has been injected to surround the vessel and empty the vessel of blood so that the energy delivery catheter is predominately heating the vein wall as opposed to heating a significant volume of fluid such as blood surrounding the catheter) is to provide a time-variable maximum power level to the heating catheter. In such a case, if there is an unusual volume of fluid surrounding the heating element (providing a cooling action to the area and acting against the intended heating of the vessel wall) the set temperature will not be able to be achieved or maintained, and the user will notice that the treatment temperature displayed on energy delivery console 104 has fallen below the intended treatment temperature. After a determined time of falling below the intended treatment temperature, the user can be given an alert (text, icon and/or sound) that indicates that there is excess cooling around the heating catheter. This notice may prompt them to make an adjustment to bring the heating element into improved contact with the vessel wall such as by further emptying blood from the vessel.

In a specific implementation, the 120% power curve as shown in FIG. 32 is used as the maximum allowable energy delivery over time. For a unique catheter design and energy delivery system design, a similar curve can be created by measuring the average, median, or other typical energy delivery over time for a number of treatments within a representative system where the heating energy is determined such that a desired treatment temperature is achieved and maintained. In a further specific implementation, a time-dependent temperature relationship is obtained over a number of treatments in a representative system and a subsequent power-time relationship is determined and created to obtain a similar time-dependent temperature relationship without the use of direct temperature measurement.

In a specific implementation, if the temperature of the heating element is too low relative to the level of power delivered or if the required level of power to achieve the set temperature is too high (such conditions indicating an excess of fluid surrounding the heating area of the energy delivery catheter, instead of ideal heating of predominantly the vein wall) the user may be alerted by showing a pictorial representation of the catheter with a pictorial representation of fluid or cooling surrounding the heating area. Alternatively a message such as, for example, "Alert: excess fluid, empty the vein" may be displayed.

In a specific implementation, the quickness in which the treated vessel segment can be brought to the intended treatment temperature can be used as an indication of vessel wall contact and absence of blood or fluid that otherwise cools the area. If the measured temperature is not achieved in a set time (for example, for a set temperature of 120° C. heated with a 7 cm 7 F heating element at maximum power of 40 W, the temperature typically is displayed greater than 115° C. after three seconds of heating) the user can be alerted, the heating can be stopped automatically and/or the power level can be dropped to a level that is insufficient to coagulate blood within the vessel lumen.

In a specific implementation, uniformity of temperature along the heating element can be indicated by comparison of temperature measured at different points along the heating element. Knowing if the temperature is non-uniform can help prevent a part of the heating element from becoming so hot that it can cause damage to the device, so alerting the user and/or automatically stopping the treatment or automatically reducing power to a lower level is a benefit. In the case where electrical resistance of the heating element is dependent on temperature such that temperature can be predicted by the measured resistance, e.g., resistance temperature detection (RTD), the heating element resistance can be compared by an engine via a reference table or algorithm of resistance versus temperature against the temperature measured by a thermocouple or thermistor. If the values disagree by a determined amount (e.g., 10-20° C. or more) it indicates that the heating element is not substantially uniform in temperature. In such a case, the user can be alerted by sound/text/code and/or the system can automatically reduce power level or terminate treatment early or reduce heating temperature to a lower level; in such conditions the user can be alerted to adjust the catheter or the compression techniques to create more uniform contact between the heating element and the vessel wall. An alternative method to determine if the heating is not within expected parameters is for an engine to compare the measured temperature (e.g., from thermocouple, thermistor or RTD measurement) to a reference table or algorithm of known expected temperature versus time for a similar energy delivery power-time relationship.

In a specific implementation, resistance or impedance of the heating element is continually measured by an engine to detect a change consistent with unusual heating of the element or physical damage to the element. In such a case, the treatment can be automatically stopped, power can automatically be decreased to a lower level, and/or the user can be alerted to the condition.

In a specific implementation, prior to beginning treatments the user can be notified that the tissue surrounding the energy delivery catheter heating element has been infiltrated with local anesthetic fluid; this condition can be sensed by an energy delivery system engine when room temperature fluid is injected, as the nearby fluid injection causes the treatment vessel to drop temporarily from body temperature to room temperature and the engine can sense that temperature level. For example, a user notification tone or alert can be given after the catheter has measured body temperature (approx. 34-39° C.) for more than a predetermined time (e.g., 15 sec) and then drops to a lower temperature such as room temperature (e.g., 24-28° C.).

In a specific implementation, after treatment, it is preferable if the user is able to know that the treated vessel has been substantially coagulated, with shrunken vessel diameter being a key indicator. This can be observed under ultrasound visualization, but immediately post-treatment an under-treated vessel can be in spasm. One indicator that can be of benefit would be a measurement of the force required to pull the energy delivery catheter (and heating element) to the next vessel segment. Force can be measured by a strain gauge applied to the catheter shaft or within the handle, or by a simple spring-gauge measurement built into the handle. An acceptable force above a minimum acceptable threshold can be displayed as a visual cue and/or an audible cue can be presented.

In a specific implementation, a Doppler ultrasound crystal is included in the energy delivery catheter to measure blood flow within the vessel lumen, providing a direct means of measuring or indicating blood flow or the desired lack of blood flow.

In a specific implementation, for an energy delivery catheter with user-selectable heating length (e.g., 10 cm or 2.5 cm) the length of active heating may be selected by the user by pressing a touchscreen display, such as by pressing an image of the catheter and heating element. In this example, the default heating length may be the longer length and if the screen image is pressed the selection of the shorter length is made in the software and the image of the catheter shows the shorter active heating length. Further pressing of that area of the screen (for example, when the heating is not active) toggles between the two active heating lengths. In one example, with three user-selectable heating lengths, pressing the screen image toggles serially between the three heating lengths.

In a specific implementation, for an energy delivery catheter with user-selectable heating length (e.g., continuous range from 10 cm to 1 cm) the length of active heating may be selected by a slide-able electrode contacting the proximal (or distal) end of the active heating length. The slide-able electrode may contact the heating element along a range such as 10 cm from the distal end of the element to 1 cm from the distal end. Effective length of heating may be measured by sensing the impedance between the two electrical contact points of the heating element (e.g., soldered connection at distal end and spring-contact connection at a more proximal position) or by electrically switched selection. The user interface on energy delivery console 104 can display the effective heating length to the user, deliver the appropriate energy for heating a segment of that length, and may show heating energy as intensity per unit length of heating (e.g., W/cm).

In a specific implementation, a foot pedal has multiple switches where one switch serves to start or stop treatments and another switch serves to toggle user-selectable heating length. In another example the handle has two switches, with one switch serving to start or stop treatments and the other switch serving to toggle user-selectable heating length. Alternatively, in an example where a handle has two switches, one switch can be used to start a longer heating length while the other switch can be used to start a shorter heating length; in a further specific implementation, pressing either of the two switches during energy delivery will stop energy delivery immediately.

In a specific implementation, the energy delivery console plays sounds to indicate treatment, such as identifying when heating to set temperature, and when heating to continue at set temperature. In a further example, the pitch or the tones or a different change to the tones indicates if a user-selectable treatment length catheter is heating a shorter or longer active heating length.

In a specific implementation, for example systems where the active heating length of the heating element is selectable by the user (e.g., 10 cm or 1 cm), markings approximately equal to the length of the shorter heating length can be made along the length of the heating element. A series of markings can be made where one visual cue (such as a series of dots) can be made spaced approximately equal to the length of the shorter heating length and another visual cue (such as a series of lines) can be made spaced approximately equal to the length of the longer heating length. This can be done to indicate where the shorter length of heating is, or to facilitate segmental positioning and heating of the shorter length of heating within the blood vessel. Markings can be created by printing on the tubing material (e.g., pad printing, screen printing, painting, designed coloration of the tubing material) over which a coil heating element is located, if the spaces between coils are sufficiently wide to allow visibility of the markings. Alternatively, the heating element or coil itself can be directly printed (e.g., pad printing) either in a pre-coiled configuration or after loading onto the tubing material. Alternatively, a very thin layer of colored tubing can be placed over the heating element (e.g., PET heat shrink, approximately 0.0005"-0.001" thick), with alternating pieces of different colors, or short segments, or segments of visible colors, making up a pattern that facilitates segmental steps of location for heating with the shorter heating length. This marked outer layer can make up a final outer layer covering the heating element, or it can be covered by an additional layer such as FEP, PTFE, or PET. Alternatively, a pre-printed layer of tubing can be shrunk over the heating element and/or over the tubing material.

In a specific implementation, a heating element coil can be located on the shaft by coiling wire directly on the catheter shaft or section of tubing, by sliding a pre-wound coil loosely over the catheter shaft or section of tubing or by using counter-rotation of a heating coil element to temporarily spring a pre-wound coil smaller than will slide on the catheter shaft or section of tubing to a larger diameter to fit the coil over the catheter shaft or section of tubing. In a specific implementation, the tubing can be rotated while pushing it inside the heating coil so that the tube rotation tends to open up the coil diameter to allow the coil to slide, wind or screw over the top of the tubing. In a specific implementation, the heating coil may be rotated while loading over the tubing so that the coil rotation tends to open up the coil diameter to allow the coil to slide, wind or screw over the top of the tubing. The heating element coil may have a shaped end configuration that interacts with the outer surface of the tubing to guide or steer the heating coil over the shaft into the desired position.

In a specific implementation, wiring connections to the heating element can be made by soldering conductive wires to the heating coil after it has previously been loaded onto the shaft, or by pre-wiring the heating coil (solder or welding) and then placing the wired assembly onto the shaft. In one configuration, holes or slots can be located in the tubing (e.g., by cutting with a hole-cutter, skiving, or by laser drilling) near sites where the wires will penetrate into the interior, before the heating coil is loaded into place. In a further specific implementation, after the wires are located in their final positions within the holes or slots through the tubing, adhesive may be applied to the holes or slots to preserve the integrity of the tubing against kinking if bent at that location. In one configuration a slit can be made in one or more end(s) of the tubing over which the coil assembly will be loaded, allowing room for conductive wires to enter the tubing lumen close to the heating coil end(s). In an example, a channel in the tubing over which the coil assembly is loaded allows one or more conductive wires to be located underneath the heating coil so that a plurality of conduction wires can enter the tubing lumen near the distal end of the coil assembly. In another example, a long slit is made in the tubing under the heating coil to allow wire passage or placement, and a shaped piece is slid inside the tubing under the coil to provide mechanical support to prevent the coil-loaded assembly from bending in an undesirable fashion such as easily kinking.

In a specific implementation, for an example system where the active length of heating is user-selectable, the electrical circuit to accomplish the selection can be created by attaching conductive wires to each end of a heating coil and to the point(s) part-way along the heating coil (e.g., as measured from the distal end of the coil, conductive wires attached at 0 cm, 2.5 cm and 10 cm proximal). The wire located part-way may be directed into the lumen of the tubing at that location, or it can be located directly under the coil, over the coil, or between coil winds until it reaches a more favorable location to enter the tubing lumen, such as near the distal end of the heating coil. A layer of insulation must exist between the heating coil and any conduction wire that physically is located across adjacent coils; that insulation can be on the conduction wire itself, on the heating coil itself, a layer of material generally between them, or a combination thereof.

In a specific implementation where the active length of heating is user-selectable, the shorter-length wiring connection (for example, 2.5 cm proximal to the distal end of the heating coil) is made using a wire that is smaller than the wires that connect to the two ends of the coil. This smaller wire may be continued through the handle and cable all the way to the energy delivery console, or it may be smaller only along a portion of its length such as from the 2.5 cm location to the distal end of the coil. In a further specific implementation, the shorter-length wiring connection between the 2.5 cm location and a point near the distal or proximal end of the heating element is a ribbon wire that is 2-8× wider than it is thick.

In a specific implementation, the shape of the heating element is modified before or preferably after loading onto the catheter tubing so that a transverse section view of the heating element is not round (as would be typical) but instead has a flat or depressed section along all or a portion of its length to allow space for wires external to the coil while keeping a minimal profile of the catheter through a circular aperture such as within an access sheath.

In a specific implementation of a two-piece heating coil assembly, a proximal coil segment is wired at both ends with conduction wires, with or without a thermocouple placed at the distal end of the proximal coil, and then a distal coil segment is added and electrically connected to the distal end of the proximal coil (at proximal end of distal coil) and a conduction wire is connected at the distal end of the distal coil. This method can be facilitated by a channel or slit in the underlying tubing that extends from the distal end of the tubing to the junction between the proximal and distal coils; a slit of that type at the distal end of that tubing can be supported by addition of an underlying tube with slit in opposite direction inserted so that the two slits extend in opposite directions from the point that the assembly wires enter the body of the catheter.

In a specific implementation, a heating element is built into an assembly that is designed to withstand the full range of heating temperature (e.g., room temperature, approximately 25° C., up to approximately 200° C. or higher), using high-temperature-resistant shaft materials such as polyimide, polyether ether ketone (PEEK), ULTEM®, or silicone and the heating element/shaft assembly is then connected to a more economical material (e.g., 72D PEBAX®, nylon) to make up the majority of the catheter shaft length. Connection between these two shaft sections can be by adhesive (e.g., UV-cure acrylic adhesive, UV-cure cyanoacrylate, moisture-cure cyanoacrylate, 2-part Epoxy, or water-soluble adhesive) or by melt processing; melt-processing can be facilitated if a polyimide or other high-temperature material has an integral outer layer of compatible melt-processable material.

In a specific implementation, a method of increasing the tensile strength of a catheter assembly can be to include a tensile element within the catheter shaft. For example a wire (e.g., stainless steel, NiTi, copper, other), can be attached to the heating element or to the tubing near the heating element at one end and the handle at the other. This wire can be electrically connected to the coil, providing the conductive connection with that end of the coil, or it can be electrically insulated so as to not connect as a functional part of the electric circuit. If the wire is intended to be conductive, the conduction can be improved by plating (e.g., gold, copper) or cladding.

In a specific implementation, wires that extend therethrough the catheter shaft from the region of the handle to the region of the heating element are siamesed into a bundle to ease loading of the wires. The siamesed bundle may be flat, with wires side-by-side, or multi-layered. A color-coded configuration, such as a flat bundle with uniquely colored wire at one end, or a multiplicity of colored wires, can aid in identification of proper wiring connections during catheter assembly.

Figure 35:
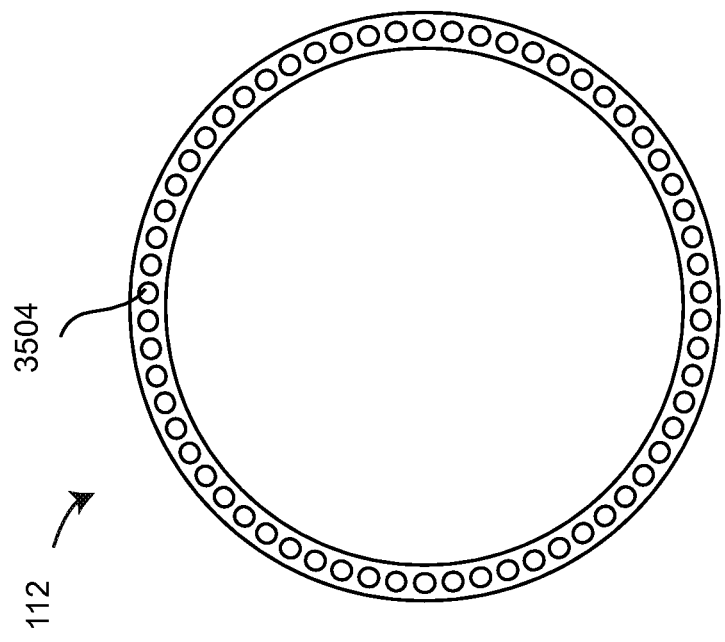
FIGS. 35A and 35B depict example heating catheter air channels designed to promote the visibility of the heating catheter via ultrasound.
Figure 35:
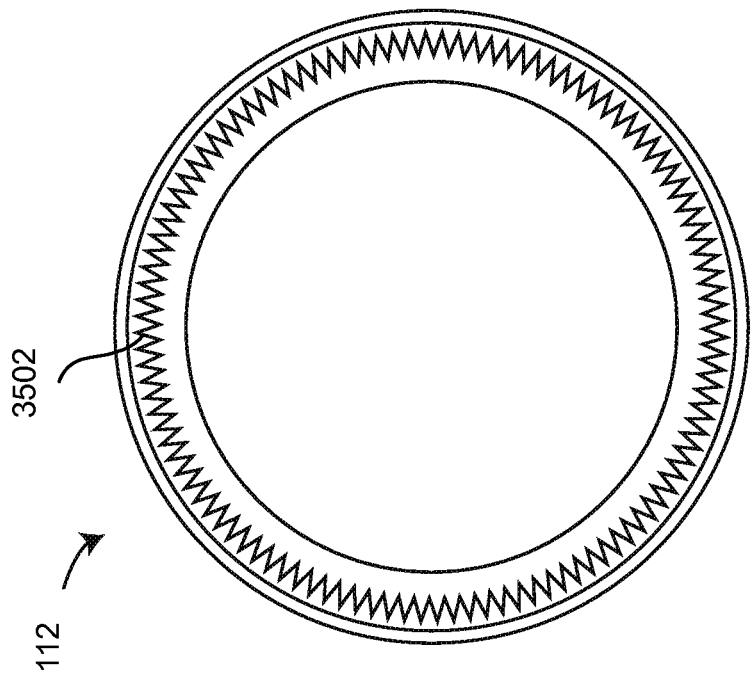

In a specific implementation, visibility of the catheter when viewed through body tissues via ultrasound can be improved by providing a textured surface to improve the reflection of sound waves, or by providing trapped air pockets or channels within the device. Accordingly, FIGS. 35A and 35B depict example heating catheter tubes designed to promote the visibility of the heating catheter via ultrasound. Methods of achieving a textured surface on heating catheter tube 112 include chemical etching, grit blasting, laser machining, sanding or scraping, crimping in a patterned die, or molding key components with the desired texture in the injection mold. Methods of creating trapped air pockets 3504 include leaving space between heating coils that are bridged by an outer layer of material such as a lubricious outer jacket, extruding tubing with a multiplicity of lumens (such as an array surrounding a central lumen), extruding tubing with multiple furrows 3502 along the exterior and then covering the exterior with heat-shrink tubing to cause bridging across the furrows trapping air in small channels, laser machining pockets or furrows into the surface of tubing and then covering the machined area with thin heat-shrink tubing to cause bridging trapping air in the shapes, and heat-processing with multiple wires parallel to the axis of the tubing and then pulling the wires out to leave multiple axis-parallel lumens; such axis-parallel lumens are then fluidly sealed at two ends or in a series to create trapped air channels or pockets.

In a specific implementation, a multitude of cube-corner reflectors is laser machined into the surface of the shaft tubing over which the coil is loaded, or into short sections of tubing that are slid into place over the shaft similar to how marker bands are for visibility under x-ray or fluoroscopy, or into the lubricious outer jacket that covers the heating coil. The physical dimensions of trapped air or surface roughness to improve ultrasound contrast (echogenicity) should ideally be approximately the same as the wavelength of sound used for the imaging. For example, a 10 MHz ultrasound probe uses a wavelength of 0.006" in water (15 MHz=0.004", 6 MHz=0.010").

In a specific implementation, the energy delivery catheter can be powered via a pair of wires (and perhaps store power in a capacitor built into the energy delivery catheter handle or cable) and then use wireless communication (e.g., BLUETOOTH® or ZIGBEE®) between the energy delivery catheter and energy delivery console 104 for catheter identification, temperature and/or resistance/impedance feedback, and start/stop commands. In a specific implementation, an energy delivery system is miniaturized and incorporated into the handle of the energy delivery catheter.

In a specific implementation, catheter electronics for a two or three-wire cable and connector system are combined into an application specific integrated circuit (ASIC) to minimize cost and components within the catheter such as within the catheter handle. In a further specific implementation, such an ASIC includes a logic engine (e.g., microprocessor), memory storage, noise filtering, and means for switching and directing power. In a further specific implementation an ASIC includes input provisions for multiple unique temperature sensors. In a further specific implementation an ASIC includes input provisions for multiple user-interaction buttons. In a further specific implementation an ASIC has the ability to direct power independently or concurrently into multiple energy-delivery features of a medical device. In a further specific implementation an ASIC has the ability to power up several user-interaction devices such as LED lights or ultrasound crystals. In a further specific implementation, a logic board or ASIC is powered from a remote power source such as within the console or by a wirelessly-charged battery. In a further specific implementation, an ASIC includes charge pumps that increase the voltage to transistors (e.g., MOSFETs) that connect the catheter heating elements to the power delivery circuitry; the charge pumps are used to overcome the natural decrease in resistance over time that results from battery use.

In a specific implementation, procedure data storage from a number of most recent treatments can be transferred wirelessly to a memory module built into the power supply. Procedure data storage from each treatment can be relayed to a wireless data device such as a laptop computer, tablet computer or cell phone. Live gauges and/or a start/stop button can be displayed interactively on such a wireless device.

In a specific implementation, information about treatments can be stored within energy delivery console 104, such as date and time of treatment, how many heating cycles were completed, total time of energy delivery, and total energy delivered per cycle (e.g., J/cm). Other information such as temperature and power level over increments of time, measured resistance or impedance of the energy delivery catheter heating element circuit over increments of time, and alerts or status updates (whether displayed to the user or not) can also be stored. This data storage can include the most recent use of 10 or more energy delivery catheters used with energy delivery console 104, as raw data storage or encrypted data storage.

In a specific implementation, an energy delivery system is configured to accept communication from a foot switch (pneumatic, actuated via tubing filed with air, or electrical such as a direct cord, or a cordless information link such as BLUETOOTH® or ZIGBEE®) to provide a signal to start or stop treatments (in addition or instead of a switch on the handle of the energy delivery catheter). A pattern of pressing can be required to initiate treatment, such as a double-press, or energy delivery console 104 might require the pedal to be held down for at least the first 1-2 seconds of each treatment, or depressing the foot pedal can mirror the effect of pressing the handle button.

In a specific implementation, an energy delivery system is configured to interact electronically with a fluid delivery pump, such as to control the delivery rate of fluid by the pump or to monitor the volume of fluid conveyed by the pump. For example, energy delivery console 104 can accept an entry for the beginning volume and/or concentration of the fluid attached (or electronically be provided with some or all of that information) and then display an indicator of how much fluid is remaining to be conveyed while the pump is conveying the fluid. This can help a user know that sufficient fluid is remaining to cover all of the intended bodily tissue anesthetic effect, instead of injecting too much at the start and not having sufficient volume remaining for the final location(s).

In a specific implementation, an energy delivery system is configured to also convey data over the same conductors that provide heating energy current to the heating catheter. Example of data conveyed by an energy delivery system include open/closed configuration of a start/stop button, device identifier, history information of connected device use, and/or temperature. In this manner, electrical conductors between the heating catheter and energy delivery console 104 can be minimized. Energy can be delivered within the radiofrequency range of the electromagnetic spectrum, with severity of heating modulated by amplitude modulation, while one or more data signals are also conveyed at higher and/or lower frequencies. Energy can also be delivered at constant amplitude of direct current energy, with severity of heating modulated by interrupting the current in successive start/stop intervals of varying length (pulse-width modulation), while one or more data signals are also conveyed within the pattern of start/stop intervals.

In a specific implementation, a Wheatstone bridge is connected to thermocouple conductors to assist in energy measurement. The Wheatstone bridge can be located within energy delivery console 104. The Wheatstone bridge can also be located within the heating catheter, such as within the handle of the heating catheter. An isothermal junction of one or more thermocouple leads can be located within the heating catheter, such as within the handle of the heating catheter. A reference temperature sensor, such as an integrated circuit temperature sensor, can be located within the isothermal junction of the heating catheter. The previous methods of reference junction compensation within the heating catheter have a direct advantage in not requiring the dissimilar metals of the thermocouple to be extended all the way from the heating element to energy delivery console 104 and also can facilitate conveyance of data between the heating catheter and energy delivery console 104 over a minimized number of conductor wires.

Since the device is being developed to provide excellent treatment with as little cost as possible, and little or no extra effort will be made to ensure that the device would stand up to many uses, it can be beneficial to be able to control how many times the device can be used to treat patients. This has been common practice in the endovenous laser industry for many years, among other single-use medical devices.

In a specific implementation, an electronic control engine in the heating catheter is used to record data about the state of a heating catheter's use and to convey that information to energy delivery console 104. In one example, an indicator of time of first use or elapsed time of use can be stored within the heating catheter, such as within an integrated circuit within the heating catheter handle or cable assembly. In this manner energy delivery console 104 can determine, via a use control engine, if the heating catheter has been used previously in a procedure and how much time has elapsed since that use; energy delivery console 104 can allow use of the heating catheter within an acceptable period of time to treat a single patient in one treatment procedure, such as for a period of one to four hours from start of first treatment to start of last treatment. This is advantageous in that if a heating catheter is plugged in but the treatment of the patient is cancelled before treatment begins (and before the heating catheter is rendered non-sterile) the catheter can still be preserved sterile and used at a later time on an alternate patient.

In a specific implementation, an electronic control engine in the heating catheter is configured to work with energy delivery console 104 to allow use of the heating catheter for a predetermined number of patient treatments. A common multiple-use scenario for endovenous laser allows use of a laser fiber for up to five patient treatment sessions. In one example an electronic control engine and energy delivery console 104 work together to allow between three and five treatment sessions, where each treatment session can be defined as a group of treatments within an acceptable time window such as one to four hours or each treatment session can be defined as treatment of a single patient; the first treatment to begin after the previous time interval elapses then triggers the start of a successive treatment with a new time interval. Once all acceptable time intervals have completed, the electronic control engine and energy delivery system will no longer allow further treatments.

In a specific implementation, a heating catheter electronic control engine records or counts treatments that have been applied and energy delivery console 104 will allow treatments only up to a threshold number of treatments. In an example, for a heating element length of 10 cm a threshold number of treatment cycles can be in the range of 10 to 30 cycles.

In a specific implementation, a heating catheter electronic control engine records the elapsed time that the heating catheter has been plugged into energy delivery console 104. In an example, after two to six hours of plug-in time the electronic control engine and energy delivery system will no longer allow treatments.

In a specific implementation, data about heating catheter use can also be helpful in diagnosis of a reported malfunction of the heating catheter. It would be helpful to store memory within an electronic control engine of the heating catheter that includes identification of energy delivery console 104 used for treatments, start and stop time for each treatment, and a measure of the energy delivered during each treatment. A record of quality control testing as part of the manufacturing process would also be beneficial. This data would ideally be encrypted to prevent unauthorized changes to the data.

In a specific implementation, electronics within the handle of the heating catheter that includes a battery to power a logic engine and communication are configured to facilitate powering up the logic and communication system after the battery within the catheter assembly has died. In a further specific implementation, circuit board pads or other conductors are configured to be reachable with external probe conductors through the body of the handle such as by removing a button cover and contacting appropriate conductors through the window that previously housed the button cover.

In a specific implementation, data from a sampled group of procedures can be collected on a memory module within energy delivery console 104. This data can be transferred to a business to store in a business memory module. A user can be compensated for sending in this data, such as in product rebates, cash-equivalent or other compensation, or the data can be collected without compensation. The business can analyze this and other data collectively or individually to determine a unique, average or mean energy delivery profile. If the data were collected from energy delivery catheters with temperature feedback, the determined energy delivery profile would be as typically needed to achieve and maintain the same desired temperature. The energy delivery profile would also be usable with similarly constructed (or with equivalent thermal properties) energy delivery catheters that do not include temperature feedback in order to achieve similar tissue ablation characteristics with a simpler and possibly lower cost energy delivery catheter design. The user may be asked to designate what type or size of vessel is being treated, so that energy delivery profiles can be developed for a variety of vessels. In such a case, the user can select on energy delivery console 104 what type of vessel is being treated so the system can associate the proper energy delivery profile to the treatment at hand.

In a specific implementation a similar energy delivery system is used in the treatment of benign prostate hyperplasia by Transurethral Needle Ablation (TUNA). In such a system a radiofrequency needle or needles are placed through the urethra and into the lateral lobes of the prostate. The needles are energized to increase the temperature of the targeted area of the prostate and induce heat-induced necrosis (local tissue death). In a further specific implementation of the procedure, the tissue is heated to 110° C. with a RF power delivered at 456 kHz for approximately three minutes per lesion, causing a coagulation defect. In an alternate specific implementation, a needle is configured to include a heating element that transfers the heat to the surrounding prostate tissue. Such configurations can include the minimized-wiring serial communication designs described above.

Figure 33:
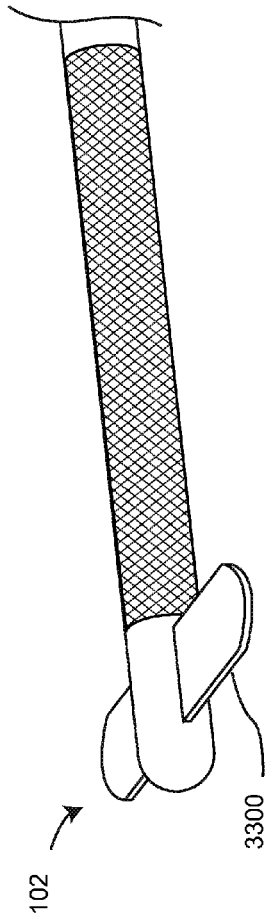
FIGS. 33A-33C depict example techniques that can be utilized to promote self-centering heating within a vein lumen.
Figure 33:
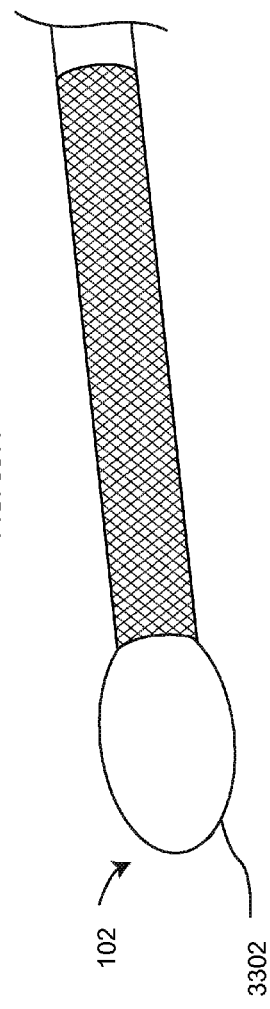
Figure 33:
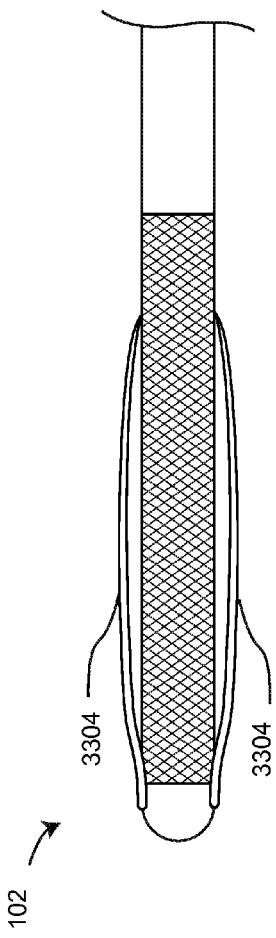

FIGS. 33A-33C depict example techniques that can be utilized to promote uniform heating within a vein lumen. In a specific implementation a similar energy delivery system is used in the treatment of endometriosis by Endometrial Ablation. On such a system, electrosurgery or radiofrequency of the uterus is accomplished by inserting a special tool into the uterus that carries electric current that ultimately heats and destroys the layer of the endometrium. Exemplary tools can have wire loop 3304, depicted in FIG. 33C, spiked ball, triangular mesh, roller ball or inflatable balloon 3302 depicted in FIG. 33B, or wings 3300 depicted in FIG. 33A. In a further specific implementation, a power generator delivers up to 180 W at 500 KHz to ablate the endometrium to a uniform depth with a programmed treatment cycle of 40-120 seconds. In an alternate further specific implementation heating of inflatable balloon 3302 is accomplished to maintain a surface temperature of approximately 70-75° C. during a 4-minute treatment session.

Accordingly, Exemplary tools depicted in FIGS. 33A-33C can also be used to promote uniform heating of heating catheter 102 by properly centering heating element 106 within the vein lumen. Additionally, FIGS. 34A and 34B depict another tool or technique for promoting uniform heating. In this example, heating element 106 is provided on two parallel tube that are bent away from each other or bowed away, as shown in FIG. 34A, at rest and parallel next to each other when a force is applied to heat element 106 from the side. Thus, in the vein lumen, each heating element 106 will push against the side of the vein lumen, ensuring uniform heating, and will squeeze together when they encounter a smaller section, for example.

In a specific implementation a similar energy delivery system is used in the treatment of cancerous lesions, such as in the liver, lung, breasts, kidney and bone. In this treatment heat is typically applied directly within the tumor, such as via a needle with a heating element or with one or more electrodes for delivery of radiofrequency energy, or by a multitude of needles that deliver RF energy.

In a specific implementation a similar energy delivery system is used in the treatment of back pain, such as by radiofrequency neurotomy. In this treatment, heat is applied to targeted nerve pathways to shut off the transmission of pain signals to the brain. A needle with one or more electrodes, or a heating element, is directed through gaps in the spine into a treatment region of inflamed nervous tissue.

In a specific implementation a similar energy delivery system is used in the treatment of Barretts esophagus, which is a condition in which the normal squamous epithelium is replaced by specialized columnar-type epithelium known as intestinal metaplasia, in response to irritation and injury caused by gastroesophageal reflux disease (GERD). In this treatment, heat is applied directly to the Barrett's lining of the Esophagus. In a further specific implementation an energy delivery system works with an ablation catheter that has an inflatable balloon with plate-based heating elements or electrodes.

Example manufacturing assembly steps can include cutting main shaft tubing (e.g., Polyimide tubing) to length. Printing (e.g., laser etch or pad print; alternatively pad printing after surface treatment such as plasma) exterior shaft markings onto main shaft tubing and cure to dry. Shaft markings can include sequential markings for alignment by the user, as well as processing guidance markings such as the location of the heating element ends and pass-through holes.

Drilling (e.g., laser processing or sharpened hole cutter), punch or skive pass-through holes for wires into the region where the heating element will be located. Cleaning or abrading at least the soldering locations on the heating element to remove oxidation, such as by sanding, grit blasting or acid etching (which can be included in acid soldering flux). In one example, a pre-tin process is applied to the soldering locations of the heating element, such as with silver solder and hydrochloric acid flux. Clean or neutralize the heating element. Loading the heating element onto the main shaft tubing, aligning the element with processing guidance markings (if present). If a coil heating element is of a size smaller than the shaft tubing so that it cannot be slid linearly over the tubing, rotate the heating element or the shaft (or counter-rotate the two relative to each other) in the direction that opens up the coil to allow it to slide over the tubing.

The coil heating element can be snugged in place by counter-rotating the two coil ends to tighten the coil onto the shaft tubing. The connection wires (e.g., 28-32 G copper 'magnet wire') can be soldered to the appropriate locations on the heating element; example solder locations are to side-lap the last ¼ to ½ coil at each end with the copper wire, or to sandwich the copper wire between a portion of the last two coils. Prior to soldering remove the insulation from the end of the wire, such as by cutting, brushing or scraping it off, so that approximately 2-5 mm is exposed bare wire. The connection wires can be threaded through the nearest pass-through holes to the proximal end of the shaft. A thermocouple (or thermistor) can be threaded through a pass-through hole near the location of temperature sensing and locate the thermocouple junction (or thermistor bulb) between coil winds so that there is no coil-to-coil short circuit (prevented by an air gap or an insulated layer such as PET). Affix the thermocouple into position such as with cyanoacrylate adhesive.

Slide a lubricious outer jacket over the heating element, align it to cover the desired areas and heat shrink it to tightly cover the heating element. Slide a guide wire lumen through the inside of the shaft tubing and align it so the distal end of the guide wire tubing extends approximately 1.0 to 3.0 mm beyond the distal end of the shaft tubing. Apply adhesive, such as UV cured acrylic or cyanoacrylate, at the distal tip to bond the two tubes together and provide a rounded atraumatic tip; maintain complete access to the guide wire lumen inner diameter.

Accordingly, the steps above can be followed for another implementation of a heating element, but this time a third wired connection can be added to the heating element at a point along its length (for example, 2.5 cm from the distal end of the coil). Additionally, instead of using a pass-through hole for the thermocouple to enter the shaft tubing near its sensed location, wind the thermocouple wire in a coiled manner in the space between successive heating coils. Note that this same coil-space winding can be used for the third wired connection as in exemplary heating element subassembly B, and the two windings may be alongside each other within the coil spacings, extending opposite directions along the coil spacings or a combination of the two.

In another example, instead of using a pass-through hole for the thermocouple to enter the shaft tubing near its sensed location, lay the thermocouple wire atop the heating coil so that it is trapped in place between the heating coil and the lubricious outer jacket; it is important for sufficient electrical insulation to cover the thermocouple wire(s) to prevent short-circuiting of the heating element coils. A strip of insulation between the thermocouple and the coil can be used, along the entire length that the thermocouple wire(s) overlay the heating coil or just along the end of the thermocouple wire where the ends are stripped to create the junction; alternatively, the coil can be covered with shrink tubing or Parylene or similar coating to prevent electrical contact with the thermocouple. One method of aligning a film strip of insulation is to include two holes or straps near one end of the strip that the thermocouple wire can be passed through to hold it strip in place extending past the area of the thermocouple junction.

Another method of aligning the strip is to glue it, as with cyanoacrylate. Note that this same wire-atop-coil configuration can be used for the third wired connection as in exemplary heating element subassembly B. One method of locating the thermocouple in the desired location prior to heat-shrinking the lubricious outer jacket into place is to thread a filament (cotton or polymer or other) through the location of the thermocouple junction and then affix as with tape the thermocouple wire at one end of the coil assembly and the filament at the other end to hold the junction in place during while the lubricious outer jacket is shrunk into place trapping the thermocouple wire. One method of keeping the wire profile atop the heating coil from protruding completely along the outside of the heating coil is to deform the heating coil inward along the tract of the thermocouple wire, such as by crimping the heating coil (possibly including the tube it is loaded onto) in a die crimping fixture.

Instead of placing a thermocouple between the heating coils place a thermistor underneath the heating coil, preferably in direct contact with the inside surface of the heating coil. One way to locate the thermistor is to cut a window in the main shaft tubing so that the thermistor axis is parallel with the main shaft tubing axis and one side of the thermistor is even with or protrudes slightly above the surface of the main shaft tubing. One means of holding the thermistor in that position is to cut the window in the main shaft tubing leaving one or more straps that invert into the lumen of the main shaft tubing to cradle the thermistor and hold it from falling unsupported into the lumen of the main shaft tubing. Another means of holding the thermistor in place is to place a shaped plug alongside or underneath the thermistor to hold it from falling unsupported into the lumen of the main shaft tubing. A layer of thin heat shrink tubing can be placed over the main shaft tubing to hold the thermistor into place prior to loading the heating coil.

If the Heating Element Subassembly does not comprise the full length of the catheter shaft that will be inserted into the patient, bond an additional length of proximal shaft tubing (e.g., 72D Pebax, Polyimide or other material) with printed shaft marks to the proximal end of the main shaft tubing. This bond can be adhesive such as cyanoacrylate or UV-cured acrylic, or it can be heat-bonded. An exemplary heat bond at that location would be to melt Pebax proximal shaft tubing to Polyimide main shaft tubing that has a thin Pebax outer layer.

A cable assembly (with electrical cable having a plug-in connector for energy delivery console 104 at one end and a cable anchor and handle circuit board assembly at the other) is assembled with an A-side of a handle assembly. A strain relief is placed over the proximal end of a catheter or heating element assembly. The catheter of heating element assembly is then bonded to the A-side of the handle assembly. Wires from the catheter or heating element assembly are electrically connected with (e.g., soldered) to the handle circuit board assembly, and exposed electrical surfaces are potted with insulating material such as UV adhesive. A button component or components may be assembled into the B-side of a handle assembly (or the button functionality may be designed into a deflecting portion of one or both of the A- and B-sides) and the A- and B-sides of the handle assembly are mated together. The two halves may be mated together by press-fit post-and-hole configurations, by adhesive bonding, by solvent bonding or by ultrasonic welding. The strain relief may be mated to the handle assembly by any of the methods listed previously.

The catheter may be tested to assure that all electrical connections are effective, such as measuring a reference temperature via the included temperature sensor, measuring the electrical resistance across the heating element, and measuring the effectiveness of the identification components. A heating catheter electronic control engine may be programmed with a code, status allowing treatments with a user's energy delivery system, and possibly with measured data such as a record of testing and/or test results.

The catheter may be inserted into a coiled protective tube such as polyethylene, with the handle fitting either directly to the end of the tube, to the side of the adjacent tube or to an intermediate holder. The electrical cable may be coiled to fit within or alongside the protective coil area. This coiled assembly may be slipped within a protective pouch such as TYVEK®/MYLAR® and the open end of the pouch is heat-sealed. This pouch is placed within a chipboard paper carton, along with printed instructions for use, with appropriate labeling covering one or more of the end flaps.

In a specific implementation, a catheter with a heating element has expandable/collapsible features intended to keep the heating element portion of the catheter more centered within the treatment vessel lumen as the vessel lumen is collapsed flat upon itself (as by external unidirectional compression of the surrounding tissue) with the heating element within the vessel lumen. In a specific implementation, the heating element portion of the catheter is curved in a pattern that provides a flattened serpentine orientation of the heating element along the vessel lumen as the vessel lumen is collapsed flat. In a specific implementation, the heating element portion of the catheter is curved in a spiral orientation to help it contact the surface of the vessel lumen if the vessel lumen is much larger than the size of the heating element.

In order to minimize number of conductors in a device cable assembly, with associated reduced number of conductors in the device connector, one particular implementation consists of three conductors: a power conductor, a communication line conductor and a shared return path (ground) for power and communication. Sharing a return path for high levels of power current causes a voltage drop across the return path conductor, which interferes with the reference voltage of the communication signal.

In a particular implementation, dedicated circuitry (combination of filter, discriminator and Schmitt buffer) is used to recreate the original shape (information) of the communication signal. The low-pass filter of nonzero gain filters out the noise components that are induced in the communication cable by changes of current in the power conductor. The discriminator recreates the main shape of the signal. The Schmitt buffer further converts the signal so that it meets digital signal requirements such as signal level and slew rate.

In a simulation of this particular implementation signal shapes at particular stages of the circuit are shown. Trace 1 shows an input (communication) signal carrying required information. Trace 2 shows exemplary noise (of both high and low frequencies) generated by the environment, e.g., the current changes in the power conductor. Trace 3 shows the signal with the combined effect of the signal from trace 1 and the noise from trace 2. Trace 4 shows the shape of the signal after the low-pass filter has removed the noise and amplified the signal; this signal shows inadequate timing and slew rate, as well as parasitic glitches. Trace 5 shows the signal at the output of the discriminator; the glitches have been removed, but the signal still shows inadequate slew rate. Trace 6 shows the signal at the output of the Schmitt buffer; here the signal shows sufficient quality for retrieving the information it carried. Comparing signals 6 (output) and 1 (input) shows adequate communication of signal information, with minor degradation of timing; voltages are intentionally different to be consistent with sending and receiving systems.

These and other examples provided in this paper are intended to illustrate but not necessarily to limit the described implementation. As used herein, the term "implementation" means an implementation that serves to illustrate by way of example but not limitation. The techniques described in the preceding text and figures can be mixed and matched as circumstances demand to produce alternative implementations.

As used herein, the term "embodiment" means an embodiment that serves to illustrate by way of example but not limitation. The techniques described in the preceding text and figures can be mixed and matched as circumstances demand to produce alternative embodiments.

We claim:

1. A system comprising:
a heating catheter including a heating element;
an energy delivery console;
a serial communication cable connecting the heating catheter to the energy delivery console including:
a power delivery wire;
a communication wire;
a shared ground wire providing a return path for the power delivery wire and the communication wire to the energy delivery console; and
further comprising: one or more charge pumps, wherein, in operation, the one or more charge pumps increase voltage to transistors connecting the heating element to energy delivery circuitry.

2. The system of claim 1, wherein at least one of measured temperature data, start/stop button status data, intended treatment area data, heating catheter identification data, heating catheter calibration data, or heating catheter use history data is communicated to the energy delivery console via the shared ground wire.

3. The system of claim 1, wherein the serial communication cable includes a tip, ring, and sleeve (TRS) connector, the tip corresponding to the power delivery wire, the ring corresponding to the communication wire, and the sleeve corresponding to the shared ground wire.

4. The system of claim 1, wherein the serial communication cable includes a tip, ring, and sleeve (TRS) connector, the tip corresponding to the power delivery wire, comprising a short circuit protection module protecting the heating catheter in an event the TRS connector is pulled into a shorting position while power is being provided over the power delivery wire.

5. The system of claim 1, wherein the heating element is a resistance heating element or one or more monopolar or bipolar ablation electrodes.

6. The system of claim 1, wherein the heating element includes a plurality of heating lengths to provide a selectable heating length of the heating element.

7. The system of claim 1, wherein the heating element includes a plurality of heating lengths, wherein at least one of the plurality of heating lengths can be turned on by selecting an image of the heating catheter displayed on the energy delivery console.

8. The system of claim 1, wherein the heating element includes a plurality of heating lengths that are, in operation, turned on by selecting a button on the heating catheter.

9. The system of claim 1, comprising a pull-tab attached to packaging of the heating catheter so that when a user removes the heating catheter from the heating catheter packaging the pull-tab pulls away automatically.

10. The system of claim 1, wherein at least two of the power delivery wire, the communication wire, and the shared ground wire are siamesed into a flat bundle or multi-layered to ease loading of the wires.

11. A heating catheter comprising:
   a heating element;
   a communication cable connecting the heating catheter to an energy delivery console, the communication cable including:
      a power delivery wire;
      a communication wire; and
      a shared ground wire providing a return path for the power delivery wire and the communication wire to the energy delivery console,
   wherein the communication cable includes a tip, ring, and sleeve (TRS) connector, the tip corresponding to the power delivery wire, comprising: a short circuit protection module protecting the heating catheter in an event the TRS connector is pulled into a shorting position while power is being provided over the power delivery wire.

12. The heating catheter of claim 11, wherein the heating element includes a plurality of heating lengths to provide a selectable heating length of the heating element.

13. The heating catheter of claim 11, wherein the heating element includes a plurality of heating lengths, comprising:
   at least one temperature sensor corresponding to a first and second heating length of the plurality of heating lengths;
   a control engine providing temperature information from the at least one temperature sensor to the energy delivery console.

14. The heating catheter of claim 11, wherein the heating element includes a plurality of heating lengths wherein at least one of the plurality of heating lengths can be turned on by selecting an image of the heating catheter displayed on the energy delivery console.

15. The heating catheter of claim 11, wherein the heating element includes a plurality of heating lengths that are, in operation, turned on by selecting a button on the heating catheter.

16. The heating catheter of claim 11, wherein at least one of measured temperature data, start/stop button status data, intended treatment area data, heating catheter identification data, heating catheter calibration data, or heating catheter use history data is communicated to the energy delivery console via the shared ground wire.

17. The heating catheter of claim 11, wherein the communication cable includes a tip, ring, and sleeve (TRS) connector, the tip corresponding to the power delivery wire, the ring corresponding to the communication wire, and the sleeve corresponding to the shared ground wire.

18. The heating catheter of claim 11, wherein the heating element is configured to heat only along a user selected length.

19. The heating catheter of claim 11, wherein the heating element is configured to heat along an entire length of the heating element or to heat along only a distal portion of the heating element.

20. The heating catheter of claim 11, wherein the heating element is configured to heat along an entire length of the heating element or to heat along only a first distal portion of the heating element or to heat only along a second distal portion of the heating element.

21. The heating catheter of claim 11, wherein the heating element is configured to heat only along a first selectable length or to heat only along a second selectable length, wherein the second selectable length includes at least the first selectable length.

22. The heating catheter of claim 11, wherein the heating element is configured to heat along an entire length of 10 cm or to heat along only an 1 cm segment in a distal portion of the heating element.

23. The heating catheter of claim 11, wherein the heating element is configured to heat along an entire length of 10 cm or to heat along only a 2.5 cm segment in a distal portion of the heating element.

24. The heating catheter of claim 11, wherein the heating element is configured to heat along an entire length of 7 cm or to heat along only a 3 cm segment in a distal portion of the heating element.

25. The heating catheter of claim 11, wherein the heating element is configured to heat along an entire length of 6 cm or to heat along only a 2 cm segment in a distal portion of the heating element.

26. The heating catheter of claim 11, wherein the heating element is configured to heat along an entire length of 10 cm or to heat along only a 3.0 cm segment in a distal portion of the heating element or to heat along only a 1 cm segment in a distal portion of the heating element.

27. A communication cable connecting a heating catheter to an energy delivery console comprising:
   a power delivery wire;
   a communication wire comprising a tip, ring, and sleeve (TRS) connector, the sleeve corresponding to the shared ground wire, wherein a grounded external shielding is in common with the sleeve of the shared ground wire, wherein the sleeve is not attached to ground at the heating catheter; and
   a shared ground wire providing a return path for the power delivery wire and the communication wire to the energy delivery console.

28. The communication cable of claim 27, comprising a grounded external shielding.

29. The communication cable of claim 27, comprising a tip, ring, and sleeve (TRS) connector, the tip corresponding to the power delivery wire, the ring corresponding to the communication wire, and the sleeve corresponding to the shared ground wire.

30. A heating catheter system, comprising:
   a heating element;
   an energy delivery console having a push to engage socket;
   a communication cable connecting the heating catheter to the energy delivery console, the communication cable including:
      a power delivery wire;
      a communication wire;
      a shared ground wire providing a return path for the power delivery wire and the communication wire to the energy delivery console,
   wherein the communication cable includes a tip, ring, and sleeve (TRS) connector, the tip corresponding to the power delivery wire, wherein the push to engage socket is configured to receive the tip, ring and sleeve (TRS) connector.

31. The heating catheter system of claim 30 wherein the push to engage socket includes a switch configured to allow power connection only when the tip, ring, sleeve (TRS) connector is seated within the socket.

32. The heating catheter of claim 30, wherein the heating element includes a plurality of heating lengths to provide a selectable heating length of the heating element.

33. The heating catheter of claim 30, wherein the heating element includes a plurality of heating lengths, comprising:
at least one temperature sensor corresponding to a first and second heating length of the plurality of heating lengths;
a control engine providing temperature information from the at least one temperature sensor to the energy delivery console.

34. The heating catheter of claim 30, wherein the heating element includes a plurality of heating lengths wherein at least one of the plurality of heating lengths can be turned on by selecting an image of the heating catheter displayed on the energy delivery console.

35. The heating catheter of claim 30, wherein the heating element includes a plurality of heating lengths that are, in operation, turned on by selecting a button on the heating catheter.

36. The heating catheter of claim 30, the energy delivery console further comprising a display screen wherein at least one of measured temperature data, start/stop button status data, intended treatment area data, heating catheter identification data, heating catheter calibration data, or heating catheter use history data communicated to the energy delivery console via the shared ground wire is visible on the display screen.

37. The heating catheter of claim 30, wherein in the tip, ring, and sleeve (TRS) connector, the ring corresponds to the communication wire, and the sleeve corresponds to the shared ground wire.

38. The heating catheter of claim 30, wherein the heating element is configured to heat only along a user selected length.

39. The heating catheter of claim 30, wherein the heating element is configured to heat along an entire length of the heating element or to heat along only a distal portion of the heating element.

40. The heating catheter of claim 30, wherein the heating element is configured to heat along an entire length of the heating element or to heat along only a first distal portion of the heating element or to heat only along a second distal portion of the heating element.

41. The heating catheter of claim 30, wherein the heating element is configured to heat only along a first selectable length or to heat only along a second selectable length, wherein the second selectable length includes at least the first selectable length.

42. The heating catheter of claim 30, wherein the heating element is configured to heat along an entire length of 10 cm or to heat along only an 1 cm segment in a distal portion of the heating element.

43. The heating catheter of claim 30, wherein the heating element is configured to heat along an entire length of 10 cm or to heat along only a 2.5 cm segment in a distal portion of the heating element.

44. The heating catheter of claim 30, wherein the heating element is configured to heat along an entire length of 7 cm or to heat along only a 3 cm segment in a distal portion of the heating element.

45. The heating catheter of claim 30, wherein the heating element is configured to heat along an entire length of 6 cm or to heat along only a 2 cm segment in a distal portion of the heating element.

46. The heating catheter of claim 30, wherein the heating element is configured to heat along an entire length of 10 cm or to heat along only a 3.0 cm segment in a distal portion of the heating element or to heat along only a 1 cm segment in a distal portion of the heating element.

* * * * *